United States Patent
Kamata et al.

(10) Patent No.: US 11,274,101 B2
(45) Date of Patent: Mar. 15, 2022

(54) HETEROCYCLIC COMPOUND

(71) Applicant: Takeda Pharmaceutical Company Limited, Osaka (JP)

(72) Inventors: Makoto Kamata, Kanagawa (JP); Hideyuki Sugiyama, Kanagawa (JP); Minoru Nakamura, Kanagawa (JP); Masataka Murakami, Kanagawa (JP); Shuhei Ikeda, Kanagawa (JP); Tomohiro Okawa, Kanagawa (JP); Hidekazu Tokuhara, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 77 days.

(21) Appl. No.: 16/651,840

(22) PCT Filed: Sep. 27, 2018

(86) PCT No.: PCT/JP2018/035827
§ 371 (c)(1),
(2) Date: Mar. 27, 2020

(87) PCT Pub. No.: WO2019/065791
PCT Pub. Date: Apr. 4, 2019

(65) Prior Publication Data
US 2020/0255439 A1    Aug. 13, 2020

(30) Foreign Application Priority Data
Sep. 29, 2017    (JP) .................... JP 2017-190838

(51) Int. Cl.
| | | |
|---|---|---|
| *C07D 487/10* | (2006.01) | |
| *A61P 25/28* | (2006.01) | |
| *A61K 9/20* | (2006.01) | |
| *A61K 9/48* | (2006.01) | |

(52) U.S. Cl.
CPC .......... *C07D 487/10* (2013.01); *A61K 9/2013* (2013.01); *A61K 9/2018* (2013.01); *A61K 9/2054* (2013.01); *A61K 9/2059* (2013.01); *A61K 9/4858* (2013.01); *A61K 9/4866* (2013.01); *A61P 25/28* (2018.01)

(58) Field of Classification Search
CPC .................................................. C07D 487/10
See application file for complete search history.

(56) References Cited

U.S. PATENT DOCUMENTS

| | | |
|---|---|---|
| 2010/0324011 A1 | 12/2010 | Bian et al. |
| 2010/0324012 A1 | 12/2010 | Bian et al. |
| 2010/0324013 A1 | 12/2010 | Bian et al. |
| 2010/0324014 A1 | 12/2010 | Bian et al. |
| 2010/0324015 A1 | 12/2010 | Chevalier et al. |
| 2010/0324016 A1 | 12/2010 | Flores et al. |
| 2010/0331299 A1 | 12/2010 | Bian et al. |
| 2010/0331300 A1 | 12/2010 | Bian et al. |
| 2011/0015170 A1 | 1/2011 | Bian et al. |
| 2011/0015171 A1 | 1/2011 | Bian et al. |
| 2012/0058986 A1 | 3/2012 | Connolly et al. |
| 2012/0077797 A1 | 3/2012 | Connolly et al. |
| 2013/0085129 A1 | 4/2013 | Connelly et al. |
| 2013/0085130 A1 | 4/2013 | Connelly et al. |
| 2013/0102584 A1 | 4/2013 | Connolly et al. |
| 2013/0102585 A1 | 4/2013 | Bian et al. |
| 2013/0123232 A1 | 5/2013 | Bian et al. |
| 2013/0123233 A1 | 5/2013 | Bian et al. |
| 2013/0137674 A1 | 5/2013 | Bian et al. |
| 2013/0184251 A1 | 7/2013 | Chevalier et al. |

(Continued)

FOREIGN PATENT DOCUMENTS

| | | |
|---|---|---|
| CN | 104379578 A | 2/2015 |
| CN | 105517547 A | 4/2016 |

(Continued)

OTHER PUBLICATIONS

Levins, C.G., et al. "The Synthesis of Functionalized Nanoscale Molecular Rods of Defined Length." J. Am. Chem. Soc. (2003), vol. 125, pp. 4702-4703. (Year: 2003).*

Almeida-Santos et al., "Modulation of anxiety-like behavior by the endocannabinoid 2-arachidonoylglycerol (2-AG) in the dorsolateral periaqueductal gray," Behavioural Brain Research, 2013, 252:10-17.

Ashton et al., "Expression of the cannabinoid CB2 receptor in the rat cerebellum: An immunohistochemical study," Neuroscience Letters, 2006, 396:113-116.

Aso et al., "$CB_1$ Agonist ACEA Protects Neurons and Reduces the Cognitive Impairment of AβPP/PS1 Mice," Journal of Alzheimer's Disease, 2012, 30:439-459.

(Continued)

*Primary Examiner* — John S Kenyon
(74) *Attorney, Agent, or Firm* — Foley & Lardner LLP

(57) ABSTRACT

The present invention provides a compound having an MAGL inhibitory action, and expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like.

The present invention relates to a compound represented by the formula (I):

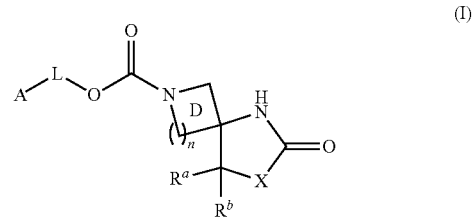

wherein each symbol is as defined in the description, or a salt thereof.

12 Claims, No Drawings
Specification includes a Sequence Listing.

(56) References Cited

U.S. PATENT DOCUMENTS

| | | | |
|---|---|---|---|
| 2013/0196968 | A1 | 8/2013 | Connolly et al. |
| 2013/0196969 | A1 | 8/2013 | Connolly et al. |
| 2013/0217669 | A1 | 8/2013 | Bian et al. |
| 2013/0237517 | A1 | 9/2013 | Bian et al. |
| 2013/0244997 | A1 | 9/2013 | Bian et al. |
| 2013/0244998 | A1 | 9/2013 | Connolly et al. |
| 2013/0296297 | A1 | 11/2013 | Flores et al. |
| 2014/0243305 | A1 | 8/2014 | Bian et al. |
| 2015/0080364 | A1 | 3/2015 | Cisar et al. |
| 2016/0137649 | A1 | 5/2016 | Jones et al. |
| 2016/0318864 | A1 | 11/2016 | Koike et al. |
| 2017/0029390 | A1 | 2/2017 | Butler et al. |
| 2017/0166568 | A1 | 6/2017 | Babiss et al. |
| 2017/0283406 | A1 | 10/2017 | Ikeda et al. |
| 2018/0065943 | A1 | 3/2018 | Butler et al. |
| 2018/0079759 | A1 | 3/2018 | Chellappan et al. |
| 2018/0282332 | A1 | 10/2018 | Babiss et al. |
| 2019/0225611 | A1 | 7/2019 | Babiss et al. |
| 2019/0382359 | A1 | 12/2019 | Butler et al. |

FOREIGN PATENT DOCUMENTS

| | | | | |
|---|---|---|---|---|
| CN | | 107106559 A | 8/2017 | |
| RU | | 2355690 C2 | 5/2009 | |
| WO | WO 2010/124082 | A1 | 10/2010 | |
| WO | WO 2010/124086 | A1 | 10/2010 | |
| WO | WO 2010/124121 | A1 | 10/2010 | |
| WO | WO 2010/124122 | A1 | 10/2010 | |
| WO | WO 2012/030907 | A1 | 3/2012 | |
| WO | WO 2012/044613 | A1 | 4/2012 | |
| WO | WO 2012/054716 | A1 | 4/2012 | |
| WO | WO 2013/049289 | A1 | 4/2013 | |
| WO | WO 2013/049293 | A1 | 4/2013 | |
| WO | WO 2015/099196 | A1 | 7/2015 | |
| WO | WO 2016/158956 | A1 | 10/2016 | |
| WO | WO2017/021805 | A1 | 2/2017 | |
| WO | WO-2017/087854 | A1 | 5/2017 | |
| WO | WO 2017/171100 | A1 | 10/2017 | |
| WO | WO-2017170830 | A1 * | 10/2017 | ........... A61K 31/407 |

OTHER PUBLICATIONS

Chen et al., "Endocannabinoid 2-arachidonoylglycerol protects neurons against β-amyloid insults," Neuroscience, 2011, 178:159-168.

Devane et al., "Determination and Characterization of a Cannabinoid Receptor in Rat Brain," Molecular Pharmacology, 1988, 34:605-613.

Dinh et al., "A role for monoglyceride lipase in 2-arachidonoylglycerol inactivation," Chemistry and Physics of Lipids, 2002, 121:149-158.

Funk, Colin D., "Prostaglandins and Leukotrienes: Advances in Eicosanoid Biology," Science, Nov. 30, 2001, 294:1871-1875.

Greco et al., "Activation of CB2 receptors as a potential therapeutic target for migraine: evaluation in an animal model," Journal of Headache and Pain, 2014, 15:14(1-8).

Guindon et al., "The antinociceptive effects of intraplantar injections of 2-arachidonoyl glycerol are mediated by cannabinoid $CB_2$ receptors," British Journal of Pharmacology, 2007, 150:693-701.

Joice et al., "Modulation of blood-brain barrier permeability by neutrophils: in vitro and in vivo studies," Brain Research, 2009, 1298:13-23.

Khasabova et al., "Increasing 2-arachidonoyl glycerol signaling in the periphery attenuates mechanical hyperalgesia in a model of bone cancer pain," Pharmacological Research, 2011, 64:60-67.

Kim et al., "AM1241, a cannaboid CB2 receptor selective compound, delays disease progression in a mouse model of amyotrophic lateral sclerosis," European Journal of Pharmacology, 2006, 542:100-105.

Lara-Celador et al., "Endocannabinoids reduce cerebral damage after hypoxic-ischemic injury in perinatal rats," Brain Research, 2012, 1474:91-99.

Lourbopoulos et al., "Administration of 2-arachidonoylglycerol ameliorates both acute and chronic experimental autoimmune encephalomyelitis," Brain Research, 2011, 1390:126-141.

Lue et al., "Microglia Activation and Anti-inflammatory Regulation in Alzheimer's Disease," Molecular Neurobiology, 2010, 41:115-128.

Maroso et al., "Toll-like receptor 4 and high-mobility group box-1 are involved in ictogenesis and can be targeted to reduce seizures," Nature Medicine, Apr. 2010, 16(4):413-419.

Mechoulam et al., "Identification of an endogenous 2-monoglyceride, present in canine gut, that binds to cannabinoid receptors," Biochemical Pharmacology, 1995, 50(1):83-90.

Naderi et al., "Modulation of Anticonvulsant Effects of Cannabinoid Compounds by GABA-A Receptor Agonist in Acute Pentylenetetrazole Model of Seizure in Rat," Neurochemical Research, 2011, 36:1520-1525.

Njie et al., "Aqueous humor outflow effects of 2-arachidonylglycerol," Experimental Eye Research, 2008, 87:106-114.

Nomura et al., "Endocannabinoid Hydrolysis Generates Brain Prostaglandins That Promote Neuroinflammation," Science, Nov. 11, 2011, 334:809-813.

Ouchi et al., "Microglial Activation and Dopamine Terminal Loss in Early Parkinson's Disease," Ann. Neurol, 2005, 57:168-175.

Palazuelos et al., "Microglial $CB_2$ cannabinoid receptors are neuroprotective in Huntington's disease excitotoxicity," Brain, 2009, 132:3152-3164.

Panikashvili et al., "An endogeneous cannabinoid (2-AG) is neuroprotective after brain injury," Nature, Oct. 4, 2001, 413:527-531.

Patel et al., "Loratadine analogues as MAGL inhibitors," Bioorganic & Medicinal Chemistry Letters, Feb. 24, 2015, 25(7):1436-1442.

Perry et al., "Microglia in neurodegenerative disease," Nature Reviews Neurology, Apr. 2010, 6:193-201.

Piro et al., "A Dysregulated Endocannabinoid-Eicosanoid Network Supports Pathogenesis in a Mouse Model of Alzheimer's Disease," Cell Reports, Jun. 28, 2012, 1:617-623.

Turner et al., "Evidence of widespread cerebral microglial activation in amyotrophic lateral sclerosis: an [$^{11}$C](R)-PK11195 positron emission tomography study," Neurobiology of Disease, 2004, 15:601-609.

Yoshiyama et al., "Synapse Loss and Microglial Activation Precede Tangles in a P301S Tauopathy Mouse Model," Neuron, Feb. 1, 2007, 53:337-351.

Zhong et al., "Monoacylglycerol Lipase Inhibition Blocks Chronic Stress-Induced Depressive-Like Behaviors via Activation of mTOR Signaling," Neuropsychopharmacology, 2014, 39:1763-1776.

Patel et al. "Loratadine analogues es MAGL inhibitors," Bioorganic & Medicinal Chemistry Letters, Feb. 24, 2015, 25:1436-1442.

* cited by examiner

SEQUENCE LISTING

```
<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: primer

<400> SEQUENCE: 1
ccaccatcat cacggatcca tgccagagga aagttccccc a                          41

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
tggtgctcga gtgcggccgc tcagggtggg gacgcagttc                            40
```

HETEROCYCLIC COMPOUND

CROSS-REFERENCE TO RELATED APPLICATIONS

This application is the U.S. National Stage of PCT/JP2018/35827, filed Sep. 27, 2018, which claims priority to JP 2017-190838, filed Sep. 29, 2017.

The instant application contains a Sequence Listing which has been submitted in ASCII format via EFS-WEB and is hereby incorporated by reference in its entirety. Said ASCII copy, created on Mar. 17, 2020, is named sequence.txt and is 585 bytes.

TECHNICAL FIELD

The present invention relates to a heterocyclic compound having a monoacylglycerol lipase (sometimes to be abbreviated as "MAGL" in the present specification) inhibitory action, a medicament containing same and the like.

BACKGROUND OF THE INVENTION

Arachidonic acid (sometimes to be abbreviated as "AA" in the present specification) and its product in vivo, eicosanoid, have been reported to cause inflammation in the central and peripheral nervous systems [non-patent document 1: Science, vol. 294, pages 1871-1875, 2001]. An inhibitor that suppresses arachidonic acid production pathway and eicosanoid production pathway is promising as a therapeutic drug for inflammatory diseases, and non-steroidal anti-inflammatory drugs such as cyclooxygenase inhibitor and the like have been used as therapeutic drugs for inflammatory pain. However, when a cyclooxygenase inhibitor is used for a long time, digestive tract disorders are sometimes developed as side effects, thus posing a problem. In addition, circulatory side effects such as myocardial infarction, cerebral infarction and the like also pose problems in recent years.

Brain inflammation accompanied by activation of glial cells has been suggested to be a pathological change characteristic of neurodegenerative diseases (e.g., Alzheimer's disease etc.) [non-patent document 2: Molecular Neurobiology (Mol. Neurobiol), vol. 41, pages 115-128, 2010]. It has been reported that anti-inflammatory drugs suppress activation of glial cells and suppress neurodegenerative progression in an animal model of tau overexpression (human variant tau transgenic mouse etc.) which is a pathological characteristic of Alzheimer's disease [non-patent document 3: Neuron, vol. 53, pages 337-351, 2007]. In addition, the effectiveness of suppression of brain inflammation for the treatment of neurodegenerative diseases such as Alzheimer's disease and the like has been suggested [non-patent document 4: Nature Reviews Neurology (Nat. Rev. Neurol.), vol. 6, pages 193-201, 2010], and a therapeutic drug that suppresses brain inflammation is promising as a therapeutic or prophylactic drug for neurodegenerative diseases.

Monoacylglycerol lipase (MAGL) is an enzyme that hydrolyzes monoacylglycerol into fatty acid and glycerol. In the central nervous system, the substrate of MAGL is 2-arachidonoylglycerol (also referred to as 2-AG in the present specification) which is decomposed into arachidonic acid and glycerol [non-patent document 5: Chemistry and Physics of Lipids (Chem phys Lipids) vol. 121, pages 149-158, 2002]. In recent years, suppression of production of arachidonic acid and eicosanoids, suppression of activation of glial cell, suppression of production of inflammatory cytokine, and a decreasing action on the accumulation of Aβ plaque which is a pathologic finding of Alzheimer's disease have been reported in a crossbred animal of MAGL deficient mouse and amyloid P (to be also referred to as Aβ in the present specification) overexpressing animal model (APP/PS1 double transgenic mouse etc.) [non-patent document 6: Cell Report (Cell Rep.), vol. 1, pages 617-623, 2012], and an inhibitor etc. that suppress the action of MAGL are promising as a therapeutic or prophylactic drug for Alzheimer's disease.

In addition, as receptors of 2-AG, which is a substrate of MAGL, cannabinoid receptor 1 (to be referred to as CB1 in the present specification) and cannabinoid receptor 2 (to be referred to as CB2 in the present specification) have been identified [non-patent document 7: Biochemical Pharmacology (Biochem. Pharmcol.) vol. 50, 83-90, 1995]. CB1 is mainly expressed in the brain region [non-patent document 8: Molecular Pharmacology (Mol. Pharmacol.), vol. 34, pages 605-613, 1988], and CB2 is expressed in immunocyte, and microglial cell in the brain region [non-patent document 9: Neuroscience Letters (Neurosci. Lett.), vol. 396, pages 113-116, 2006]. In recent years, it has been reported that CB1 receptor agonist improves cognition function [non-patent document 10: Journal of Alzheimer's Disease (J. Alzheimers. Dis.), vol. 30, pages 439-459, 2012], and 2-AG, which is the substrate of MAGL, shows a protective action against nerve cell death due to AR [non-patent document 11: Neuroscience, vol. 178, pages 159-168, 2011]. Therefore, MAGL inhibitor that suppresses decomposition of 2-AG is promising as a therapeutic or prophylactic drug that has effects not only to relief symptoms but also to suppress disease progression, by suppressing inflammation in brain, nerve cell death, Aβ accumulation and the like observed in Alzheimer's disease.

Parkinson's disease, which is one of the neurodegenerative diseases, is a disease associated with movement disorders caused by the degeneration of midbrain substantia nigra dopamine nerve cells, in which activation of glial cell has been reported [non-patent document 12: Annals of Neurology (Ann. Neurol.) vol. 57, pages 168-175, 2005]. While 1-methyl-4-phenyl-1,2,3,6-tetrahydropyridine is known to induce cell death of midbrain substantia nigra dopamine nerve, it has been reported to show a protective action against nerve cell death in MAGL deficient mouse [non-patent document 13: Science, vol. 334, pages 809-813, 2011]. Therefore, an inhibitor etc. that suppress the action of MAGL are promising as new therapeutic drugs for Parkinson's disease.

Amyotrophic lateral sclerosis (to be referred to as ALS in the present specification) is a disease associated with degeneration of motor neuron, and no effective treatment exists at present. Activation of glial cell in ALS has been reported [non-patent document 14: Neurobiology of Disease (Neurobiol. Dis.) vol. 15, pages 601-609, 2004]. It has also been reported that activation of CB2 suppresses progression of the disease in mutant superoxide dismutase overexpression mouse, which is an animal model of ALS [non-patent document 15: European Journal of Pharmacology (Eur. J. Pharmacol.), vol. 542, pages 100-105, 2006]. In addition, it has been reported that brain inflammation in MAGL-deficient mouse is suppressed by decreasing arachidonic acid, which is a product of MAGL in vivo[non-patent document 13: Science, vol. 334, pages 809-813, 2011]. Therefore, an MAGL inhibitor is promising as a new therapeutic drug for ALS.

Huntington's disease which is one of the neurodegenerative diseases is a disease wherein a neurological function is lost by nerve cell death and brain inflammation due to polyglutamine aggregation. It has been reported that activation of CB2 suppresses brain inflammation and shows a neuroprotective action in R6/2 mouse which is an animal model of Huntington's disease [non-patent document 16: Brain, vol. 132, pages 3152-3164, 2009]. In addition, it has been reported that brain inflammation is suppressed by decreasing arachidonic acid, which is a resultant product of MAGL, in MAGL deficient mouse [non-patent document 13: Science, vol. 334, pages 809-813, 2011]. Therefore, an MAGL inhibitor is promising as a new therapeutic drug for Huntington's disease.

2-AG, which is a substrate of MAGL, has been reported to suppress progression of the disease state in an autoimmune encephalomyelitis model, i.e., an animal model of multiple sclerosis which is one of the central demyelination diseases [non-patent document 17: Brain Research (Brain Res.), vol. 1390, pages 126-141, 2011]. In addition, it has been reported that brain inflammation is suppressed in MAGL deficient mouse by decreasing arachidonic acid, which is a resultant product of MAGL [non-patent document 13: Science, vol. 334, pages 809-813, 2011]. Therefore, an MAGL inhibitor is promising as a new therapeutic drug for multiple sclerosis.

Traumatic brain injury (TBI) is a condition exerting an extremely harmful influence on the health of individuals, and no effective treatment exists at present. 2-AG, which is a substrate of MAGL, has been reported to have a protective action against nerve cell death in a closed head injury animal model [non-patent document 18: Nature, vol. 413, pages 527-531, 2001]. Therefore, an MAGL inhibitor is promising as a new therapeutic or prophylactic drug for traumatic brain injury.

Glaucoma most often causes loss of eyesight, and is considered a serious social problem. 2-AG, which is a substrate of MAGL, has been reported to activate aqueous outflow in an intraocular perfusion model [non-patent document 19: Experimental Eye Research (Exp. Eye Res.), vol. 87, pages 106-114, 2008]. Therefore, an MAGL inhibitor is promising as a new therapeutic or prophylactic drug for glaucoma.

Anxiety disorder is a mental disease that occurs highly frequently, and greatly influences the quality of life. 2-AG, which is a substrate of MAGL, has been reported to show an anti-anxiety action in an elevated plus maze test, which is an effective test system of anxiety disorder [non-patent document 20: Behavioural Brain Research (Behav. Brain Res.), vol. 252, pages 10-17, 2013]. Therefore, an MAGL inhibitor is promising as a new therapeutic drug for anxiety disorders.

2-AG, which is a substrate of MAGL, has been reported to show an antinociceptive effect in a formalin test [non-patent document 21: British Journal of Pharmacology, vol. 150, pages 693-701, 2007]. In addition, 2-AG has been reported to show effect in a mechanical hyperalgesia test which is a carcinomatous pain model [non-patent document 22: Pharmacological Research (Pharmacol. Res.), vol. 64, pages 60-67, 2011]. Therefore, an MAGL inhibitor is promising as a new therapeutic drug for inflammatory pain and nervous pain.

Epilepsy greatly influences daily life. It is known that brain inflammation has been induced in the hippocampus of temporal lobe epilepsy patients, and brain inflammation accompanied by activation of glial cells is involved in convulsive attack [non-patent document 23: Nature Medicine (Nature Med.), vol. 16, pages 413-419, 2010]. 2-AG, which is a substrate of MAGL, has a suppressive action on pentylenetetrazole-induced convulsive attack, which is an acute convulsion model [non-patent document 24: Neurochemical Research (Neurochem. Res.), vol. 36, pages 1520-1525, 2011]. Therefore, an MAGL inhibitor is promising as a new therapeutic drug for epilepsy.

Depression is a disease that occurs highly frequently in the modern society, and greatly influences the quality of life. 2-AG, which is a substrate of MAGL, has been reported to show an anti-depression action on chronical stress model which is an effective test system of depression [non-patent document 25: Neuropsychopharmacology, vol. 39, pages 1763-1776, 2014]. Therefore, an MAGL inhibitor is promising as a new therapeutic drug for depression.

Migraine is a disease that occurs highly frequently in the modern society, and greatly influences the quality of life. One of the factors that develop migraine is brain inflammation. Activation of CB2 has been reported to have an analgesic action in nitroglycerin-administered rat, which is an effective test system of migraine [non-patent document 26: Journal of Headache and Pain, vol. 15, No. 14, 2014]. Therefore, an MAGL inhibitor is promising as a new therapeutic drug for migraine.

Cerebral edema is a disease developed in association with various encephalopathies. One of the causes of cerebral edema is collapse of blood-brain barrier. Arachidonic acid and eicosanoids are known to collapse blood-brain barrier [non-patent document 27: Brain Research, vol. 1298, pages 13-23, 2009]. An inhibitor that suppresses the action of MAGL decreases production of arachidonic acid by MAGL. Therefore, an MAGL inhibitor is promising as a new therapeutic drug for cerebral edema.

Cerebral ischemia is one factor causing the onset of cerebral infarction. 2-AG, which is a substrate of MAGL, has been reported to have a brain protective action in a test system effective for cerebral ischemia [non-patent document 28: Brain Research, vol. 1474, pages 91-99, 2012]. Therefore, an MAGL inhibitor is promising as a new therapeutic drug for cerebral ischemia.

As heterocyclic compounds, the following compounds are known. Patent Document 1 describes that a compound represented by the following formula (I):

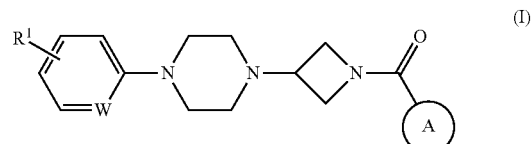

wherein each symbol is as defined in Patent Document 1, is a MAGL inhibitor, and useful for the treatment of pain and the like.

Patent Document 2 describes that a compound represented by the following formula (I):

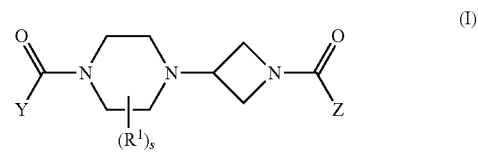

wherein each symbol is as defined in Patent Document 2, is a MAGL inhibitor, and useful for the treatment of pain and the like.

Patent Document 3 describes that a compound represented by the following formula (I):

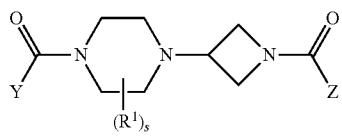

wherein each symbol is as defined in Patent Document 3, is a MAGL inhibitor, and useful for the treatment of pain and the like.

Patent Document 4 describes that a compound represented by the following formula (I):

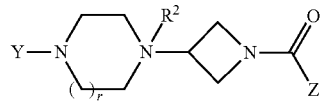

wherein each symbol is as defined in Patent Document 4, is a MAGL inhibitor, and useful for the treatment of pain and the like.

Patent Document 5 describes that a compound represented by the following formula:

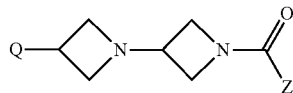

wherein each symbol is as defined in Patent Document 5, is useful as a MAGL inhibitor.

Patent Document 6 describes that a compound represented by the following formula:

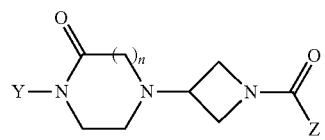

wherein each symbol is as defined in Patent Document 6, and a compound represented by the following formula:

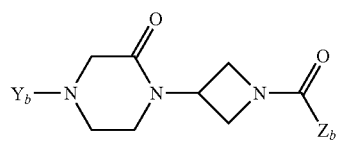

wherein each symbol is as defined in Patent Document 6, are useful as a MAGL inhibitor.

Patent Document 7 describes that a compound represented by the following formula:

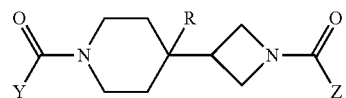

wherein each symbol is as defined in Patent Document 7, is useful as a MAGL inhibitor.

Patent Document 8 describes that a compound represented by the following formula (I):

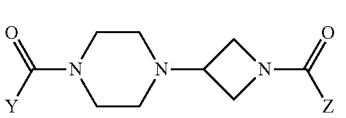

wherein each symbol is as defined in Patent Document 8, is an MAGL inhibitor, and useful for the treatment, improvement or prophylaxis of metabolic diseases (obesity, diabetes).

Patent Document 9 describes that a compound represented by the following formula (I):

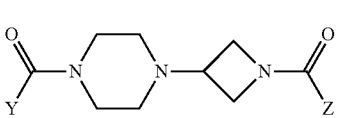

wherein each symbol is as defined in Patent Document 9, is an MAGL inhibitor, and useful for the treatment, improvement or prophylaxis of metabolic diseases (obesity, diabetes).

Patent Document 10 describes that a compound represented by the following formula (I):

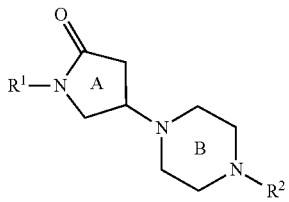

wherein each symbol is as defined in Patent Document 10, is an MAGL inhibitor, and useful for the treatment, improvement or prophylaxis of neurodegenerative diseases, anxiety disorder, pain and epilepsy.

Patent Document 11 describes that a compound represented by the following formula (I):

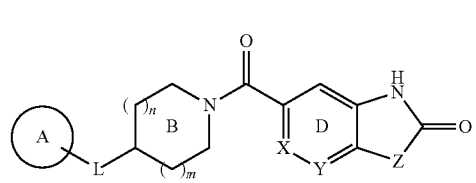

wherein each symbol is as defined in Patent Document 11, is an MAGL inhibitor, and useful for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, nervous pain etc.), epilepsy, depression and the like.

Patent Document 12 describes that a compound represented by the following formula (I):

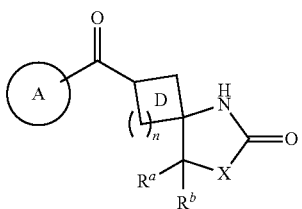

(I)

wherein each symbol is as defined in Patent Document 12, is an MAGL inhibitor, and useful for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, nervous pain etc.), epilepsy, depression and the like.

Patent Document 13 describes that a compound represented by the following formula (I):

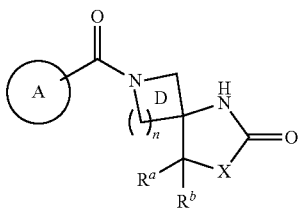

(I)

wherein each symbol is as defined in Patent Document 13, is an MAGL inhibitor, and useful for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, nervous pain etc.), epilepsy, depression and the like.

DOCUMENT LIST

Patent Document

Patent Document 1: WO 2010/124122
Patent Document 2: WO 2010/124082
Patent Document 3: WO 2010/124086
Patent Document 4: WO 2010/124121
Patent Document 5: WO 2012/030907
Patent Document 6: WO 2012/044613
Patent Document 7: WO 2012/054716
Patent Document 8: WO 2013/049289
Patent Document 9: WO 2013/049293
Patent Document 10: WO 2015/099196
Patent Document 11: WO 2016/158956
Patent Document 12: WO 2017/171100
Patent Document 13: WO 2017/170830

Non-Patent Document

Non-Patent document 1: Science, vol. 294, pages 1871-1875, 2001
Non-Patent document 2: Molecular Neurobiology (Mol. Neurobiol), vol. 41, pages 115-128, 2010
Non-Patent document 3: Neuron, vol. 53, pages 337-351, 2007
Non-Patent document 4: Nature Reviews Neurology (Nat. Rev. Neurol.), vol. 6, pages 193-201, 2010
Non-Patent document 5: Chemistry and Physics of Lipids (Chem phys Lipids) vol. 121, pages 149-158, 2002
Non-Patent document 6: Cell Report (Cell Rep.), vol. 1, page 617-623, 2012
Non-Patent document 7: Biochemical Pharmacology (Biochem. Pharmcol.) vol. 50, 83-90, 1995
Non-Patent document 8: Molecular Pharmacology (Mol. Pharmacol.), vol. 34, pages 605-613, 1988
Non-Patent document 9: Neuroscience Letters (Neurosci. Lett.), vol. 396, pages 113-116, 2006
Non-Patent document 10: Journal of Alzheimer's Disease (J. Alzheimers. Dis.), vol. 30, pages 439-459, 2012 Non-Patent document 11: Neuroscience, vol. 178, pages 159-168, 2011
Non-Patent document 12: Annals of Neurology (Ann. Neurol.) vol. 57, pages 168-175, 2005
Non-Patent document 13: Science, vol. 334, pages 809-813, 2011
Non-Patent document 14: Neurobiology of Disease (Neurobiol. Dis.) vol. 15, pages 601-609, 2004
Non-Patent document 15: European Journal of Pharmacology (Eur. J. Pharmacol.), vol. 542, pages 100-105, 2006
Non-Patent document 16: Brain, vol. 132, pages 3152-3164, 2009
Non-Patent document 17: Brain Research (Brain Res.), vol. 1390, pages 126-141, 2011
Non-Patent document 18: Nature, vol. 413, pages 527-531, 2001
Non-Patent document 19: Experimental Eye Research (Exp. Eye Res.), vol. 87, pages 106-114, 2008
Non-Patent document 20: Behavioural Brain Research (Behav. Brain Res.), vol. 252, pages 10-17, 2013
Non-Patent document 21: British Journal of Pharmacology, vol. 150, pages 693-701, 2007
Non-Patent document 22: Pharmacological Research (Pharmacol. Res.), vol. 64, pages 60-67, 2011
Non-Patent document 23: Nature Medicine (Nature Med.), vol. 16, pages 413-419, 2010
Non-Patent document 24: Neurochemical Research (Neurochem. Res.), vol. 36, pages 1520-1525, 2011
Non-Patent document 25: Neuropsychopharmacology, vol. 39, pages 1763-1776, 2014
Non-Patent document 26: Journal of Headache and Pain, vol. 15, No. 14, 2014
Non-Patent document 27: Brain Research, vol. 1298, pages 13-23, 2009
Non-Patent document 28: Brain Research, vol. 1474, pages 91-99, 2012

SUMMARY OF THE INVENTION

Problems to be Solved by the Invention

An object of the present invention is to provide a compound having an MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like.

Means of Solving the Problems

The present inventors have conducted intensive studies in an attempt to solve the above-mentioned problems and found that a compound represented by the following formula (I) has an MAGL inhibitory action, and therefore, is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like, which resulted in the completion of the present invention.

Accordingly, the present invention provides the following.

[1] A compound represented by the formula (I):

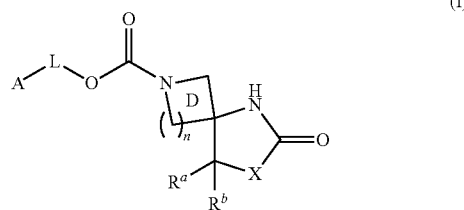

wherein
A is an optionally substituted saturated cyclic group,
L is a bond or a $C_{1-3}$ alkylene group optionally substituted by halogen atom(s),
Ring D is a ring optionally further substituted by $C_{1-6}$ alkyl group(s) optionally substituted by halogen atom(s),
n is 1 or 2,
X is —O—, —$CR^1R^2$— or —$NR^3$—,
$R^a$ and $R^b$ are each independently a hydrogen atom or a $C_{1-6}$ alkyl group optionally substituted by halogen atom(s), and
$R^1$, $R^2$ and $R^3$ are each independently a hydrogen atom or a substituent,
or a salt thereof (hereinafter sometimes to be referred to as compound (I)).
[2] The compound or salt of the above-mentioned [1], wherein A is a $C_{3-10}$ cycloalkyl group substituted by 1 to 3 substituents selected from
  (a) a $C_{6-14}$ aryloxy group optionally substituted by 1 to 4 substituents selected from
    (i) a halogen atom, and
    (ii) an optionally halogenated $C_{1-6}$ alkyl group,
  (b) a $C_{6-14}$ aryloxy-$C_{1-6}$ alkyl group optionally substituted by 1 to 4 substituents selected from
    (i) a halogen atom, and
    (ii) an optionally halogenated $C_{1-6}$ alkyl group,
  (c) a $C_{7-16}$ aralkyloxy group optionally substituted by 1 to 4 substituents selected from
    (i) a halogen atom, and
    (ii) an optionally halogenated $C_{1-6}$ alkyl group, and
  (d) a $C_{7-16}$ aralkyloxy-$C_{1-6}$ alkyl group optionally substituted by 1 to 4 substituents selected from
    (i) a halogen atom, and
    (ii) an optionally halogenated $C_{1-6}$ alkyl group, and optionally further substituted by 1 to 3 $C_{1-6}$ alkyl groups;
L is bond or a $C_{1-3}$ alkylene group;
Ring D is a 4- or 5-membered nitrogen-containing heterocycle;
n is 1 or 2;
X is —O— or —$CH_2$—; and
$R^a$ and $R^b$ are both hydrogen atoms.
[3] The compound or salt of the above-mentioned [1], wherein A is a cyclobutyl group substituted by one substituent selected from
  (a) a phenoxy group substituted by 3 halogen atoms, and
  (b) a phenoxymethyl group substituted by 3 halogen atoms;
L is bond;
Ring D is an azetidine ring;
n is 1;
X is —O—; and
$R^a$ and $R^b$ are both hydrogen atoms.
[4] cis-3-((2,3,4-Trifluorophenoxy)methyl)cyclobutyl 6-oxo-7-oxa-2,5-diazaspiro[3.4]octane-2-carboxylate or a salt thereof.
[5] cis-3-((2,4,6-Trifluorophenoxy)methyl)cyclobutyl 6-oxo-7-oxa-2,5-diazaspiro[3.4]octane-2-carboxylate or a salt thereof.
[6] cis-3-(2,4,6-Trifluorophenoxy)cyclobutyl 6-oxo-7-oxa-2,5-diazaspiro[3.4]octane-2-carboxylate or a salt thereof.
[7] A medicament comprising the compound or salt of the above-mentioned [1].
[8] The medicament of the above-mentioned [7], which is a monoacylglycerol lipase inhibitor.
[9] The medicament of the above-mentioned [7], which is an agent for the prophylaxis or treatment of Alzheimer's disease, Parkinson's disease, Huntington's disease, amyotrophic lateral sclerosis, multiple sclerosis, anxiety disorder, pain, epilepsy or depression.
[10] A method of inhibiting monoacylglycerol lipase in a mammal, which comprises administering an effective amount of the compound or salt of the above-mentioned [1] to the mammal.
[11] A method for the prophylaxis or treatment of Alzheimer's disease, Parkinson's disease, Huntington's disease, amyotrophic lateral sclerosis, multiple sclerosis, anxiety disorder, pain, epilepsy or depression in a mammal, which comprises administering an effective amount of the compound or salt of the above-mentioned [1] to the mammal.
[12] The compound or salt of the above-mentioned [1] for use in the prophylaxis or treatment of Alzheimer's disease, Parkinson's disease, Huntington's disease, amyotrophic lateral sclerosis, multiple sclerosis, anxiety disorder, pain, epilepsy or depression.
[13] Use of the compound or salt of the above-mentioned [1] for the manufacture of an agent for the prophylaxis or treatment of Alzheimer's disease, Parkinson's disease, Huntington's disease, amyotrophic lateral sclerosis, multiple sclerosis, anxiety disorder, pain, epilepsy or depression.

Effect of the Invention

According to the present invention, a compound having a superior MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated C$_{1-6}$ alkylsulfonyl group" include a C$_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "C$_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a C$_{1-6}$ alkyl group, a C$_{2-6}$ alkenyl group, a C$_{2-6}$ alkynyl group, a C$_{3-10}$ cycloalkyl group, a C$_{3-10}$ cycloalkenyl group, a C$_{6-14}$ aryl group and a C$_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group (e.g., phenoxy, naphthoxy),
(8) a C$_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C$_{1-6}$ alkyl-carbonyloxy group (e.g., acetoxy, propanoyloxy),
(12) a C$_{6-14}$ aryl-carbonyloxy group (e.g., benzoyloxy, 1-naphthoyloxy, 2-naphthoyloxy),
(13) a C$_{1-6}$ alkoxy-carbonyloxy group (e.g., methoxycarbonyloxy, ethoxycarbonyloxy, propoxycarbonyloxy, butoxycarbonyloxy),
(14) a mono- or di-C$_{1-6}$ alkyl-carbamoyloxy group (e.g., methylcarbamoyloxy, ethylcarbamoyloxy, dimethylcarbamoyloxy, diethylcarbamoyloxy),
(15) a C$_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C$_{1-6}$ alkylsulfonyloxy group (e.g., methylsulfonyloxy, trifluoromethylsulfonyloxy),
(19) a C$_{6-14}$ arylsulfonyloxy group optionally substituted by a C$_{1-6}$ alkyl group (e.g., phenylsulfonyloxy, toluenesulfonyloxy),
(20) an optionally halogenated C$_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C$_{1-6}$ alkyl-carbonyl group,
(26) a C$_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a C$_{1-6}$ alkoxy-carbonyl group,
(30) a C$_{6-14}$ aryloxy-carbonyl group (e.g., phenyloxycarbonyl, 1-naphthyloxycarbonyl, 2-naphthyloxycarbonyl),
(31) a C$_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-C$_{1-6}$ alkyl-carbamoyl group,
(35) a C$_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated C$_{1-6}$ alkylsulfonyl group,
(39) a C$_{6-14}$ arylsulfonyl group,
(40) a 5- to 14-membered aromatic heterocyclylsulfonyl group (e.g., pyridylsulfonyl, thienylsulfonyl),
(41) an optionally halogenated C$_{1-6}$ alkylsulfinyl group,
(42) a C$_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-C$_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C$_{6-14}$ arylamino group (e.g., phenylamino),
(47) a 5- to 14-membered aromatic heterocyclylamino group (e.g., pyridylamino),
(48) a C$_{7-16}$ aralkylamino group (e.g., benzylamino),
(49) a formylamino group,
(50) a C$_{1-6}$ alkyl-carbonylamino group (e.g., acetylamino, propanoylamino, butanoylamino),
(51) a (C$_{1-6}$ alkyl) (C$_{1-6}$ alkyl-carbonyl) amino group (e.g., N-acetyl-N-methylamino),
(52) a C$_{6-14}$ aryl-carbonylamino group (e.g., phenylcarbonylamino, naphthylcarbonylamino),
(53) a C$_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a C$_{7-16}$ aralkyloxy-carbonylamino group (e.g., benzyloxycarbonylamino),
(55) a C$_{1-6}$ alkylsulfonylamino group (e.g., methylsulfonylamino, ethylsulfonylamino),
(56) a C$_{6-14}$ arylsulfonylamino group optionally substituted by a C$_{1-6}$ alkyl group (e.g., phenylsulfonylamino, toluenesulfonylamino),
(57) an optionally halogenated C$_{1-6}$ alkyl group,
(58) a C$_{2-6}$ alkenyl group,
(59) a C$_{2-6}$ alkynyl group,
(60) a C$_{3-10}$ cycloalkyl group,
(61) a C$_{3-10}$ cycloalkenyl group, and
(62) a C$_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl; indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-6}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_6$-14 aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{L-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{L}$-6 alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{5-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocylyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl (dimethyl)silyl).

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained in detail in the following.

A is an optionally substituted saturated cyclic group.

Examples of the "saturated cyclic group" of the "optionally substituted saturated cyclic group" represented by A include a $C_{3-10}$ cycloalkyl group and a saturated heterocyclic group. Examples of the "saturated heterocyclic group" include saturated groups, from among the "non-aromatic heterocyclic group", and specific examples thereof include 3- to 8-membered saturated monocyclic non-aromatic heterocyclic groups such as aziridinyl, azetidinyl, pyrrolidinyl, piperidyl, piperazinyl, morpholinyl, thiomorpholinyl, imidazolidinyl, oxazolidinyl, pyrazolidinyl, thiazolidinyl, tetrahydroisothiazolyl, tetrahydroisoxazolyl, tetrahydropyrimidinyl, tetrahydropyridazinyl, azepanyl, diazepanyl, azocanyl, diazocanyl, oxiranyl, oxetanyl, tetrahydrofuryl, tetrahydropyranyl, thiiranyl, thietanyl, tetrahydrothienyl, tetrahydrothiopyranyl and the like.

The "saturated cyclic group" of the "optionally substituted saturated cyclic group" represented by A is preferably a $C_{3-10}$ cycloalkyl group, more preferably a $C_{3-6}$ cycloalkyl group (e.g., cyclobutyl, cyclohexyl), further more preferably a cyclobutyl group or a cyclohexyl group, particularly preferably a cyclobutyl group.

The "saturated cyclic group" of the "optionally substituted saturated cyclic group" represented by A is optionally substituted, for example, by substituent(s) selected from the above-mentioned Substituent group A. The number of the substituents is, for example, 1 to 3. When the number of the substituents is 2 or more, the respective substituents may be the same or different. In addition, Substituent group A is optionally further substituted by substituent(s) selected from the above-mentioned Substituent group A. The number of the substituents is, for example, 1 to 3. When the number of the substituents is 2 or more, the respective substituents may be the same or different.

Preferable Examples of the Substituent Include (a) an optionally substituted $C_{6-14}$ aryloxy group (e.g., phenoxy),
(b) an optionally substituted $C_{6-14}$ aryloxy-$C_{1-6}$ alkyl group (preferably a $C_{6-14}$ aryloxymethyl group (e.g., phenoxymethyl)),
(c) an optionally substituted $C_{7-16}$ aralkyloxy group (e.g., benzyloxy),
(d) an optionally substituted $C_{7-16}$ aralkyloxy-$C_{1-6}$ alkyl group (preferably a $C_{7-16}$ aralkyloxymethyl group (e.g., benzyloxymethyl)), and
(e) a $C_{1-6}$ alkyl group (e.g., methyl).

More preferable examples of the substituent include
(a) an optionally substituted $C_{6-14}$ aryloxy group (e.g., phenoxy),
(b) an optionally substituted $C_{6-14}$ aryloxy-$C_{1-6}$ alkyl group (preferably a $C_{6-14}$ aryloxymethyl group (e.g., phenoxymethyl)), and
(c) a $C_{1-6}$ alkyl group (e.g., methyl).

Particular preferable examples of the substituent include
(a) an optionally substituted $C_{6-14}$ aryloxy group (e.g., phenoxy), and
(b) an optionally substituted $C_{6-14}$ aryloxy-$C_{1-6}$ alkyl group (preferably a $C_{6-14}$ aryloxymethyl group (e.g., phenoxymethyl)).

Preferable examples of the substituent of the "optionally substituted $C_{6-14}$ aryloxy group", "optionally substituted $C_{6-14}$ aryloxy-$C_{1-6}$ alkyl group", "optionally substituted $C_{7-16}$ aralkyloxy group" and "optionally substituted $C_{7-16}$ aralkyloxy-$C_{1-6}$ alkyl group" include a halogen atom (e.g., a fluorine atom, a chlorine atom) and an optionally halogenated $C_{1-6}$ alkyl group (e.g., methyl, trifluoromethyl).

A is preferably an optionally substituted $C_{3-10}$ cycloalkyl group (preferably a $C_{3-6}$ cycloalkyl group (e.g., cyclobutyl, cyclohexyl), particularly preferably cyclobutyl).

A is more preferably a $C_{3-10}$ cycloalkyl group (preferably a $C_{3-6}$ cycloalkyl group (e.g., cyclobutyl, cyclohexyl), particularly preferably cyclobutyl) substituted by 1 to 3 (preferably 1) substituents selected from (a) an optionally substituted $C_{6-14}$ aryloxy group (e.g., phenoxy),
(b) an optionally substituted $C_{6-14}$ aryloxy-$C_{1-6}$ alkyl group (preferably a $C_{6-14}$ aryloxymethyl group (e.g., phenoxymethyl)),
(c) an optionally substituted $C_{7-16}$ aralkyloxy group (e.g., benzyloxy), and
(d) an optionally substituted $C_{7-16}$ aralkyloxy-$C_{1-6}$ alkyl group (preferably a $C_{7-16}$ aralkyloxymethyl group (e.g., benzyloxymethyl)), and
optionally further substituted by 1 to 3 (preferably 1) substituents selected from
(e) a $C_{1-6}$ alkyl group (e.g., methyl).

A is further more preferably a $C_{3-10}$ cycloalkyl group (preferably a $C_{3-6}$ cycloalkyl group (e.g., cyclobutyl, cyclohexyl), particularly preferably cyclobutyl) substituted by 1 to 3 (preferably 1) substituents selected from (a) a $C_{6-14}$ aryloxy group (e.g., phenoxy) optionally substituted by 1 to 4 (preferably 1 to 3, more preferably 2 or 3) substituents selected from
  (i) a halogen atom (e.g., a fluorine atom, a chlorine atom), and
  (ii) an optionally halogenated $C_{1-6}$ alkyl group (e.g., methyl, trifluoromethyl),
(b) a $C_{6-14}$ aryloxy-$C_{1-6}$ alkyl group (preferably a $C_{6-14}$ aryloxymethyl group (e.g., phenoxymethyl)) optionally substituted by 1 to 4 (preferably 1 to 3, more preferably 2 or 3) substituents selected from
  (i) a halogen atom (e.g., a fluorine atom, a chlorine atom), and
  (ii) an optionally halogenated $C_{1-6}$ alkyl group (e.g., methyl, trifluoromethyl),
(c) a $C_{7-16}$ aralkyloxy group (e.g., benzyloxy) optionally substituted by 1 to 4 (preferably 1 to 3, more preferably 2 or 3) substituents selected from
  (i) a halogen atom (e.g., a fluorine atom, a chlorine atom), and
  (ii) an optionally halogenated $C_{1-6}$ alkyl group (e.g., methyl, trifluoromethyl), and
(d) a $C_{7-16}$ aralkyloxy-$C_{1-6}$ alkyl group (preferably a $C_{7-16}$ aralkyloxymethyl group (e.g., benzyloxymethyl)) optionally substituted by 1 to 4 (preferably 1 to 3, more preferably 2 or 3) substituents selected from
  (i) a halogen atom (e.g., a fluorine atom, a chlorine atom), and
  (ii) an optionally halogenated $C_{1-6}$ alkyl group (e.g., methyl, trifluoromethyl), and optionally further substituted by 1 to 3 (preferably 1) $C_{1-6}$ alkyl groups (e.g., methyl).

A is still more preferably
(1) a cyclobutyl group substituted by 1 to 3 (preferably 1) substituents selected from
  (a) a phenoxy group optionally substituted by 1 to 4 (preferably 1 to 3, more preferably 2 or 3) substituents selected from (i) a halogen atom (e.g., a fluorine atom, a chlorine atom), and
(ii) an optionally halogenated $C_{1-6}$ alkyl group (e.g., methyl, trifluoromethyl),
(b) a phenoxymethyl group optionally substituted by 1 to 4 (preferably 1 to 3, more preferably 2 or 3) substituents selected from
(i) a halogen atom (e.g., a fluorine atom, a chlorine atom), and
(ii) an optionally halogenated $C_{1-6}$ alkyl group (e.g., methyl, trifluoromethyl),
(c) a benzyloxy group optionally substituted by 1 to 4 (preferably 1 to 3, more preferably 2 or 3) substituents selected from
(i) a halogen atom (e.g., a fluorine atom, a chlorine atom), and
(ii) an optionally halogenated $C_{1-6}$ alkyl group (e.g., methyl, trifluoromethyl), and
(d) a benzyloxymethyl group optionally substituted by 1 to 4 (preferably 1 to 3, more preferably 2 or 3) substituents selected from
(i) a halogen atom (e.g., a fluorine atom, a chlorine atom), and
(ii) an optionally halogenated $C_{1-6}$ alkyl group (e.g., methyl, trifluoromethyl), and
optionally further substituted by 1 to 3 (preferably 1) $C_{1-6}$ alkyl groups (e.g., methyl), or
(2) a cyclohexyl group substituted by 1 to 3 (preferably 1) substituents selected from
(a) a phenoxy group optionally substituted by 1 to 4 (preferably 1 to 3, more preferably 2 or 3) substituents selected from
(i) a halogen atom (e.g., a fluorine atom), and
(ii) an optionally halogenated $C_{1-6}$ alkyl group (e.g., trifluoromethyl).

A is even more preferably a cyclobutyl group substituted by one substituent selected from
(a) a phenoxy group substituted by 2 or 3 substituents selected from
(i) a halogen atom (e.g., a fluorine atom, a chlorine atom), and
(ii) a $C_{1-6}$ alkyl group (e.g., methyl), and
(b) a phenoxymethyl group substituted by 2 or 3 substituents selected from
(i) a halogen atom (e.g., a fluorine atom, a chlorine atom), and
(ii) a $C_{1-6}$ alkyl group (e.g., methyl), and
optionally further substituted by 1 to 3 (preferably 1) $C_{1-6}$ alkyl groups (e.g., methyl).

A is particularly preferably a cyclobutyl group substituted by one substituent selected from
(a) a phenoxy group substituted by 3 halogen atoms (e.g., a fluorine atom), and
(b) a phenoxymethyl group substituted by 3 halogen atoms (e.g., a fluorine atom).

As another embodiment, when A is a substituted cyclobutyl group, one substituent Y selected from
(a) an optionally substituted $C_{6-14}$ aryloxy group (e.g., phenoxy),
(b) an optionally substituted $C_{6-14}$ aryloxy-$C_{1-6}$ alkyl group (preferably a $C_{6-14}$ aryloxymethyl group (e.g., phenoxymethyl)),
(c) an optionally substituted $C_{7-16}$ aralkyloxy group (e.g., benzyloxy), and
(d) an optionally substituted $C_{7-16}$ aralkyloxy-$C_{1-6}$ alkyl group (preferably a $C_{7-16}$ aralkyloxymethyl group (e.g., benzyloxymethyl))

is preferably substituted at the 3-position on the cyclobutane ring, as shown in the following partial structure.

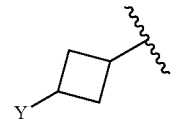

In this case, the cyclobutyl group is optionally further substituted by 1 to 3 (preferably 1) substituents selected from
(e) a $C_{1-6}$ alkyl group (e.g., methyl).

The above-mentioned partial structure is preferably

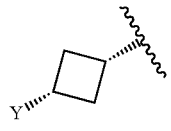

L is a bond or a $C_{1-3}$ alkylene group optionally substituted by halogen atom(s).

Examples of the "$C_{1-3}$ alkylene group" of the "optionally substituted $C_{1-3}$ alkylene group" represented by L include —$CH_2$—, —$(CH_2)_2$—, —$(CH_2)_3$—, —$CH(CH_3)$—, —$C(CH_3)_2$—, —$CH(C_2H_5)$—, —$CH_2$—$CH(CH_3)$—, —$CH(CH_3)$—$CH_2$— and the like.

L is preferably a bond or a $C_{1-3}$ alkylene group (e.g., —$CH_2$—)

L is preferably a bond.

Ring D is a ring optionally further substituted by $C_{1-6}$ alkyl group(s) optionally substituted by halogen atom(s).

Examples of the "ring" of the "ring optionally further substituted by $C_{1-6}$ alkyl group(s) optionally substituted by halogen atom(s)" represented by Ring D include a 4- or 5-membered nitrogen-containing heterocycle and the like. Examples of the "4- or 5-membered nitrogen-containing heterocycle" include 4- or 5-membered rings containing at least one nitrogen atom as a ring constituting atom, from among the "heterocycle", and specific examples thereof include azetidine, pyrrolidine and the like.

The "ring" of the "ring optionally further substituted by $C_{1-6}$ alkyl group(s) optionally substituted by halogen atom(s)" represented by Ring D is preferably a 4- or 5-membered nitrogen-containing heterocycle (e.g., azetidine, pyrrolidine), more preferably an azetidine ring or a pyrrolidine ring, particularly preferably an azetidine ring.

Ring D is preferably a 4- or 5-membered nitrogen-containing heterocycle (e.g., azetidine, pyrrolidine) optionally further substituted by $C_{1-6}$ alkyl group(s) optionally substituted by halogen atom(s).

Ring D is more preferably a 4- or 5-membered nitrogen-containing heterocycle (e.g., azetidine, pyrrolidine).

Ring D is further more preferably an azetidine ring or a pyrrolidine ring.

Ring D is particularly preferably an azetidine ring.

n is 1 or 2.

n is preferably 1.

X is —O—, —$CR^1R^2$— or —$NR^3$—.

$R^1$, $R^2$ and $R^3$ are each independently a hydrogen atom or a substituent. Examples of the "substituent" include substituent(s) selected from Substituent group A.

X is preferably —O— or —CR$^1$R$^2$—.
R$^1$ and R$^2$ are preferably both hydrogen atoms.
X is more preferably —O— or —CH$_2$—.
X is further more preferably —O—.
R$^a$ and R$^b$ are each independently a hydrogen atom or a C$_{1-6}$ alkyl group optionally substituted by halogen atom(s).
R$^a$ and R$^b$ is preferably both hydrogen atoms.
The combination of Ring D, n, X, R$^a$ and R$^b$ is preferably
Ring D is a 4- or 5-membered nitrogen-containing heterocycle (e.g., azetidine, pyrrolidine);
n is 1 or 2;
X is —O— or —CH$_2$—; and
R$^a$ and R$^b$ are both hydrogen atoms, more preferably
Ring D is an azetidine ring or a pyrrolidine ring;
n is 1 or 2;
X is —O— or —CH$_2$—; and
R$^a$ and R$^b$ are both hydrogen atoms,
particularly preferably
Ring D is an azetidine ring;
n is 1;
X is —O—; and
R$^a$ and R$^b$ are both hydrogen atoms.

Preferable examples of compound (I) include the following compounds.

[Compound A]
Compound (I) wherein
A is a C$_{3-10}$ cycloalkyl group (preferably a C$_{3-6}$ cycloalkyl group (e.g., cyclobutyl, cyclohexyl), particularly preferably cyclobutyl) substituted by 1 to 3 (preferably 1) substituents selected from
  (a) an optionally substituted C$_{6-14}$ aryloxy group (e.g., phenoxy),
  (b) an optionally substituted C$_{6-14}$ aryloxy-C$_{1-6}$ alkyl group (preferably a C$_{6-14}$ aryloxymethyl group (e.g., phenoxymethyl)),
  (c) an optionally substituted C$_{7-16}$ aralkyloxy group (e.g., benzyloxy), and
  (d) an optionally substituted C$_{7-16}$ aralkyloxy-C$_{1-6}$ alkyl group (preferably a C$_{7-16}$ aralkyloxymethyl group (e.g., benzyloxymethyl)), and
optionally further substituted by 1 to 3 (preferably 1) substituents selected from
  (e) a C$_{1-6}$ alkyl group (e.g., methyl);
L is a bond or a C$_{1-3}$ alkylene group optionally substituted by halogen atom(s);
Ring D is a 4- or 5-membered nitrogen-containing heterocycle (e.g., azetidine, pyrrolidine) optionally further substituted by C$_{1-6}$ alkyl group(s) optionally substituted by halogen atom(s);
n is 1 or 2;
X is —O— or —CR$^1$R$^2$—;
R$^1$ and R$^2$ are each independently a hydrogen atom or a substituent; and
R$^a$ and R$^b$ are each independently a hydrogen atom or a C$_{1-6}$ alkyl group optionally substituted by halogen atom(s).

[Compound B]
Compound (I) wherein
A is a C$_{3-10}$ cycloalkyl group (preferably a C$_{3-6}$ cycloalkyl group (e.g., cyclobutyl, cyclohexyl), particularly preferably cyclobutyl) substituted by 1 to 3 (preferably 1) substituents selected from
  (a) a C$_{6-14}$ aryloxy group (e.g., phenoxy) optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl),
  (b) a C$_{6-14}$ aryloxy-C$_{1-6}$ alkyl group (preferably a C$_{6-14}$ aryloxymethyl group (e.g., phenoxymethyl)) optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl),
  (c) a C$_{7-16}$ aralkyloxy group (e.g., benzyloxy) optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl), and
  (d) a C$_{7-16}$ aralkyloxy-C$_{1-6}$ alkyl group (preferably a C$_{7-16}$ aralkyloxymethyl group (e.g., benzyloxymethyl)) optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl), and
optionally further substituted by 1 to 3 (preferably 1) C$_{1-6}$ alkyl groups (e.g., methyl);
L is bond or a C$_{1-3}$ alkylene group (e.g., —CH$_2$—);
Ring D is a 4- or 5-membered nitrogen-containing heterocycle (e.g., azetidine, pyrrolidine);
n is 1 or 2;
X is —O— or —CH$_2$—; and
R$^a$ and R$^b$ are both hydrogen atoms.

[Compound C]
Compound (I) wherein
A is
(1) a cyclobutyl group
substituted by 1 to 3 (preferably 1) substituents selected from
  (a) a phenoxy group optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl),
  (b) a phenoxymethyl group optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl),
  (c) a benzyloxy group optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl), and
  (d) a benzyloxymethyl group optionally substituted by 1 to 4 (preferably 1 to 3, more preferably 2 or 3) substituents selected from
    (i) a halogen atom (e.g., a fluorine atom, a chlorine atom), and
    (ii) an optionally halogenated C$_{1-6}$ alkyl group (e.g., methyl, trifluoromethyl), and optionally further substituted by 1 to 3 (preferably 1) $C_{1-6}$ alkyl groups (e.g., methyl), or (2) a cyclohexyl group substituted by 1 to 3 (preferably 1) substituents selected from
- (a) a phenoxy group optionally substituted by 1 to 4 (preferably 1 to 3, more preferably 2 or 3) substituents selected from
  - (i) a halogen atom (e.g., a fluorine atom), and
  - (ii) an optionally halogenated $C_{1-6}$ alkyl group (e.g., trifluoromethyl);

L is bond or a $C_{1-3}$ alkylene group (e.g., —$CH_2$—);
Ring D is an azetidine ring or a pyrrolidine ring;
n is 1 or 2;
X is —O— or —$CH_2$—; and
$R^a$ and $R^b$ are both hydrogen atoms.

[Compound D]
Compound (I) wherein
A is a cyclobutyl group
substituted by one substituent selected from
- (a) a phenoxy group substituted by 2 or 3 substituents selected from
  - (i) a halogen atom (e.g., a fluorine atom, a chlorine atom), and
  - (ii) a $C_{1-6}$ alkyl group (e.g., methyl), and
- (b) a phenoxymethyl group substituted by 2 or 3 substituents selected from
  - (i) a halogen atom (e.g., a fluorine atom, a chlorine atom), and
  - (ii) a $C_{1-6}$ alkyl group (e.g., methyl), and optionally further substituted by 1 to 3 (preferably 1) $C_{1-6}$ alkyl groups (e.g., methyl);
L is bond;
Ring D is an azetidine ring;
n is 1;
X is —O—; and
$R^a$ and $R^b$ are both hydrogen atoms.

[Compound E]
Compound (I) wherein
A is a cyclobutyl group substituted by one substituent selected from
- (a) a phenoxy group substituted by 3 halogen atoms (e.g., a fluorine atom), and
- (b) a phenoxymethyl group substituted by 3 halogen atoms (e.g., a fluorine atom);

L is bond;
Ring D is an azetidine ring;
n is 1;
X is —O—; and
$R^a$ and $R^b$ are both hydrogen atoms.

Specific examples of compound (I) include the compounds of Examples 1 to 64.

Among them,
cis-3-((2,3,4-trifluorophenoxy)methyl)cyclobutyl 6-oxo-7-oxa-2,5-diazaspiro[3.4]octane-2-carboxylate (Example 16) or a salt thereof;
cis-3-((2,4,6-trifluorophenoxy)methyl)cyclobutyl 6-oxo-7-oxa-2,5-diazaspiro[3.4]octane-2-carboxylate (Example 18) or a salt thereof; and
cis-3-(2,4,6-trifluorophenoxy)cyclobutyl 6-oxo-7-oxa-2,5-diazaspiro[3.4]octane-2-carboxylate (Example 46) or a salt thereof
are preferable.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^2H$, $^3H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like.

Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine) nickel (0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, trifluoromethanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When carbonylation reaction is carried out in each step, examples of the reagent to be used include triphosgene, 1,1'-carbonylbis-1H-imidazole, diphosgene, phenyl chloroformate and the like.

Compound (I) can be synthesized according to the following schemes. Each symbol in the formulas of the schemes is as defined above, unless otherwise specified. $P^1$ is a "protecting group for an amino group". Examples of the "protecting group for an amino group" include tert-butoxycarbonyl group and the like, in addition to those exemplified as the above-mentioned protecting group for an amino group. $R^4$ is an optionally substituted $C_{1-6}$ alkyl group (e.g., methyl).

Compound (I) can be produced by subjecting compound (2) and compound (3) to a carbonylation reaction.

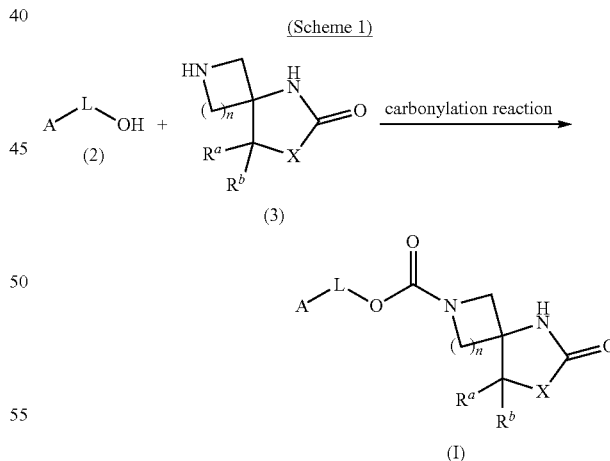

Moreover, when desired, compound (I) can be synthesized by performing deprotection reaction, acylation reaction, alkylation reaction, Mitsunobu reaction, hydrogenation reaction, oxidation reaction, reduction reaction, reaction of carbon chain extension, halogenation reaction, substituent exchange reaction, coupling reaction, nucleophilic addition reaction by a carbo anion, Grignard reaction, deoxofluorination reaction and the like singly or two or more thereof in combination.

Among compound (3) used in Reaction Scheme 1, compound (3-1), which is compound (3) wherein X is —O—, can be produced from compound (4) according to the following method.

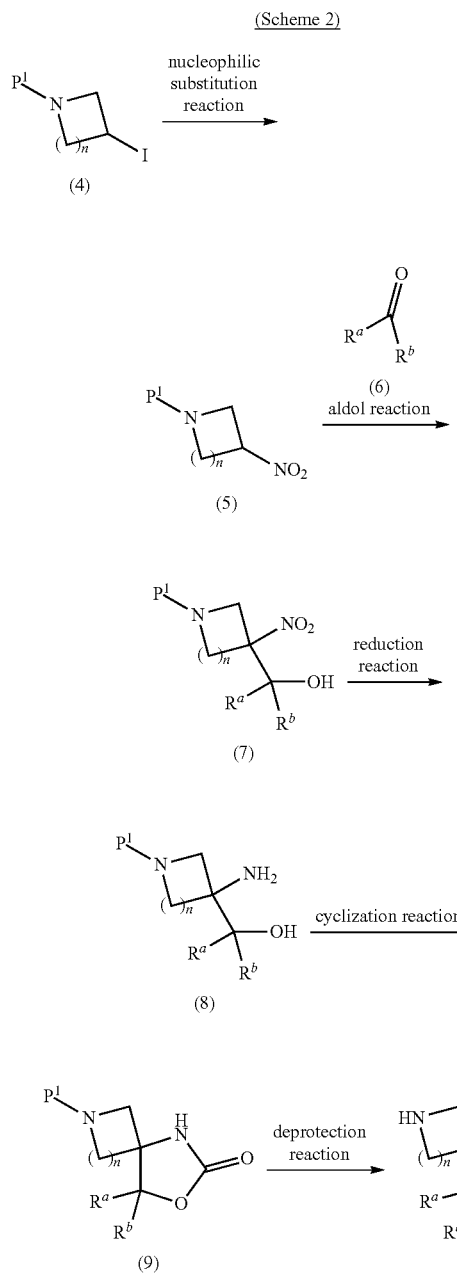

Compound (5) can be produced by subjecting compound (4) to a nucleophilic substitution reaction. Examples of the nucleophile include sodium nitrite and the like.

Compound (7) can be produced by subjecting compound (5) to an aldol reaction with compound (6) in the presence of a base. Examples of the base include triethylamine and the like.

Compound (8) can be produced by subjecting compound (7) to a reduction reaction.

Compound (9) can be produced by subjecting compound (8) to a cyclization reaction employing a carbonylation reaction, in the presence of a base. Examples of the base include triethylamine and the like.

Compound (3-1) can be produced by subjecting compound (9) to a deprotection reaction.

Among compound (3) used in Reaction Scheme 1, compound (3-2), which is compound (3) wherein X is —CH$_2$—, can be produced from compound (5) according to the following method.

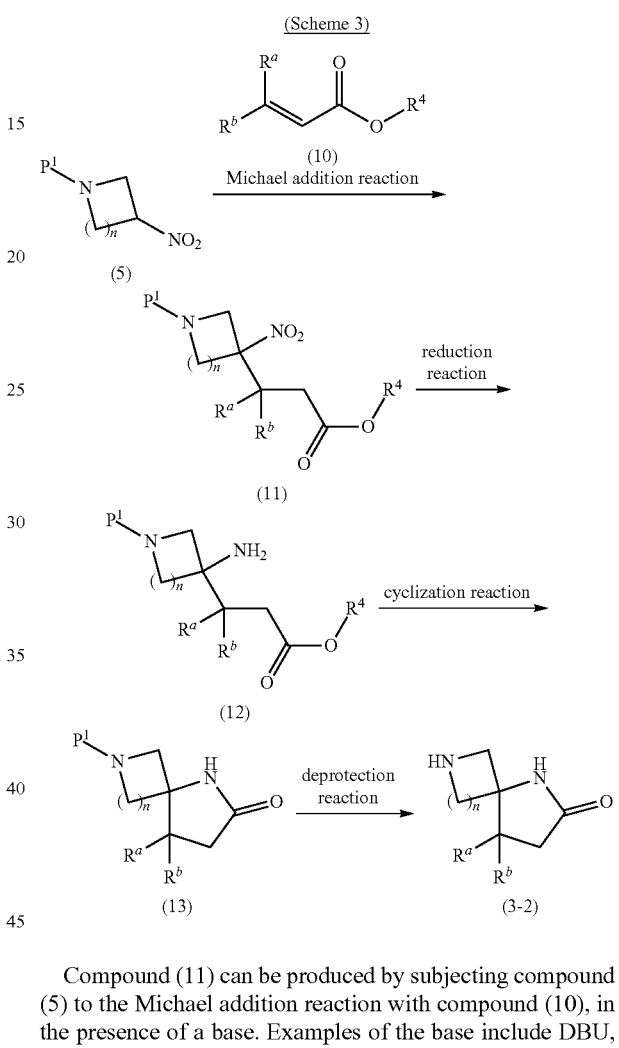

Compound (11) can be produced by subjecting compound (5) to the Michael addition reaction with compound (10), in the presence of a base. Examples of the base include DBU, potassium carbonate and the like.

Compound (12) can be produced by subjecting compound (11) to a reduction reaction. As a reaction condition, combination use of sodium borohydride and nickel (II) chloride hexahydrate, use of Raney nickel under hydrogen atmosphere, and the like can be employed.

Compound (13) can be produced by subjecting compound (12) to a cyclization reaction, in the presence of a base. Examples of the base include potassium carbonate and the like.

Compound (3-2) can be produced by subjecting compound (13) to a deprotection reaction.

Among compound (3) used in Reaction Scheme 1, compound (3-3), which is compound (3) wherein X is —NR$^3$—, can be produced from compound (7) according to the following method. R$^5$ is methyl, p-methylphenyl or trifluoromethyl.

(Scheme 4)

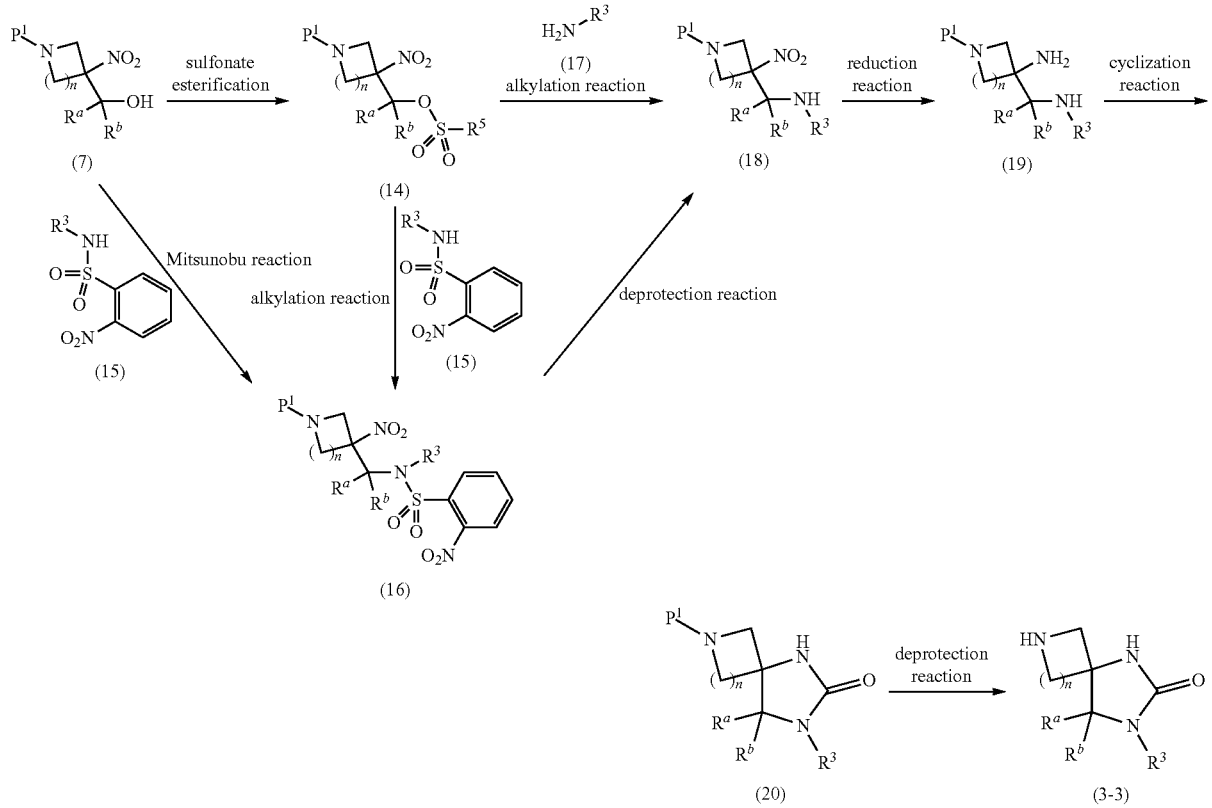

Compound (14) can be produced by subjecting compound (7) to a sulfonate esterification, in the presence of a base. Examples of the base include triethylamine, pyridine and the like.

Compound (16) can be produced by subjecting compound (7) to the Mitsunobu reaction with compound (15). Compound (16) can also be produced by subjecting compound (14) to an alkylation reaction with compound (15), in the presence of a base. Examples of the base include the above-mentioned organic bases, inorganic bases, metal alkoxides, alkali metal hydrides and metal amides.

Compound (18) can be produced by subjecting compound (14) to an alkylation reaction with compound (17), in the presence of a base. Examples of the base include bases as exemplified in the above-mentioned alkylation reaction. Compound (18) can also be produced by subjecting compound (16) to a deprotection reaction, in the presence of a base and a nucleophile.
Examples of the nucleophile to be used include thioglycol acid, thiophenol and the like. Examples of the base include triethylamine, lithium hydroxide, potassium carbonate and the like.

Compound (20) can be produced by subjecting compound (19) to a cyclization reaction. The cyclization reaction may be carried out by using a base. Examples of the base to be used include triethylamine and the like.

Compounds (2), (4), (6), (10), (15) and (17) which are used as starting materials in each scheme, may be commercially available products or can be produced according to a method known per se.

The starting compound and/or production intermediate for compound (I) may form a salt. The salt is not particularly limited as long as the reaction can be performed. Examples thereof include those similar to the salts optionally formed by compound (I), and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

The compound of the present invention is expected to be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, treatment-resistant depression, depressive disorder, catalepsy, hebephrenic schizophrenia, paranoid schizophrenia], (2) neurodegenerative diseases [e.g., Alzheimer's disease, Alzheimer-type senile dementia, Parkinson's disease, Huntington's disease, multi-infarct dementia, frontotemporal dementia, dementia Parkinson's type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis, neuromyelitis optica (NMO), postoperative cognitive dysfunction (POCD), postoperative delirium (POD), delirium], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, neoplasms (e.g., cancer, liver neoplasms, colonic neoplasms, breast neoplasms, prostatic neoplasms, neuroblastoma, bone neoplasms, mouth neoplasms, mastocytoma, cholangiocarcinoma, Lewis lung carcinoma etc.), immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus, rheumatoid arthritis, osteoarthritis, functional dyspepsia, hyperalgesia, insulin resistance, dementia pugilistica, nausea, vomiting, neoplasm metastasis, brain injuries, seizure, body weight changes, weight gain, weight loss, colitis, alcoholism, hypothermia, fatty liver, atherosclerosis, infection, muscle spasticity, hypertension, stroke, malignant migrating partial seizures of infancy, diabetes mellitus, type 2 diabetes mellitus, dyslipidaemia, visceral obesity, ocular hypotension, anorexia, fibrosis, myocardial infarction, cachexia, induced psychotic disorder, ataxia, AIDS wasting syndrome, cirrhotic cardiomyopathy, uremic pruritus, neurobehavioral manifestations, Tubulointerstitial nephritis and uveitis syndrome, interstitial cystitis, retinitis pigmentosa, autoimmune diseases, coronary artery disease, aspirin-induced asthma, platelet storage pool deficiency, diabetic embryopathy, Arthus type urticaria, asthma, toxic oil syndrome, otitis and the like, (7) pain (e.g., inflammatory pain, cancerous pain, neuropathic pain, acute pain, pain associated with peripheral neuropathy, central pain, fibromyalgia, vassooclussive painful crises in sickle cell disease, multiple sclerosis-mediated spasticity or pain, functional chest pain, complex regional pain syndrome etc.), (8) migraine,
(9) cerebral edema,
(10) cerebral ischemia, ischemia, and the like.

Since the compound of the present invention has a superior MAGL inhibitory action, a superior prophylactic or therapeutic effect for the above-mentioned diseases may be expected.

Since the compound of the present invention has a superior MAGL inhibitory action, a superior prophylactic or therapeutic effect for neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like, particularly Alzheimer's disease, Parkinson's disease, Huntington's disease, amyotrophic lateral sclerosis, multiple sclerosis, anxiety disorder, pain, epilepsy or depression may be expected.

Compound (I) can be used as a prodrug.

A prodrug of compound (I) means a compound which is so converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with Alzheimer's disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (Cyamemazine etc.), heart non-selective β inhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, zonisamide, entacapone, amantadine, talipexole, pramipexole, apomorphine, cabergoline, bromocriptine, istradefylline, trihexyphenidyl, promethazine, pergolide, etc.), therapeutic drug for Huntington's disease (chlorpromazine hydrochloride, haloperidol, reserpine etc.), therapeutic drug for ALS (riluzole etc., neurotrophic factor etc.), therapeutic drug for multiple sclerosis (molecular target drug such as fingolimod, interferon beta 1b, natalizumab and the like, etc.), antiepilepsy drug (phenytoin, carbamazepine, phenobarbital, primidone, zonisamide, sodium valproate, ethosuximide, diazepam, nitrazepam, clonazepam, clobazam, gabapentin, topiramate, lamotrigine, levetiracetam, stiripentol, rufinamide, etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of the combination agent of the present invention include those similar to the above-mentioned carriers.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

Powder X-RAY diffraction pattern was measured using Cu-Kα characteristic radiation from Rigaku Ultima IV, and characteristic peaks were described.

In Examples, the following abbreviations are used.
mp: melting point
MS: mass spectrum
M: mol concentration
$CDCl_3$: deuterochloroform
DMSO-$d_6$: deuterodimethyl sulfoxide ¹H NMR: proton nuclear magnetic resonance
LC/MS: liquid chromatograph mass spectrometer
ESI: Electron Spray Ionization
APCI: Atmospheric Pressure Chemical Ionization
DIAD: diisopropyl azodicarboxylate
DMSO: dimethyl sulfoxide
DMA: N,N-dimethylacetamide
DMAP: N,N-dimethyl-4-aminopyridine
DMF: N,N-dimethylformamide
TBAF: tetrabutylammonium fluoride
TEA: triethylamine
THF: tetrahydrofuran Example 1 cis-3-(2-fluoro-4-(trifluoromethyl)phenoxy)cyclobutyl 6-oxo-7-oxa-2,5-diazaspiro[3.4]octane-2-carboxylate A) tert-butyl((cis-3-(2-fluoro-4-(trifluoromethyl)phenoxy)cyclobutyl)oxy)dimethylsilane To a mixture of cis-3-((tert-butyl(dimethyl)silyl)oxy)cyclobutanol (500 mg), 1,2-difluoro-4-(trifluoromethyl)benzene (0.383 mL) and THF (10 mL) was added potassium tert-butoxide (333 mg) at 0° C. The mixture was stirred under argon atmosphere at room temperature for 16 hr. The mixture was diluted with ethyl acetate, washed with water and saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane) to give the title compound (900 mg) as a crude product.

¹H NMR (300 MHz, DMSO-$d_6$) δ 0.05 (6H, s), 0.86 (9H, s), 1.90-2.04 (2H, m), 2.87-3.00 (2H, m), 3.98-4.11 (1H, m), 4.41-4.54 (1H, m), 7.18 (1H, t, J=8.4 Hz), 7.50 (1H, d, J=8.5 Hz), 7.67 (1H, dd, J=11.3, 2.1 Hz).

B) cis-3-(2-fluoro-4-(trifluoromethyl)phenoxy)cyclobutanol

To a mixture of tert-butyl((cis-3-(2-fluoro-4-(trifluoromethyl)phenoxy)cyclobutyl)oxy)dimethylsilane (crude product, 900 mg) and THF (10 mL) was added TBAF (1 M THF solution, 3.7 mL). The mixture was stirred at room temperature for 1 hr. The mixture was diluted with ethyl acetate, washed with water and saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane) to give the title compound (486 mg).

¹H NMR (300 MHz, DMSO-$d_6$) δ 1.89-2.02 (2H, m), 2.81-2.92 (2H, m), 3.79-3.93 (1H, m), 4.37-4.49 (1H, m), 5.24 (1H, d, J=6.8 Hz), 7.19 (1H, t, J=8.5 Hz), 7.50 (1H, d, J=8.7 Hz), 7.67 (1H, dd, J=11.3, 2.1 Hz).

C) tert-butyl 3-(hydroxymethyl)-3-nitroazetidine-1-carboxylate

To a mixture of tert-butyl 3-nitroazetidine-1-carboxylate (90 g) and acetonitrile (1.25 L) was added formaldehyde (37% an aqueous solution, 73 mL), and then TEA (60 mL) was added dropwise thereto at room temperature, and the reaction mixture was stirred at room temperature for 16 hr. The reaction mixture was concentrated under reduced pressure. The residue was purified by silica gel column chromatography (ethyl acetate/petroleum ether) to give the title compound (85 g).

¹H NMR (500 MHz, CDCl3) δ 1.45 (9H, s), 2.68 (1H, brs), 4.11 (2H, d, J=10.4 Hz), 4.19-4.21 (2H, m), 4.39-4.46 (2H, m).

D) tert-butyl 6-oxo-7-oxa-2,5-diazaspiro[3.4]octane-2-carboxylate

To a mixture of tert-butyl 3-(hydroxymethyl)-3-nitroazetidine-1-carboxylate (85 g), Raney nickel (9 g) and methanol (1.5 L) was subjected to hydrogenation at 60 psi at room temperature for 16 hr. The reaction mixture was filtered through Celite, and the filtrate was concentrated under reduced pressure to give an intermediate (68 g). To a mixture of the obtained intermediate (68 g), TEA (100 mL) and THF (1.5 L) was added triphosgene (40 g) at 0° C., and the reaction mixture was stirred at 0° C. for 30 min. Then, the reaction mixture was stirred at room temperature for 2 hr. The reaction mixture was poured into saturated aqueous sodium hydrogencarbonate solution, and extracted with ethyl acetate. The organic layer was washed with saturated brine, dried over anhydrous sodium sulfate, and concentrated under reduced pressure. The residue was purified by silica gel column chromatography (ethyl acetate/petroleum ether) to give the title compound (58 g).

¹H NMR (500 MHz, CDCl$_3$) δ 1.43 (9H, s), 4.03 (2H, d, J=10.1 Hz), 4.13 (2H, d, J=9.5 Hz), 4.53 (2H, s), 6.52 (1H, brs).

E) 7-oxa-2,5-diazaspiro[3.4]octan-6-one tosylate

To a mixture of tert-butyl 6-oxo-7-oxa-2,5-diazaspiro[3.4]octane-2-carboxylate (58 g) and ethyl acetate (1.2 L) was added tosylic acid hydrate (58 g) at room temperature, and the mixture was heated under reflux for 2 hr. The reaction mixture was cooled to room temperature, tosylic acid hydrate (14.5 g) was added thereto, and the mixture was heated under reflux for additional 2 hr. The reaction mixture was cooled to room temperature, and the solid was collected by filtration, washed with diethyl ether, and dried under reduced pressure to give the title compound (62 g).

¹H NMR (400 MHz, DMSO-d6) δ 2.29 (3H, s), 4.05-4.15 (4H, m), 4.54 (2H, s), 7.13 (2H, d, J=7.8 Hz), 7.50 (2H, d, J=7.8 Hz), 8.51-8.54 (3H, m).

F) cis-3-(2-fluoro-4-(trifluoromethyl)phenoxy)cyclobutyl 6-oxo-7-oxa-2,5-diazaspiro[3.4]octane-2-carboxylate To a mixture of cis-3-(2-fluoro-4-(trifluoromethyl)phenoxy)cyclobutanol (486 mg), TEA (1.08 mL) and acetonitrile (16 mL) was added triphosgene (202 mg). The reaction mixture was stirred at 0° C. for 30 min, and 7-oxa-2,5-diazaspiro[3.4]octan-6-one tosylate (583 mg) was added thereto. The mixture was stirred at the same temperature for 16 hr. The mixture was diluted with ethyl acetate, washed with saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane), and solidified from ethyl acetate/hexane to give the title compound (605 mg).

¹H NMR (300 MHz, DMSO-$d_6$) δ 2.06-2.21 (2H, m), 2.93-3.07 (2H, m), 3.92-4.17 (4H, m), 4.47 (2H, s), 4.54-

4.71 (2H, m), 7.20 (1H, t, J=8.5 Hz), 7.51 (1H, d, J=7.7 Hz), 7.69 (1H, dd, J=11.4, 2.0 Hz), 8.40 (1H, s).

Example 2 cis-3-(benzyloxy)cyclobutyl 6-oxo-7-oxa-2,5-diazaspiro[3.4]octane-2-carboxylate

To a mixture of cis-3-(benzyloxy)cyclobutanol (328 mg), TEA (1.03 mL) and acetonitrile (15 mL) was added triphosgene (191 mg). The reaction mixture was stirred at 0° C. for 30 min, and 7-oxa-2,5-diazaspiro[3.4]octan-6-one tosylate (553 mg) was added thereto. The mixture was stirred at the same temperature for 16 hr. The mixture was diluted with ethyl acetate, washed with saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane), and solidified from diisopropyl ether to give the title compound (436 mg).

$^1$H NMR (300 MHz, DMSO-$d_6$) δ 1.80-1.95 (2H, m), 2.59-2.72 (2H, m), 3.65-3.78 (1H, m), 3.89-4.16 (4H, m), 4.36 (2H, s), 4.43-4.45 (3H, m), 7.24-7.40 (5H, m), 8.39 (1H, s).

Example 3 cis-3-((3-chloro-4-methylbenzyl)oxy)cyclobutyl 6-oxo-7-oxa-2,5-diazaspiro[3.4]octane-2-carboxylate A) tert-butyl((cis-3-((3-chloro-4-methylbenzyl)oxy)cyclobutyl)oxy)dimethylsilane To a mixture of cis-3-((tert-butyl(dimethyl)silyl)oxy)cyclobutanol (500 mg) and DMF (9.3 mL) was added sodium hydride (60%, 109 mg) at 0° C. The reaction mixture was stirred at the same temperature for 10 min, and a mixture of 4-(bromomethyl)-2-chloro-1-methylbenzene (597 mg) and DMF (3.1 mL) was added thereto. The mixture was stirred under argon atmosphere at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (782 mg).

$^1$H NMR (300 MHz, DMSO-$d_6$) δ 0.00 (6H, s), 0.83 (9H, s), 1.67-1.81 (2H, m), 2.30 (3H, s), 2.52-2.64 (2H, m), 3.55 (1H, quint, J=7.0 Hz), 3.88 (1H, quint, J=7.1 Hz), 4.29 (2H, s), 7.16 (1H, dd, J=7.9, 1.5 Hz), 7.26-7.37 (2H, m).

B) cis-3-((3-chloro-4-methylbenzyl)oxy)cyclobutanol

To a mixture of tert-butyl((cis-3-((3-chloro-4-methylbenzyl)oxy)cyclobutyl)oxy)dimethylsilane (782 mg) and THF (12 mL) was added TBAF (1 M THF solution, 4.6 mL). The mixture was stirred at room temperature for 64 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (461 mg).

$^1$H NMR (300 MHz, DMSO-$d_6$) δ 1.65-1.80 (2H, m), 2.31 (3H, s), 2.45-2.58 (2H, m), 3.46-3.59 (1H, m), 3.60-3.74 (1H, m), 4.30 (2H, s), 4.99 (1H, d, J=6.6 Hz), 7.13-7.20 (1H, m), 7.27-7.36 (2H, m).

C) cis-3-((3-chloro-4-methylbenzyl)oxy)cyclobutyl 6-oxo-7-oxa-2,5-diazaspiro[3.4]octane-2-carboxylate To a mixture of cis-3-((3-chloro-4-methylbenzyl)oxy)cyclobutanol (461 mg), TEA (1.13 mL) and acetonitrile (10 mL) was added triphosgene (211 mg) at 0° C. The reaction mixture was stirred at the same temperature for 20 min, and 7-oxa-2,5-diazaspiro[3.4]octan-6-one tosylate (641 mg) was added thereto. The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and solidified from ethyl acetate/hexane to give the title compound (575 mg).

$^1$H NMR (300 MHz, DMSO-$d_6$) δ 1.88 (2H, dtd, J=9.8, 7.3, 2.9 Hz), 2.31 (3H, s), 2.65 (2H, dtd, J=9.7, 6.6, 2.9 Hz), 3.71 (1H, quint, J=6.8 Hz), 3.89-4.01 (2H, m), 4.08 (2H, d, J=8.7 Hz), 4.33 (2H, s), 4.40-4.57 (3H, m), 7.18 (1H, dd, J=7.6, 1.4 Hz), 7.32 (1H, d, J=7.7 Hz), 7.35 (1H, d, J=1.5 Hz), 8.38 (1H, s).

Example 4 cis-3-((4-chloro-3-methylbenzyl)oxy)cyclobutyl 6-oxo-7-oxa-2,5-diazaspiro[3.4]octane-2-carboxylate A) tert-butyl((cis-3-((4-chloro-3-methylbenzyl)oxy)cyclobutyl)oxy)dimethylsilane To a mixture of cis-3-((tert-butyl(dimethyl)silyl)oxy)cyclobutanol (500 mg) and DMF (9.3 mL) was added sodium hydride (60%, 109 mg) under argon atmosphere at 0° C. The reaction mixture was stirred at the same temperature for 10 min, and a mixture of 4-(bromomethyl)-1-chloro-2-methylbenzene (597 mg) and DMF (3.1 mL) was added thereto at 0° C. The mixture was stirred under argon atmosphere at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (833 mg).

$^1$H NMR (300 MHz, DMSO-$d_6$) δ 0.01 (6H, s), 0.85 (9H, s), 1.67-1.83 (2H, m), 2.32 (3H, s), 2.59 (2H, dtd, J=9.0, 6.4, 2.9 Hz), 3.57 (1H, quint, J=7.0 Hz), 3.89 (1H, quint, J=7.1 Hz), 4.30 (2H, s), 7.15 (1H, dd, J=8.2, 1.8 Hz), 7.28 (1H, s), 7.36 (1H, d, J=8.1 Hz).

B) cis-3-((4-chloro-3-methylbenzyl)oxy)cyclobutanol

To a mixture of tert-butyl((cis-3-((4-chloro-3-methylbenzyl)oxy)cyclobutyl)oxy)dimethylsilane (833 mg) and THF (12 mL) was added TBAF (1 M THF solution, 4.9 mL). The mixture was stirred at room temperature for 64 hr. The mixture was diluted with ethyl acetate, washed with water and saturated brine, dried over anhydrous magnesium sulfate, and concentrated under reduced pressure. The residue was purified by silica gel column chromatography (ethyl acetate/hexane) to give the title compound (511 mg).

$^1$H NMR (300 MHz, DMSO-d$_6$) δ 1.64-1.80 (2H, m), 2.32 (3H, s), 2.47-2.59 (2H, m), 3.47-3.59 (1H, m), 3.60-3.75 (1H, m), 4.29 (2H, s), 4.99 (1H, d, J=6.6 Hz), 7.14 (1H, dd, J=8.1, 1.7 Hz), 7.28 (1H, s), 7.36 (1H, d, J=8.1 Hz).

C) cis-3-((4-chloro-3-methylbenzyl)oxy)cyclobutyl 6-oxo-7-oxa-2,5-diazaspiro[3.4]octane-2-carboxylate To a mixture of cis-3-((4-chloro-3-methylbenzyl)oxy)cyclobutanol (511 mg), TEA (1.26 mL) and acetonitrile (11 mL) was added triphosgene (234 mg) at 0° C. The reaction mixture was stirred at the same temperature for 20 min, and 7-oxa-2,5-diazaspiro[3.4]octan-6-one tosylate (711 mg) was added thereto. The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and solidified from ethyl acetate/hexane to give the title compound (651 mg).

$^1$H NMR (300 MHz, DMSO-d$_6$) δ 1.80-1.95 (2H, m), 2.32 (3H, s), 2.65 (2H, dtd, J=9.7, 6.6, 3.0 Hz), 3.71 (1H, quint, J=6.8 Hz), 3.91-4.01 (2H, m), 4.08 (2H, d, J=9.3 Hz), 4.32 (2H, s), 4.42-4.57 (3H, m), 7.16 (1H, dd, J=8.1, 1.7 Hz), 7.29 (1H, d, J=1.5 Hz), 7.37 (1H, d, J=8.1 Hz), 8.38 (1H, s).

Example 5 cis-3-((2,3-difluoro-4-methylbenzyl)oxy)cyclobutyl 6-oxo-7-oxa-2,5-diazaspiro[3.4]octane-2-carboxylate A) tert-butyl((cis-3-((2,3-difluoro-4-methylbenzyl)oxy)cyclobutyl)oxy)dimethylsilane To a mixture of cis-3-((tert-butyl(dimethyl)silyl)oxy)cyclobutanol (400 mg) and DMF (5 mL) was added sodium hydride (60%, 87 mg) at 0° C. The reaction mixture was stirred at the same temperature for 30 min, and 1-(bromomethyl)-2,3-difluoro-4-methylbenzene (481 mg) was added thereto at room temperature. The mixture was stirred overnight under argon atmosphere at room temperature. The mixture was poured into water, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (636 mg).

$^1$H NMR (300 MHz, DMSO-d$_6$) δ 0.00-0.02 (6H, m), 0.84 (9H, s), 1.65-1.81 (2H, m), 2.27 (3H, d, J=2.1 Hz), 2.54-2.66 (2H, m), 3.58 (1H, quint, J=7.0 Hz), 3.89 (1H, quint, J=7.1 Hz), 4.38 (2H, d, J=7.1 Hz), 7.01-7.18 (2H, m).

B) cis-3-((2,3-difluoro-4-methylbenzyl)oxy)cyclobutanol

To a mixture of tert-butyl((cis-3-((2,3-difluoro-4-methylbenzyl)oxy)cyclobutyl)oxy)dimethylsilane (636 mg) and THF (10 mL) was added TBAF (1 M THF solution, 2.8 mL) at room temperature. The mixture was stirred at the same temperature for 3 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (302 mg).

$^1$H NMR (300 MHz, DMSO-d$_6$) δ1.63-1.79 (2H, m), 2.27 (3H, d, J=2.1 Hz), 2.51-2.58 (2H, m), 3.54 (1H, quint, J=7.1 Hz), 3.61-3.74 (1H, m), 4.38 (2H, d, J=1.1 Hz), 5.00 (1H, d, J=6.8 Hz), 6.88-7.29 (2H, m).

C) cis-3-((2,3-difluoro-4-methylbenzyl)oxy)cyclobutyl 6-oxo-7-oxa-2,5-diazaspiro[3.4]octane-2-carboxylate To a mixture of 3-((2,3-difluoro-4-methylbenzyl)oxy)cyclobutanol (302 mg), TEA (0.74 mL) and acetonitrile (10 mL) was added triphosgene (137 mg) at 0° C. The reaction mixture was stirred at the same temperature for 30 min, and 7-oxa-2,5-diazaspiro[3.4]octan-6-one tosylate (417 mg) was added thereto at 0° C. The mixture was stirred at room temperature for 4 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and solidified from ethyl acetate/hexane to give the title compound (300 mg).

$^1$H NMR (300 MHz, DMSO-d$_6$) δ 1.77-1.92 (2H, m), 2.27 (3H, d, J=2.1 Hz), 2.59-2.71 (2H, m), 3.60-3.81 (1H, m), 3.89-4.02 (2H, m), 4.02-4.13 (2H, m), 4.41 (2H, s), 4.45-4.54 (3H, m), 6.96-7.20 (2H, m), 8.38 (1H, s).

Example 6 cis-3-((2,3,4-trifluorobenzyl)oxy)cyclobutyl 6-oxo-7-oxa-2,5-diazaspiro[3.4]octane-2-carboxylate A) tert-butyl(dimethyl) ((cis-3-((2,3,4-trifluorobenzyl)oxy)cyclobutyl)oxy)silane To a mixture of cis-3-((tert-butyl(dimethyl)silyl)oxy)cyclobutanol (400 mg) and DMF (6.0 mL) was added sodium hydride (60%, 95.0 mg) at 0° C. The reaction mixture was stirred at the same temperature for 10 min, and 1-(bromomethyl)-2,3,4-trifluorobenzene (534 mg) was added thereto at 0° C. The mixture was stirred at room temperature for 3 hr. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (716 mg).

$^1$H NMR (300 MHz, DMSO-d$_6$) δ 0.01 (6H, s), 0.84 (9H, s), 1.64-1.90 (2H, m), 2.53-2.67 (2H, m), 3.59 (1H, quint, J=7.1 Hz), 3.90 (1H, quint, J=7.1 Hz), 4.40 (2H, s), 7.23-7.40 (2H, m).

B) cis-3-((2,3,4-trifluorobenzyl)oxy)cyclobutanol

To a mixture of tert-butyl(dimethyl) ((cis-3-((2,3,4-trifluorobenzyl)oxy)cyclobutyl)oxy)silane (715 mg) and THF (7.0 mL) was added TBAF (1 M THF solution, 3.1 mL) at 0° C. The mixture was stirred at room temperature for 3 hr. To the mixture was added water, and the mixture was extracted with ethyl acetate. The organic layer was separated, washed with saturated brine, dried over anhydrous sodium sulfate, and concentrated under reduced pressure.

The residue was purified by silica gel column chromatography (ethyl acetate/hexane) to give the title compound (413 mg).

$^1$H NMR (300 MHz, DMSO-$d_6$) δ 1.64-1.79 (2H, m), 2.51-2.60 (2H, m), 3.50-3.61 (1H, m), 3.61-3.78 (1H, m), 4.40 (2H, s), 5.02 (1H, d, J=6.4 Hz), 7.23-7.38 (2H, m).

C) cis-3-((2,3,4-trifluorobenzyl)oxy)cyclobutyl 6-oxo-7-oxa-2,5-diazaspiro[3.4]octane-2-carboxylate To a mixture of cis-3-((2,3,4-trifluorobenzyl)oxy)cyclobutanol (250 mg), TEA (0.898 mL) and acetonitrile (5.0 mL) was added triphosgene (112 mg) at 0° C. The reaction mixture was stirred at the same temperature for 30 min, and 7-oxa-2,5-diazaspiro[3.4]octan-6-one tosylate (340 mg) was added thereto at 0° C. The mixture was stirred at room temperature for 4 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane and methanol/ethyl acetate), and solidified from ethyl acetate/hexane to give the title compound (176 mg).

$^1$H NMR (300 MHz, DMSO-$d_6$) δ 1.76-1.98 (2H, m), 2.57-2.79 (2H, m), 3.74 (1H, quint, J=6.8 Hz), 3.87-4.21 (4H, m), 4.36-4.61 (5H, m), 7.21-7.43 (2H, m), 8.39 (1H, s).

Example 7 cis-3-((2,4,5-trifluorobenzyl)oxy)cyclobutyl 6-oxo-7-oxa-2,5-diazaspiro[3.4]octane-2-carboxylate A) tert-butyl(dimethyl) ((cis-3-((2,4,5-trifluorobenzyl)oxy)cyclobutyl)oxy)silane To a mixture of cis-3-((tert-butyl(dimethyl)silyl)oxy)cyclobutanol (500 mg) and DMF (5 mL) was added sodium hydride (60%, 109 mg) at 0° C. The reaction mixture was stirred at room temperature for 30 min, and 1-(bromomethyl)-2,4,5-trifluorobenzene (0.358 mL) was added thereto at 0° C. The mixture was stirred under argon atmosphere at room temperature for 3 hr. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (428 mg).

$^1$H NMR (300 MHz, DMSO-$d_6$) δ 0.01 (6H, s), 0.85 (9H, s), 1.69-1.80 (2H, m), 2.54-2.65 (2H, m), 3.54-3.65 (1H, m), 3.84-3.95 (1H, m), 4.35 (2H, s), 7.47-7.59 (2H, m).

B) cis-3-((2,4,5-trifluorobenzyl)oxy)cyclobutanol

To a mixture of tert-butyl(dimethyl) ((cis-3-((2,4,5-trifluorobenzyl)oxy)cyclobutyl)oxy)silane (428 mg) and THF (8 mL) was added TBAF (1 M THF solution, 1.5 mL) at room temperature. The mixture was stirred at the same temperature for 1 hr. To the mixture was added saturated brine at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (126 mg).

$^1$H NMR (300 MHz, DMSO-$d_6$) δ 1.65-1.79 (2H, m), 2.51-2.59 (2H, m), 3.56 (1H, quint, J=7.0 Hz), 3.62-3.75 (1H, m), 4.35 (2H, s), 5.01 (1H, d, J=6.6 Hz), 7.52 (2H, ddt, J=10.8, 9.5, 6.7 Hz).

C) cis-3-((2,4,5-trifluorobenzyl)oxy)cyclobutyl 6-oxo-7-oxa-2,5-diazaspiro[3.4]octane-2-carboxylate To a mixture of cis-3-((2,4,5-trifluorobenzyl)oxy)cyclobutanol (126 mg), TEA (0.333 mL) and acetonitrile (3 mL) was added triphosgene (56.4 mg) at 0° C. The reaction mixture was stirred at the same temperature for 20 min, and 7-oxa-2,5-diazaspiro[3.4]octan-6-one tosylate (163 mg) was added thereto at 0° C. The mixture was stirred at room temperature for 3 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (77.3 mg).

$^1$H NMR (300 MHz, DMSO-$d_6$) δ 1.81-1.94 (2H, m), 2.60-2.72 (2H, m), 3.74 (1H, quint, J=6.8 Hz), 3.92-4.14 (4H, m), 4.34-4.55 (5H, m), 7.48-7.61 (2H, m), 8.39 (1H, s).

Example 8 cis-3-((2,4,6-trifluorobenzyl)oxy)cyclobutyl 6-oxo-7-oxa-2,5-diazaspiro[3.4]octane-2-carboxylate A) tert-butyl(dimethyl) ((cis-3-((2,4,6-trifluorobenzyl)oxy)cyclobutyl)oxy)silane To a mixture of cis-3-((tert-butyl(dimethyl)silyl)oxy)cyclobutanol (400 mg) and DMF (7.4 mL) was added sodium hydride (60%, 87 mg) at 0° C. The reaction mixture was stirred at the same temperature for 10 min, and a mixture of 2-(bromomethyl)-1,3,5-trifluorobenzene (489 mg) and DMF (2.5 mL) was added thereto at 0° C. The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (682 mg).

$^1$H NMR (300 MHz, DMSO-$d_6$) δ 0.00 (6H, s), 0.84 (9H, s), 1.63-1.77 (2H, m), 2.52-2.65 (2H, m), 3.57 (1H, quint, J=6.9 Hz), 3.90 (1H, quint, J=7.1 Hz), 4.36 (2H, s), 7.13-7.27 (2H, m).

B) cis-3-((2,4,6-trifluorobenzyl)oxy)cyclobutanol

To a mixture of tert-butyl(dimethyl) ((cis-3-((2,4,6-trifluorobenzyl)oxy)cyclobutyl)oxy)silane (682 mg) and THF (9.8 mL) was added TBAF (1 M THF solution, 3.9 mL). The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (397 mg).

¹H NMR (300 MHz, DMSO-d₆) δ 1.60-1.75 (2H, m), 2.44-2.57 (2H, m), 3.53 (1H, quint, J=7.0 Hz), 3.60-3.75 (1H, m), 4.35 (2H, s), 5.00 (1H, d, J=6.8 Hz), 7.13-7.27 (2H, m).

C) cis-3-((2,4,6-trifluorobenzyl)oxy)cyclobutyl 6-oxo-7-oxa-2,5-diazaspiro[3.4]octane-2-carboxylate To a mixture of cis-3-((2,4,6-trifluorobenzyl)oxy)cyclobutanol (397 mg), TEA (0.953 mL) and acetonitrile (8.5 mL) was added triphosgene (178 mg) at 0° C. The reaction mixture was stirred at the same temperature for 20 min, and 7-oxa-2,5-diazaspiro[3.4]octan-6-one tosylate (539 mg) was added thereto. The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and solidified from diisopropyl ether to give the title compound (218 mg).

¹H NMR (300 MHz, DMSO-d₆) δ 1.71-1.91 (2H, m), 2.56-2.78 (2H, m), 3.71 (1H, quint, J=6.8 Hz), 3.89-4.01 (2H, m), 4.02-4.15 (2H, m), 4.39 (2H, s), 4.43-4.56 (3H, m), 7.15-7.28 (2H, m), 8.38 (1H, s).

Example 9 cis-3-((3,4-dichlorobenzyl)oxy)cyclobutyl 6-oxo-7-oxa-2,5-diazaspiro[3.4]octane-2-carboxylate A) tert-butyl((cis-3-((3,4-dichlorobenzyl)oxy)cyclobutyl)oxy)dimethylsilane To a mixture of cis-3-((tert-butyl(dimethyl)silyl)oxy)cyclobutanol (270 mg) and DMF (3 mL) was added sodium hydride (60%, 58.7 mg) at 0° C. The reaction mixture was stirred at room temperature for 30 min, and 4-(bromomethyl)-1,2-dichlorobenzene (0.213 mL) was added thereto Jo at 0° C. The mixture was stirred under argon atmosphere at room temperature for 3 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (240 mg).

¹H NMR (300 MHz, DMSO-d₆) δ 0.01 (6H, s), 0.85 (9H, s), 1.71-1.83 (2H, m), 2.54-2.65 (2H, m), 3.53-3.64 (1H, m), 3.90 (1H, quint, J=7.1 Hz), 4.35 (2H, s), 7.31 (1H, dd, J=8.3, 1.9 Hz), 7.57 (1H, d, J=1.9 Hz), 7.60 (1H, d, J=8.3 Hz).

B) cis-3-((3,4-dichlorobenzyl)oxy)cyclobutanol

To a mixture of tert-butyl((cis-3-((3,4-dichlorobenzyl)oxy)cyclobutyl)oxy)dimethylsilane (240 mg) and THF (3 mL) was added TBAF (1 M THF solution, 0.66 mL) at room temperature. The mixture was stirred at the same temperature for 1 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (100 mg).

¹H NMR (300 MHz, DMSO-d₆) δ 1.67-1.80 (2H, m), 2.51-2.59 (2H, m), 3.49-3.61 (1H, m), 3.61-3.75 (1H, m), 4.35 (2H, s), 4.97-5.03 (1H, m), 7.31 (1H, dd, J=8.3, 1.9 Hz), 7.56 (1H, d, J=1.9 Hz), 7.60 (1H, d, J=8.1 Hz).

C) cis-3-((3,4-dichlorobenzyl)oxy)cyclobutyl 6-oxo-7-oxa-2,5-diazaspiro[3.4]octane-2-carboxylate To a mixture of cis-3-((3,4-dichlorobenzyl)oxy)cyclobutanol (100 mg), TEA (0.186 mL) and acetonitrile (2 mL) was added triphosgene (42.0 mg) at 0° C. The reaction mixture was stirred at the same temperature for 10 min, and 7-oxa-2,5-diazaspiro[3.4]octan-6-one tosylate (122 mg) was added thereto at 0° C. The mixture was stirred at 0° C. for 2 hr. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and then purified by HPLC (C18, mobile phase: water/acetonitrile (containing 0.1% TFA)). To the obtained fraction was added saturated aqueous sodium hydrogencarbonate solution, and the mixture was extracted with ethyl acetate. The extract was dried over anhydrous magnesium sulfate, and concentrated under reduced pressure. The residue was solidified from ethyl acetate/hexane to give the title compound (18.5 mg).

¹H NMR (300 MHz, DMSO-d₆) δ 1.89 (2H, dtd, J=9.8, 7.3, 2.9 Hz), 2.60-2.71 (2H, m), 3.73 (1H, quint, J=6.9 Hz), 3.92-4.14 (4H, m), 4.35-4.56 (5H, m), 7.32 (1H, dd, J=8.3, 1.9 Hz), 7.56-7.64 (2H, m), 8.39 (1H, s)

Example 10 cis-3-((2-fluoro-4-(trifluoromethyl)benzyl)oxy)cyclobutyl 6-oxo-7-oxa-2,5-diazaspiro[3.4]octane-2-carboxylate A) cis-3-((2-fluoro-4-(trifluoromethyl)benzyl)oxy)cyclobutanol To a mixture of cis-3-((tert-butyl(diphenyl)silyl)oxy)cyclobutanol (352 mg) and DMF (4.0 mL) was added sodium hydride (60%, 51.8 mg) at 0° C. The reaction mixture was stirred at the same temperature for 10 min, and a mixture of 1-(bromomethyl)-2-fluoro-4-(trifluoromethyl)benzene (277 mg) and DMF (1.5 mL) was added thereto at 0° C. The mixture was stirred at room temperature for 3 days. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give an intermediate (315 mg) as a crude product. To a mixture of the obtained intermediate (crude product, 310 mg) and THF (4.0 mL) was added TBAF (1 M THF solution, 0.27 mL) at room temperature. The mixture was stirred at room temperature for 4 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (132 mg).

¹H NMR (300 MHz, CDCl₃) δ 1.70 (1H, d, J=6.4 Hz), 1.88-2.03 (2H, m), 2.69-2.85 (2H, m), 3.67 (1H, quint, J=6.9 Hz), 3.96 (1H, sxt, J=7.0 Hz), 4.52 (2H, s), 7.31 (1H, d, J=9.8 Hz), 7.42 (1H, d, J=7.9 Hz), 7.52-7.64 (1H, m).

B) cis-3-((2-fluoro-4-(trifluoromethyl)benzyl)oxy) cyclobutyl 6-oxo-7-oxa-2,5-diazaspiro[3.4]octane-2-carboxylate To a mixture of cis-3-((2-fluoro-4-(trifluoromethyl)benzyl)oxy)cyclobutanol (131 mg), TEA (0.275 mL) and acetonitrile (3.5 mL) was added triphosgene (51.3 mg) at 0° C. The reaction mixture was stirred at the same temperature for 30 min, and 7-oxa-2,5-diazaspiro[3.4]octan-6-one tosylate (156 mg) was added thereto at 0° C. The mixture was stirred at room temperature for 4 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane and methanol/ethyl acetate), and solidified from ethyl acetate/hexane to give the title compound (73.6 mg).

$^1$H NMR (300 MHz, DMSO-$d_6$) δ 1.82-2.03 (2H, m), 2.61-2.78 (2H, m), 3.78 (1H, quint, J=6.9 Hz), 3.90-4.19 (4H, m), 4.41-4.61 (5H, m), 7.57-7.77 (3H, m), 8.39 (1H, s).

Example 11 cis-3-((3-chloro-4-(trifluoromethyl)benzyl)oxy)cyclobutyl 6-oxo-7-oxa-2,5-diazaspiro[3.4]octane-2-carboxylate

A) tert-butyl((cis-3-((3-chloro-4-(trifluoromethyl)benzyl)oxy)cyclobutyl)oxy)dimethylsilane To a mixture of cis-3-((tert-butyl(dimethyl)silyl)oxy)cyclobutanol (416 mg) and DMF (7.7 mL) was added sodium hydride (60%, 90 mg) at 0° C. The reaction mixture was stirred at the same temperature for 10 min, and a mixture of 3-chloro-4-(trifluoromethyl)benzyl methanesulfonate (653 mg) and DMF (2.6 mL) was added thereto at 0° C. The mixture was stirred at room temperature for 2 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (549 mg).

$^1$H NMR (300 MHz, DMSO-$d_6$) δ 0.02 (6H, s), 0.85 (9H, s), 1.72-1.86 (2H, m), 2.55-2.68 (2H, m), 3.62 (1H, quint, J=7.0 Hz), 3.91 (1H, quint, J=7.1 Hz), 4.45 (2H, s), 7.49 (1H, d, J=8.1 Hz), 7.64 (1H, s), 7.83 (1H, d, J=8.1 Hz).

B) cis-3-((3-chloro-4-(trifluoromethyl)benzyl)oxy)cyclobutanol

To a mixture of tert-butyl((cis-3-((3-chloro-4-(trifluoromethyl)benzyl)oxy)cyclobutyl)oxy)dimethylsilane (549 mg) and THF (7.0 mL) was added TBAF (1 M THF solution, 2.8 mL). The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (293 mg).

$^1$H NMR (300 MHz, DMSO-$d_6$) δ 1.67-1.83 (2H, m), 2.50-2.61 (2H, m), 3.52-3.76 (2H, m), 4.45 (2H, s), 5.03 (1H, d, J=6.6 Hz), 7.49 (1H, dd, J=8.1, 0.8 Hz), 7.64 (1H, s), 7.83 (1H, d, J=8.1 Hz).

C) cis-3-((3-chloro-4-(trifluoromethyl)benzyl)oxy) cyclobutyl 6-oxo-7-oxa-2,5-diazaspiro[3.4]octane-2-carboxylate To a mixture of cis-3-((3-chloro-4-(trifluoromethyl)benzyl)oxy)cyclobutanol (293 mg), TEA (0.582 mL) and acetonitrile (5.2 mL) was added triphosgene (108 mg) at 0° C. The reaction mixture was stirred at the same temperature for 20 min, and 7-oxa-2,5-diazaspiro[3.4]octan-6-one tosylate (329 mg) was added thereto. The mixture was stirred at room temperature for 16 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (methanol/ethyl acetate), and solidified from ethyl acetate/hexane to give the title compound (46.0 mg).

$^1$H NMR (300 MHz, DMSO-$d_6$) δ 1.83-2.03 (2H, m), 2.60-2.79 (2H, m), 3.76 (1H, quint, J=6.9 Hz), 3.89-4.02 (2H, m), 4.09 (2H, d, J=8.7 Hz), 4.39-4.59 (5H, m), 7.50 (1H, d, J=7.9 Hz), 7.66 (1H, s), 7.84 (1H, d, J=8.3 Hz), 8.39 (1H, s).

Example 12 cis-3-((2-fluoro-4-methylphenoxy)methyl)cyclobutyl 6-oxo-7-oxa-2,5-diazaspiro[3.4]octane-2-carboxylate

A) (cis-3-(benzyloxy)cyclobutyl)methyl 4-methylbenzenesulfonate

To a mixture of (cis-3-(benzyloxy)cyclobutyl)methanol (1.78 g), 4-methylbenzenesulfonyl chloride (1.94 g) and acetonitrile (20 mL) was added dropwise TEA (1.93 mL) at 0° C., and trimethylamine hydrochloride (88 mg) was added thereto. The mixture was stirred at the same temperature for 40 min, and partitioned between brine and ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (2.97 g).

$^1$H NMR (300 MHz, DMSO-$d_6$) δ 1.46-1.63 (2H, m), 2.02-2.28 (3H, m), 2.42 (3H, s), 3.86 (1H, quint, J=7.2 Hz), 3.99 (2H, d, J=6.0 Hz), 4.31 (2H, s), 7.21-7.39 (5H, m), 7.48 (2H, d, J=7.9 Hz), 7.70-7.85 (2H, m).

B) 1-((cis-3-(benzyloxy)cyclobutyl)methoxy)-2-fluoro-4-methylbenzene

A mixture of (cis-3-(benzyloxy)cyclobutyl)methyl 4-methylbenzenesulfonate (300 mg), 2-fluoro-4-methylphenol (131 mg), potassium carbonate (239 mg) and DMF (3.0 mL) was stirred at 80° C. for 16 hr. To the mixture was added water, and the mixture was extracted with ethyl acetate. The organic layer was separated, washed with water and saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane) to give the title compound (260 mg).

$^1$H NMR (300 MHz, DMSO-$d_6$) δ 1.67-1.80 (2H, m), 2.15-2.39 (6H, m), 3.88-3.99 (3H, m), 4.37 (2H, s), 6.86-6.93 (1H, m), 6.97-7.06 (2H, m), 7.23-7.39 (5H, m).

C) cis-3-((2-fluoro-4-methylphenoxy)methyl)cyclobutanol

A mixture of 1-((cis-3-(benzyloxy)cyclobutyl)methoxy)-2-fluoro-4-methylbenzene (260 mg), palladium/carbon (Pd 10%, 50% hydrous, 184 mg) and methanol (20 mL) was stirred under normal pressure of hydrogen atmosphere at room temperature for 2 hr. The catalyst was removed by filtration, and the filtrate was concentrated under reduced pressure. The residue was dissolved in ethyl acetate, and the solution was passed through NH silica gel, and eluted with ethyl acetate to give the title compound (182 mg).

$^1$H NMR (300 MHz, DMSO-$d_6$) δ 1.55-1.69 (2H, m), 2.01-2.18 (1H, m), 2.23 (3H, s), 2.24-2.35 (2H, m), 3.90-4.07 (3H, m), 5.00 (1H, d, J=6.4 Hz), 6.86-6.93 (1H, m), 6.96-7.05 (2H, m)

D) cis-3-((2-fluoro-4-methylphenoxy)methyl)cyclobutyl 6-oxo-7-oxa-2,5-diazaspiro[3.4]octane-2-carboxylate To a mixture of cis-3-((2-fluoro-4-methylphenoxy)methyl)cyclobutanol (182 mg), TEA (0.483 mL) and acetonitrile (9 mL) was added triphosgene (90 mg). The reaction mixture was stirred at 0° C. for 30 min, and 7-oxa-2,5-diazaspiro[3.4]octan-6-one tosylate (260 mg) was added thereto. The mixture was stirred at the same temperature for 16 hr. The mixture was diluted with ethyl acetate, washed with saturated brine, and dried over anhydrous sodium sulfate. The solution was passed through NH silica gel, and eluted with ethyl acetate. The solution was concentrated, and the residue was solidified from ethyl acetate/hexane (3/1) to give the title compound (238 mg).

$^1$H NMR (300 MHz, DMSO-$d_6$) δ 1.75-1.93 (2H, m), 2.23 (3H, s), 2.26-2.47 (3H, m), 3.90-4.14 (6H, m), 4.47 (2H, s), 4.70-4.85 (1H, m), 6.86-6.95 (1H, m), 6.97-7.06 (2H, m), 8.34-8.42 (1H, m).

Example 13 cis-3-((4-fluoro-2-methylphenoxy)methyl)cyclobutyl 6-oxo-7-oxa-2,5-diazaspiro[3.4]octane-2-carboxylate

A) 1-((cis-3-(benzyloxy)cyclobutyl)methoxy)-4-fluoro-2-methylbenzene

To a mixture of 4-fluoro-2-methylphenol (120 mg), potassium carbonate (263 mg) and DMA (5 mL) was added (cis-3-(benzyloxy)cyclobutyl)methyl 4-methylbenzenesulfonate (300 mg) at room temperature. The mixture was stirred at 80° C. for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (215 mg).

$^1$H NMR (300 MHz, DMSO-$d_6$) δ 1.67-1.88 (2H, m), 2.15 (3H, s), 2.19-2.41 (3H, m), 3.79-4.01 (3H, m), 4.38 (2H, s), 6.79-7.07 (3H, m), 7.18-7.46 (5H, m).

B) cis-3-((4-fluoro-2-methylphenoxy)methyl)cyclobutanol

A mixture of 1-((cis-3-(benzyloxy)cyclobutyl)methoxy)-4-fluoro-2-methylbenzene (215 mg), palladium/carbon (Pd 10%, 50% hydrous, 100 mg) and methanol (20 mL) was stirred overnight under normal pressure of hydrogen atmosphere at room temperature. The catalyst was removed by filtration, and the filtrate was concentrated under reduced pressure. The residue was purified by silica gel column chromatography (ethyl acetate/hexane) to give the title compound (145 mg).

$^1$H NMR (300 MHz, DMSO-$d_6$) δ 1.57-1.74 (2H, m), 2.03-2.14 (1H, m), 2.15 (3H, s), 2.23-2.35 (2H, m), 3.87 (2H, d, J=6.0 Hz), 3.91-4.05 (1H, m), 5.00 (1H, brs), 6.72-7.13 (3H, m).

C) cis-3-((4-fluoro-2-methylphenoxy)methyl)cyclobutyl 6-oxo-7-oxa-2,5-diazaspiro[3.4]octane-2-carboxylate To a mixture of cis-3-((4-fluoro-2-methylphenoxy)methyl)cyclobutanol (145 mg), TEA (0.38 mL) and acetonitrile (5 mL) was added triphosgene (71.6 mg) at 0° C. The reaction mixture was stirred at the same temperature for 30 min, and 7-oxa-2,5-diazaspiro[3.4]octan-6-one tosylate (217 mg) was added thereto. The mixture was stirred at room temperature for 4 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and solidified from ethyl acetate/hexane to give the title compound (125 mg).

$^1$H NMR (300 MHz, DMSO-$d_6$) δ 1.80-1.98 (2H, m), 2.17 (3H, s), 2.26-2.45 (3H, m), 3.91 (2H, d, J=5.1 Hz), 3.94-4.02 (2H, m), 4.03-4.12 (2H, m), 4.47 (2H, s), 4.66-4.88 (1H, m), 6.80-7.10 (3H, m), 8.38 (1H, s).

Example 14 cis-3-((2-chloro-4-fluorophenoxy)methyl)cyclobutyl 6-oxo-7-oxa-2,5-diazaspiro[3.4]octane-2-carboxylate

A) ethyl cis-3-((tert-butyl(dimethyl)silyl)oxy)cyclobutanecarboxylate

To a mixture of 2,6-dimethylpyridine (9.44 mL), ethyl cis-3-hydroxycyclobutanecarboxylate (5.84 g) and DMF (50 mL) was added tert-butyl(dimethyl)silyl trifluoromethanesulfonate (11 mL) at 0° C. The mixture was stirred at room temperature for 3 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (10.4 g).

$^1$H NMR (300 MHz, DMSO-$d_6$) δ 0.02 (6H, s), 0.85 (9H, s), 1.17 (3H, t, J=7.1 Hz), 1.89-2.02 (2H, m), 2.37-2.47 (2H, m), 2.53-2.65 (1H, m), 4.05 (2H, q, J=7.2 Hz), 4.11-4.22 (1H, m).

B) (cis-3-((tert-butyl(dimethyl)silyl)oxy)cyclobutyl)methanol

To a mixture of ethyl cis-3-((tert-butyl(dimethyl)silyl)oxy)cyclobutanecarboxylate (10.4 g) and THF (100 mL) was added lithium aluminium hydride (1.69 g) at 0° C. The mixture was stirred at the same temperature for 30 min. To the mixture was added sodium sulfate 10 hydrate at 0° C., and the mixture was stirred at room temperature for 30 min.

The mixture was filtered through Celite, and the filtrate was concentrated under reduced pressure. The residue was purified by silica gel column chromatography (ethyl acetate/hexane) to give the title compound (5.66 g).

$^1$H NMR (300 MHz, DMSO-d$_6$) δ 0.01 (6H, s), 0.85 (9H, s), 1.48-1.62 (2H, m), 1.71-1.86 (1H, m), 2.11-2.24 (2H, m), 3.27-3.38 (2H, m), 4.03-4.15 (1H, m), 4.42 (1H, t, J=5.5 Hz).

C) (cis-3-((tert-butyl(dimethyl)silyl)oxy)cyclobutyl) methyl 4-methylbenzenesulfonate To a mixture of (cis-3-((tert-butyl(dimethyl)silyl)oxy)cyclobutyl)methanol (3.25 g), TEA (2.71 mL) and acetonitrile (35 mL) were added 4-methylbenzenesulfonyl chloride (3.01 g) and trimethylamine hydrochloride (144 mg) at 0° C. The mixture was stirred at the same temperature for 10 min, and then at room temperature for 1 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (5.12 g).

$^1$H NMR (300 MHz, DMSO-d$_6$) 56-0.02 (6H, s), 0.82 (9H, s), 1.40-1.54 (2H, m), 1.92-2.07 (1H, m), 2.10-2.29 (2H, m), 2.42 (3H, s), 3.97 (2H, d, J=6.4 Hz), 4.08 (1H, quint, J=7.3 Hz), 7.48 (2H, d, J=7.9 Hz), 7.73-7.84 (2H, m).

D) tert-butyl((cis-3-((2-chloro-4-fluorophenoxy)methyl)cyclobutyl)oxy)dimethylsilane A mixture of (cis-3-((tert-butyl(dimethyl)silyl)oxy)cyclobutyl)methyl 4-methylbenzenesulfonate (678 mg), 2-chloro-4-fluorophenol (349 mg), potassium carbonate (379 mg) and DMF (5.0 mL) was stirred overnight at 80° C. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (338 mg).

$^1$H NMR (300 MHz, DMSO-d$_6$) δ 0.00 (6H, s), 0.83 (9H, s), 1.65-1.80 (2H, m), 2.05-2.20 (1H, m), 2.24-2.40 (2H, m), 3.97 (2H, d, J=6.0 Hz), 4.15 (1H, quint, J=7.3 Hz), 7.07-7.18 (2H, m), 7.33-7.45 (1H, m).

E) cis-3-((2-chloro-4-fluorophenoxy)methyl)cyclobutanol

To a mixture of tert-butyl((cis-3-((2-chloro-4-fluorophenoxy)methyl)cyclobutyl)oxy)dimethylsilane (337 mg) and THF (4.0 mL) was added TBAF (1 M THF solution, 1.5 mL) at room temperature. The mixture was stirred at the same temperature for 2 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (214 mg).

$^1$H NMR (300 MHz, DMSO-d$_6$) δ 1.58-1.74 (2H, m), 2.04-2.21 (1H, m), 2.22-2.39 (2H, m), 3.87-4.09 (3H, m), 5.01 (1H, d, J=6.4 Hz), 7.07-7.26 (2H, m), 7.31-7.52 (1H, m).

F) cis-3-((2-chloro-4-fluorophenoxy)methyl)cyclobutyl 6-oxo-7-oxa-2,5-diazaspiro[3.4]octane-2-carboxylate To a mixture of cis-3-((2-chloro-4-fluorophenoxy)methyl)cyclobutanol (213 mg), TEA (0.770 mL) and acetonitrile (4.0 mL) was added triphosgene (96.0 mg) at 0° C. The reaction mixture was stirred at the same temperature for 20 min, and 7-oxa-2,5-diazaspiro[3.4]octan-6-one tosylate (291 mg) was added thereto. The mixture was stirred overnight at room temperature. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and solidified from ethyl acetate/hexane. The obtained solid was purified by HPLC (C18, mobile phase: water/acetonitrile (containing 10 mM NH$_4$HCO$_3$)). The obtained fraction was partially concentrated under reduced pressure, and the residue was extracted with ethyl acetate. The extract was washed with saturated brine, dried over anhydrous sodium sulfate, and concentrated under reduced pressure. The residue was solidified from ethyl acetate/hexane to give the title compound (235 mg).

$^1$H NMR (300 MHz, DMSO-d$_6$) δ 1.81-2.01 (2H, m), 2.24-2.46 (3H, m), 3.89-4.15 (6H, m), 4.47 (2H, s), 4.69-4.88 (1H, m), 7.03-7.24 (2H, m), 7.34-7.56 (1H, m), 8.39 (1H, s).

Example 15 cis-3-((4-chloro-2-fluorophenoxy)methyl)cyclobutyl 6-oxo-7-oxa-2,5-diazaspiro[3.4]octane-2-carboxylate A) ethyl cis-3-((tert-butyl(diphenyl)silyl)oxy)cyclobutanecarboxylate To a mixture of ethyl cis-3-hydroxycyclobutanecarboxylate (500 mg), imidazole (283 mg), DMAP (21.2 mg) and DMF (12 mL) was added tert-butyl(diphenyl)chlorosilane (1.05 g). The mixture was stirred at room temperature for 5 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (1.23 g).

$^1$H NMR (300 MHz, DMSO-d$_6$) δ 0.98 (9H, s), 1.12-1.22 (3H, m), 2.05-2.18 (2H, m), 2.27-2.41 (2H, m), 2.52-2.59 (1H, m), 3.94-4.09 (2H, m), 4.10-4.22 (1H, m), 7.36-7.52 (6H, m), 7.53-7.66 (4H, m).

B) (cis-3-((tert-butyl(diphenyl)silyl)oxy)cyclobutyl) methanol

To a mixture of ethyl cis-3-((tert-butyl(diphenyl)silyl)oxy)cyclobutanecarboxylate (4.3 g) and THF (50 mL) was added dropwise a mixture of lithium aluminium hydride (469 mg) and THF (50 mL) at 0° C. The mixture was stirred at the same temperature for 15 min. To the mixture was added sodium sulfate 10 hydrate, and the mixture was stirred for 15 min. The insoluble substance was removed by filtration, and the filtrate was concentrated under reduced pressure. The residue was purified by silica gel column chromatography (ethyl acetate/hexane) to give the title compound (3.54 g).

$^1$H NMR (300 MHz, DMSO-d$_6$) δ 0.97 (9H, s), 1.64-1.82 (3H, m), 2.06-2.17 (2H, m), 3.31-3.36 (2H, m), 4.04-4.16 (1H, m), 4.43 (1H, t, J=5.4 Hz), 7.31-7.51 (6H, m), 7.55-7.67 (4H, m).

C) (cis-3-((tert-butyl(diphenyl)silyl)oxy)cyclobutyl) methyl 4-methylbenzenesulfonate To a mixture of (cis-3-((tert-butyl(diphenyl)silyl)oxy)cyclobutyl)methanol (900 mg), 4-methylbenzenesulfonyl chloride (554 mg) and acetonitrile (9.0 mL) were added TEA (0.551 mL) and trimethylamine hydrochloride (25.3 mg) at 0° C. The mixture was stirred at the same temperature for 1 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (1.29 g).

$^1$H NMR (300 MHz, DMSO-d$_6$) δ 0.95 (9H, s), 1.54-1.73 (2H, m), 1.82-1.97 (1H, m), 2.03-2.21 (2H, m), 2.39 (1H, s), 2.42 (3H, s), 3.98 (2H, d, J=6.0 Hz), 7.37-7.51 (8H, m), 7.53-7.62 (4H, m), 7.77 (2H, d, J=8.3 Hz).

D) tert-butyl((cis-3-((4-chloro-2-fluorophenoxy) methyl)cyclobutyl)oxy)diphenylsilane A mixture of (cis-3-((tert-butyl(diphenyl) silyl)oxy)cyclobutyl)methyl 4-methylbenzenesulfonate (500 mg), 4-chloro-2-fluorophenol (178 mg), potassium carbonate (210 mg) and DMF (4.0 mL) was stirred at 80° C. for 4 hr. To the mixture was added water at room temperature, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (439 mg).

$^1$H NMR (300 MHz, DMSO-d$_6$) δ 0.98 (9H, s), 1.74-1.94 (2H, m), 2.01-2.15 (1H, m), 2.17-2.35 (2H, m), 4.00 (2H, d, J=6.0 Hz), 4.17 (1H, quint, J=7.2 Hz), 7.08-7.24 (2H, m), 7.35-7.52 (7H, m), 7.56-7.71 (4H, m).

E) cis-3-((4-chloro-2-fluorophenoxy)methyl)cyclobutanol

To a mixture of tert-butyl((cis-3-((4-chloro-2-fluorophenoxy)methyl)cyclobutyl)oxy)diphenylsilane (430 mg) and THF (4.0 mL) was added TBAF (1 M THF solution, 0.41 mL) at room temperature. The mixture was stirred at the same temperature for 2 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (202 mg).

$^1$H NMR (300 MHz, DMSO-d$_6$) δ 1.52-1.72 (2H, m), 2.02-2.20 (1H, m), 2.22-2.40 (2H, m), 3.89-4.08 (3H, m), 5.03 (1H, d, J=6.4 Hz), 7.10-7.23 (2H, m), 7.35-7.46 (1H, m).

F) cis-3-((4-chloro-2-fluorophenoxy)methyl)cyclobutyl 6-oxo-7-oxa-2,5-diazaspiro[3.4]octane-2-carboxylate To a mixture of cis-3-((4-chloro-2-fluorophenoxy) methyl)cyclobutanol (200 mg), TEA (0.723 mL) and acetonitrile (4.0 mL) was added triphosgene (90.0 mg) at 0° C. The reaction mixture was stirred at the same temperature for 30 min, and 7-oxa-2,5-diazaspiro[3.4]octan-6-one tosylate (273 mg) was added thereto. The mixture was stirred at room temperature for 2 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and solidified from ethyl acetate/hexane. The obtained solid was purified by HPLC (column: CHIRALPAK AD, 50 mmID× 500 mmL, manufactured by Daicel Corporation, mobile phase: hexane/ethanol (400/600 (v/v))), and solidified from ethyl acetate/hexane to give the title compound (170 mg).

$^1$H NMR (300 MHz, DMSO-d$_6$) δ 1.76-1.94 (2H, m), 2.22-2.46 (3H, m), 3.88-4.23 (6H, m), 4.47 (2H, s), 4.66-4.91 (1H, m), 7.11-7.27 (2H, m), 7.37-7.50 (1H, m), 8.39 (1H, s).

Example 16 cis-3-((2,3,4-trifluorophenoxy)methyl)cyclobutyl 6-oxo-7-oxa-2,5-diazaspiro[3.4]octane-2-carboxylate A) tert-butyl(dimethyl) ((cis-3-((2,3,4-trifluorophenoxy)methyl)cyclobutyl)oxy)silane A mixture of (cis-3-((tert-butyl(dimethyl)silyl)oxy)cyclobutyl)methyl 4-methylbenzenesulfonate (53.3 g), 2,3,4-trifluorophenol (22.6 g), cesium carbonate (70.3 g) and DMF (290 mL) was stirred overnight at room temperature. To this mixture was added a solution of 2,3,4-trifluorophenol (8.52 g) in DMF (50 mL) at room temperature, and the mixture was stirred for 3 days. The mixture was diluted with water, and extracted with toluene/ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (45.6 g).

$^1$H NMR (300 MHz, CDCl$_3$) δ 0.05 (6H, s), 0.88 (9H, s), 1.70-1.89 (2H, m), 2.09-2.30 (1H, m), 2.37-2.52 (2H, m), 3.97 (2H, d, J=6.4 Hz), 4.12-4.25 (1H, m), 6.56-6.73 (1H, m), 6.77-6.96 (1H, m).

B) cis-3-((2,3,4-trifluorophenoxy)methyl)cyclobutanol

To a mixture of tert-butyl(dimethyl) ((cis-3-((2,3,4-trifluorophenoxy)methyl)cyclobutyl)oxy)silane (46.6 g) and THF (270 mL) was added TBAF hydrate (42.2 g) at 0° C. portionwise, and the reaction mixture was stirred at room temperature for 1 hr. The mixture was diluted with water, and extracted with ethyl acetate. The organic layer was separated, and washed with water and saturated brine. The aqueous layer was re-extracted with ethyl acetate. The organic layer was separated, washed with water and saturated brine. The organic layers were combined, dried over anhydrous sodium sulfate, and concentrated under reduced pressure. The residue was purified by silica gel column chromatography (ethyl acetate/hexane) to give the title compound (31.2 g).

$^1$H NMR (300 MHz, DMSO-d$_6$) δ 1.52-1.72 (2H, m), 2.03-2.21 (1H, m), 2.24-2.38 (2H, m), 3.91-4.09 (3H, m), 5.04 (1H, d, J=6.4 Hz), 6.94-7.10 (1H, m), 7.13-7.35 (1H, m).

C) cis-3-((2,3,4-trifluorophenoxy)methyl)cyclobutyl 6-oxo-7-oxa-2,5-diazaspiro[3.4]octane-2-carboxylate To a mixture of cis-3-((2,3,4-trifluorophenoxy)methyl)cyclobutanol (2.25 g), TEA (6.73 mL) and acetonitrile (24 mL) was added triphosgene (1.01 g) at 0° C., and the reaction mixture was stirred at the same temperature for 1 hr. To this mixture was added 7-oxa-2,5-diazaspiro[3.4]octan-6-one tosylate (2.91 g) at 0° C., and the reaction mixture was warmed to room temperature. The mixture was stirred at room temperature for 16 hr, diluted with water, and extracted with ethyl acetate. The organic layer was separated, washed with saturated brine, dried over anhydrous sodium sulfate, and concentrated under reduced pressure. The residue was purified by silica gel column chromatography (ethyl acetate/hexane and methanol/ethyl acetate), and solidified from ethyl acetate/hexane. The obtained solid was recrystallized from ethanol/water/heptane to give the title compound (2.54 g).

$^1$H NMR (300 MHz, DMSO-d$_6$) δ 1.78-2.00 (2H, m), 2.24-2.47 (3H, m), 3.91-4.20 (6H, m), 4.47 (2H, s), 4.72-4.87 (1H, m), 6.96-7.09 (1H, m), 7.19-7.32 (1H, m), 8.39 (1H, s).
mp 145° C.
powder X-RAY crystal diffraction pattern (diffraction angle 2θ): 9.8°, 13.6°, 14.4°, 15.2°, 18.2°, 19.6°, 22.0°, 24.30, 25.4° and 29.10

Example 17 cis-3-((2,4,5-trifluorophenoxy)methyl)cyclobutyl 6-oxo-7-oxa-2,5-diazaspiro[3.4]octane-2-carboxylate A) 1-((cis-3-(benzyloxy)cyclobutyl)methoxy)-2,4,5-trifluorobenzene To a mixture of 2,4,5-trifluorophenol (282 mg), potassium carbonate (527 mg) and DMF (6 mL) was added (cis-3-(benzyloxy)cyclobutyl)methyl 4-methylbenzenesulfonate (600 mg) at room temperature. The mixture was stirred at 80° C. for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (455 mg).

$^1$H NMR (300 MHz, DMSO-d$_6$) δ 1.67-1.80 (2H, m), 2.16-2.40 (3H, m), 3.94 (1H, quint, J=7.3 Hz), 4.02 (2H, d, J=6.0 Hz), 4.37 (2H, s), 7.23-7.45 (6H, m), 7.57 (1H, td, J=10.9, 7.9 Hz).

B) cis-3-((2,4,5-trifluorophenoxy)methyl)cyclobutanol

A mixture of 1-((cis-3-(benzyloxy)cyclobutyl)methoxy)-2,4,5-trifluorobenzene (455 mg), palladium/carbon (Pd 10%, 50% hydrous, 100 mg) and methanol (5 mL) was stirred overnight under normal pressure of hydrogen atmosphere at room temperature. The catalyst was removed by filtration, and the filtrate was concentrated under reduced pressure. To the residue were added palladium/carbon (Pd 10%, 50% hydrous, 100 mg) and methanol (5 mL), and the mixture was stirred under normal pressure of hydrogen atmosphere at room temperature for 2 hr. The catalyst was removed by filtration, and the filtrate was concentrated under reduced pressure to give the title compound (307 mg).

$^1$H NMR (300 MHz, DMSO-d$_6$) δ 1.56-1.68 (2H, m), 2.02-2.19 (1H, m), 2.24-2.35 (2H, m), 3.94-4.02 (3H, m), 5.03 (1H, brs), 7.38 (1H, dt, J=12.4, 8.0 Hz), 7.56 (1H, td, J=11.0, 7.9 Hz).

C) cis-3-((2,4,5-trifluorophenoxy)methyl)cyclobutyl 6-oxo-7-oxa-2,5-diazaspiro[3.4]octane-2-carboxylate To a mixture of cis-3-((2,4,5-trifluorophenoxy)methyl)cyclobutanol (307 mg), TEA (0.737 mL) and acetonitrile (6 mL) was added triphosgene (157 mg) at 0° C. The reaction mixture was stirred at the same temperature for 30 min, and 7-oxa-2,5-diazaspiro[3.4]octan-6-one tosylate (397 mg) was added thereto. The mixture was stirred at room temperature for 4 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (219 mg).

$^1$H NMR (300 MHz, DMSO-d$_6$) δ 1.78-1.92 (2H, m), 2.27-2.47 (3H, m), 3.94-4.13 (6H, m), 4.47 (2H, s), 4.72-4.85 (1H, m), 7.39 (1H, dt, J=12.3, 8.0 Hz), 7.58 (1H, td, J=10.9, 7.5 Hz), 8.39 (1H, s).

Example 18 cis-3-((2,4,6-trifluorophenoxy)methyl)cyclobutyl 6-oxo-7-oxa-2,5-diazaspiro[3.4]octane-2-carboxylate A) 2-((cis-3-(benzyloxy)cyclobutyl)methoxy)-1,3,5-trifluorobenzene To a mixture of (cis-3-(benzyloxy)cyclobutyl)methyl 4-methylbenzenesulfonate (350 mg), 2,4,6-trifluorophenol (180 mg) and DMF (4.0 mL) was added potassium carbonate (209 mg) at room temperature. The mixture was stirred overnight at 80° C. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (298 mg).

$^1$H NMR (300 MHz, DMSO-d$_6$) δ 1.63-1.84 (2H, m), 2.07-2.24 (1H, m), 2.24-2.41 (2H, m), 3.86-3.97 (1H, m), 4.01 (2H, d, J=6.0 Hz), 4.36 (2H, s), 7.17-7.40 (7H, m).

B) cis-3-((2,4,6-trifluorophenoxy)methyl)cyclobutanol

A mixture of 2-((cis-3-(benzyloxy)cyclobutyl)methoxy)-1,3,5-trifluorobenzene (294 mg), palladium hydroxide/carbon (Pd 20%, 50% hydrous, 30.0 mg) and ethyl acetate (4.0 mL) was stirred under normal pressure of hydrogen atmosphere at room temperature for 4 hr. The catalyst was removed by filtration, and the filtrate was concentrated under reduced pressure to give the title compound (211 mg).
¹H NMR (300 MHz, DMSO-d$_6$) δ 1.52-1.73 (2H, m), 1.96-2.15 (1H, m), 2.17-2.35 (2H, m), 3.89-4.07 (3H, m), 4.99 (1H, d, J=6.4 Hz), 7.02-7.40 (2H, m).

C) cis-3-((2,4,6-trifluorophenoxy)methyl)cyclobutyl 6-oxo-7-oxa-2,5-diazaspiro[3.4]octane-2-carboxylate To a mixture of cis-3-((2,4,6-trifluorophenoxy)methyl)cyclobutanol (209 mg), TEA (0.751 mL) and acetonitrile (4.0 mL) was added triphosgene (93.0 mg) at 0° C. The reaction mixture was stirred at the same temperature for 20 min, and 7-oxa-2,5-diazaspiro[3.4]octan-6-one tosylate (284 mg) was added thereto. The mixture was stirred overnight at room temperature. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and crystallized from ethyl acetate/hexane to give the title compound (266 mg).
¹H NMR (300 MHz, DMSO-d$_6$) δ 1.75-2.02 (2H, m), 2.17-2.46 (3H, m), 3.89-4.20 (6H, m), 4.47 (2H, s), 4.76 (1H, quint, J=7.3 Hz), 7.16-7.37 (2H, m), 8.38 (1H, s).
mp 111° C.
powder X-RAY crystal diffraction pattern (diffraction angle 2θ): 3.7°, 7.4°, 14.8°, 18.1°, 20.6°, 22.3° and 24.4°

Example 19 cis-3-((2-fluoro-4-(trifluoromethyl)phenoxy)methyl)cyclobutyl 6-oxo-7-oxa-2,5-diazaspiro[3.4]octane-2-carboxylate A) cis-3-(ethoxycarbonyl)cyclobutyl 6-oxo-7-oxa-2,5-diazaspiro[3.4]octane-2-carboxylate To a mixture of ethyl cis-3-hydroxycyclobutanecarboxylate (324 mg), TEA (1.04 mL) and acetonitrile (19 mL) was added triphosgene (233 mg) at 0° C. The reaction mixture was stirred at the same temperature for 10 min, and 7-oxa-2,5-diazaspiro[3.4]octan-6-one tosylate (562 mg) was added thereto at 0° C. The mixture was stirred at room temperature for 16 hr.
To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (370 mg).
¹H NMR (300 MHz, DMSO-d$_6$) δ 1.17 (3H, t, J=7.1 Hz), 2.04-2.18 (2H, m), 2.44-2.57 (2H, m), 2.69-2.84 (1H, m), 3.90-4.15 (6H, m), 4.47 (2H, s), 4.78 (1H, quint, J=7.6 Hz), 8.39 (1H, s).

B) cis-3-((2-fluoro-4-(trifluoromethyl)phenoxy)methyl)cyclobutyl 6-oxo-7-oxa-2,5-diazaspiro[3.4]octane-2-carboxylate To a mixture of lithium aluminium hydride (70.6 mg) and THF (6.2 mL) was added dropwise a mixture of cis-3-(ethoxycarbonyl)cyclobutyl 6-oxo-7-oxa-2,5-diazaspiro[3.4]octane-2-carboxylate (370 mg) and THF (6.2 mL) at 0° C. The mixture was stirred under argon atmosphere at the same temperature for 30 min. To the mixture were successively added water, 15% aqueous sodium hydroxide solution and water at 0° C., and the mixture was stirred at room temperature for 30 min. The insoluble substance was removed by filtration, and the filtrate was concentrated under reduced pressure. The residue was purified by silica gel column chromatography (ethyl acetate/hexane) to give an intermediate (67.7 mg) as a crude product. To a mixture of the obtained intermediate (crude product, 67.7 mg), 2-fluoro-4-(trifluoromethyl)phenol (47.6 mg) and THF (5.3 mL) were added triphenylphosphine (polymer-supported, 3 mmol/g, 440 mg) and bis(2-methoxyethyl) (E)-diazene-1,2-dicarboxylate (124 mg). The mixture was stirred at room temperature for 3 hr. The insoluble substance was removed by filtration, and the filtrate was partitioned between water and ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/diisopropyl ether to give the title compound (28.5 mg).
¹H NMR (300 MHz, DMSO-d$_6$) δ 1.79-1.95 (2H, m), 2.27-2.46 (3H, m), 3.90-4.02 (2H, m), 4.03-4.19 (4H, m), 4.47 (2H, s), 4.72-4.87 (1H, m), 7.30-7.40 (1H, m), 7.53 (1H, d, J=8.9 Hz), 7.67 (1H, dd, J=11.2, 2.0 Hz), 8.39 (1H, s).

Example 20 cis-3-((2-chloro-4-(trifluoromethyl)phenoxy)methyl)cyclobutyl 6-oxo-7-oxa-2,5-diazaspiro[3.4]octane-2-carboxylate A) cis-3-((((4-methylphenyl)sulfonyl)oxy)methyl)cyclobutyl 6-oxo-7-oxa-2,5-diazaspiro[3.4]octane-2-carboxylate To a mixture of cis-3-(hydroxymethyl)cyclobutyl 6-oxo-7-oxa-2,5-diazaspiro[3.4]octane-2-carboxylate (67.9 mg) and pyridine (2 mL) was added 4-methylbenzenesulfonyl chloride (60.6 mg). The mixture was stirred at room temperature for 16 hr. The mixture was diluted with ethyl acetate, washed with 1 M hydrochloric acid and saturated brine, and dried over anhydrous sodium sulfate. The solution was passed through NH silica gel, eluted with ethyl acetate, and concentrated under reduced pressure to give the title compound (109 mg) as a crude product.
MS: [M+H]$^+$ 411.2.

B) cis-3-((2-chloro-4-(trifluoromethyl)phenoxy)methyl)cyclobutyl 6-oxo-7-oxa-2,5-diazaspiro[3.4]octane-2-carboxylate A mixture of cis-3-((((4-methylphenyl)sulfonyl)oxy)methyl)cyclobutyl 6-oxo-7-oxa-2,5-diazaspiro[3.4]octane-2-carboxylate (crude product, 109 mg), 2-chloro-4-(trifluoromethyl)phenol (78 mg), potassium carbonate (110 mg) and DMF (3 mL) was stirred at 80° C. for 1 hr. The mixture was diluted with ethyl acetate at room temperature, washed with saturated brine, and dried over anhydrous sodium sulfate. The solution was passed through NH silica gel, eluted with ethyl acetate, and concentrated under reduced pressure. The residue was purified by silica gel column chromatography (ethyl acetate/hexane), and solidified from diisopropyl ether to give the title compound (19.4 mg).

¹H NMR (300 MHz, DMSO-d₆) δ 1.85-2.02 (2H, m), 2.30-2.54 (3H, m), 3.91-4.19 (6H, m), 4.47 (2H, s), 4.71-4.87 (1H, m), 7.32 (1H, d, J=8.7 Hz), 7.68 (1H, dd, J=8.9, 2.1 Hz), 7.84 (1H, d, J=1.9 Hz), 8.39 (1H, s).

Example 21 trans-3-((2,3,4-trifluorophenoxy)methyl)cyclobutyl 6-oxo-7-oxa-2,5-diazaspiro[3.4]octane-2-carboxylate A) (trans-3-(benzyloxy)cyclobutyl)methyl 4-methylbenzenesulfonate To a mixture of (trans-3-(benzyloxy)cyclobutyl)methanol (236 mg), TEA (0.256 mL) and acetonitrile (4.0 mL) were added 4-methylbenzenesulfonyl chloride (281 mg) and trimethylamine hydrochloride (11.7 mg) at 0° C. The mixture was stirred at the same temperature for 45 min. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (425 mg).

¹H NMR (300 MHz, CDCl₃) δ 1.99-2.24 (4H, m), 2.45 (3H, s), 2.48-2.64 (1H, m), 4.02 (2H, d, J=6.8 Hz), 4.05-4.16 (1H, m), 4.36 (2H, s), 7.27-7.44 (7H, m), 7.72-7.84 (2H, m).

B) 1-((trans-3-(benzyloxy)cyclobutyl)methoxy)-2,3,4-trifluorobenzene

A mixture of (trans-3-(benzyloxy)cyclobutyl)methyl 4-methylbenzenesulfonate (417 mg), 2,3,4-trifluorophenol (214 mg), potassium carbonate (250 mg) and DMF (4.0 mL) was stirred at 80° C. for 8 hr. To the reaction mixture were added 2,3,4-trifluorophenol (428 mg) and potassium carbonate (499 mg), and the mixture was stirred at 100° C. for 6 hr, and then at 80° C. for 14 hr. To the mixture was added water, and the mixture was extracted with ethyl acetate/toluene. The organic layer was separated, washed with water and saturated brine, dried over anhydrous sodium sulfate, and concentrated under reduced pressure. The residue was purified by silica gel column chromatography (ethyl acetate/hexane), and then purified by silica gel column chromatography (NH, ethyl acetate/hexane) to give the title compound (352 mg).

¹H NMR (300 MHz, DMSO-d₆) δ 2.12 (4H, t, J=6.6 Hz), 2.61 (1H, dt, J=13.5, 6.6 Hz), 4.08 (2H, d, J=6.8 Hz), 4.21 (1H, quint, J=6.7 Hz), 4.36 (2H, s), 7.04 (1H, tdd, J=9.2, 4.9, 2.6 Hz), 7.18-7.43 (6H, m).

C) trans-3-((2,3,4-trifluorophenoxy)methyl)cyclobutanol

A mixture of 1-((trans-3-(benzyloxy)cyclobutyl)methoxy)-2,3,4-trifluorobenzene (346 mg), palladium hydroxide/carbon (Pd 20%, 50% hydrous, 35.0 mg) and ethyl acetate (5.0 mL) was stirred overnight under normal pressure of hydrogen atmosphere at room temperature. The catalyst was removed by filtration, and the filtrate was concentrated under reduced pressure. The residue was purified by silica gel column chromatography (ethyl acetate/hexane) to give the title compound (212 mg).

¹H NMR (300 MHz, DMSO-d₆) δ 1.92-2.16 (4H, m), 4.05 (2H, d, J=7.2 Hz), 4.27 (1H, sxt, J=6.8 Hz), 5.03 (1H, d, J=6.0 Hz), 6.97-7.10 (1H, m), 7.18-7.34 (1H, m).

D) trans-3-((2,3,4-trifluorophenoxy)methyl)cyclobutyl 6-oxo-7-oxa-2,5-diazaspiro[3.4]octane-2-carboxylate To a mixture of trans-3-((2,3,4-trifluorophenoxy)methyl)cyclobutanol (100 mg), TEA (0.299 mL) and acetonitrile (4.0 mL) was added triphosgene (44.7 mg) at 0° C. The reaction mixture was stirred at the same temperature for 20 min, and 7-oxa-2,5-diazaspiro[3.4]octan-6-one tosylate (136 mg) was added thereto at 0° C. The mixture was stirred overnight at room temperature. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane and methanol/ethyl acetate), and solidified from ethyl acetate/diisopropyl ether to give the title compound (130 mg).

¹H NMR (300 MHz, DMSO-d₆) δ 2.13-2.31 (4H, m), 2.58-2.77 (1H, m), 3.92-4.22 (6H, m), 4.48 (2H, s), 5.02 (1H, quint, J=7.1 Hz), 6.98-7.12 (1H, m), 7.19-7.34 (1H, m), 8.40 (1H, s).

Example 22 trans-3-((2-fluoro-4-(trifluoromethyl)phenoxy)methyl)cyclobutyl 6-oxo-7-oxa-2,5-diazaspiro[3.4]octane-2-carboxylate A) trans-3-(ethoxycarbonyl)cyclobutyl 6-oxo-7-oxa-2,5-diazaspiro[3.4]octane-2-carboxylate To a mixture of ethyl trans-3-hydroxycyclobutanecarboxylate (329 mg), TEA (1.04 mL) and acetonitrile (19 mL) was added triphosgene (233 mg) at 0° C. The reaction mixture was stirred at the same temperature for 10 min, and 7-oxa-2,5-diazaspiro[3.4]octan-6-one tosylate (562 mg) was added thereto at 0° C. The mixture was stirred at room temperature for 16 hr. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (330 mg).

¹H NMR (300 MHz, DMSO-d₆) δ 1.07-1.27 (3H, m), 2.19-2.36 (2H, m), 2.38-2.48 (2H, m), 2.98-3.13 (1H, m), 3.88-4.19 (6H, m), 4.47 (2H, s), 4.96 (1H, quint, J=7.1 Hz), 8.40 (1H, s).

B) trans-3-((2-fluoro-4-(trifluoromethyl)phenoxy)methyl)cyclobutyl 6-oxo-7-oxa-2,5-diazaspiro[3.4]octane-2-carboxylate To a mixture of lithium aluminium hydride (63.0 mg) and THF (5.5 mL) was added dropwise a mixture of trans-3-(ethoxycarbonyl)cyclobutyl 6-oxo-7-oxa-2,5-diazaspiro[3.4]octane-2-carboxylate (330 mg) and THF (5.5 mL) at 0° C. The mixture was stirred under argon atmosphere at 0° C. for 30 min. To the mixture were added successively water, 15% aqueous sodium hydroxide solution and water at 0° C., and the mixture was stirred at room temperature for 30 min. The insoluble substance was removed by filtration, and the filtrate was concentrated under reduced pressure. The residue was purified by silica gel column chromatography (methanol/ethyl acetate) to give an intermediate (49.3 mg) as a crude product. To a mixture of the obtained intermediate (crude product, 49.3 mg), 2-fluoro-4-(trifluoromethyl)phenol (34.6 mg) and THF (3.9 mL) were added triphenylphosphine (polymer-supported, 3 mmol/g, 320 mg) and bis(2-methoxyethyl) (E)-diazene-1,2-dicarboxylate (90 mg). The mixture was stirred at room temperature for 3 hr. The insoluble substance was removed by filtration, and the filtrate was partitioned between ethyl acetate and water. The organic layer was separated, washed with water and saturated brine, dried over anhydrous magnesium sulfate, and concentrated under reduced pressure. The residue was purified by silica gel column chromatography (ethyl acetate), and solidified from ethyl acetate/diisopropyl ether to give the title compound (5.4 mg).

$^1$H NMR (300 MHz, DMSO-$d_6$) δ 2.17-2.31 (4H, m), 2.59-2.78 (1H, m), 3.92-4.03 (2H, m), 4.05-4.14 (2H, m), 4.19 (2H, d, J=6.8 Hz), 4.48 (2H, s), 5.04 (1H, quint, J=6.9 Hz), 7.31-7.43 (1H, m), 7.54 (1H, d, J=8.5 Hz), 7.61-7.73 (1H, m), 8.40 (1H, s).

Example 23

(cis-3-(2,4,6-trifluorophenoxy)cyclobutyl)methyl 6-oxo-7-oxa-2,5-diazaspiro[3.4]octane-2-carboxylate A) ethyl 3-(2,4,6-trifluorophenoxy)cyclobutanecarboxylate A mixture of ethyl 3-((methylsulfonyl)oxy)cyclobutanecarboxylate (1.5 g), sodium iodide (2.53 g) and acetone (15 mL) was irradiated with microwave at 130° C. for 2 hr. The insoluble substance was removed by filtration, and the filtrate was concentrated under reduced pressure. To the residue was added diisopropyl ether, the insoluble substance was removed by filtration, and the filtrate was concentrated. To the residue was added DMF (7 mL), and a mixture of 2,4,6-trifluorophenol (999 mg), potassium carbonate (2.05 g) and DMF (7 mL) was added thereto at room temperature. The mixture was stirred at 80° C. for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.04 g).

$^1$H NMR (300 MHz, DMSO-$d_6$) δ 1.18 (3H, t, J=7.2 Hz), 2.19-3.17 (5H, m), 4.03-4.13 (2H, m), 4.48-4.80 (1H, m), 7.19-7.34 (2H, m).

B) (3-(2,4,6-trifluorophenoxy)cyclobutyl)methanol

To a mixture of lithium aluminium hydride (215 mg) and THF (10 mL) was added dropwise a mixture of ethyl 3-(2,4,6-trifluorophenoxy)cyclobutanecarboxylate (1.04 g) and THF (10 mL) at 0° C. The mixture was stirred under argon atmosphere at the same temperature for 2 hr. To the mixture were added 10% aqueous potassium sodium tartrate solution and ethyl acetate at 0° C., and the insoluble substance was removed by filtration. The organic layer of the filtrate was separated, and the aqueous layer was extracted with ethyl acetate. The organic layers were combined, washed with water and saturated brine, dried over anhydrous magnesium sulfate, and concentrated under reduced pressure. The residue was purified by silica gel column chromatography (ethyl acetate/hexane) to give the title compound (566 mg).

$^1$H NMR (300 MHz, DMSO-$d_6$) δ 1.81-1.93 (1H, m), 2.05-2.40 (4H, m), 3.33-3.43 (2H, m), 4.41-4.75 (2H, m), 7.17-7.31 (2H, m).

C) (3-(2,4,6-trifluorophenoxy)cyclobutyl)methyl 6-oxo-7-oxa-2,5-diazaspiro[3.4]octane-2-carboxylate To a mixture of (3-(2,4,6-trifluorophenoxy)cyclobutyl)methanol (251 mg), TEA (0.497 mL) and acetonitrile (6 mL) was added triphosgene (112 mg) at 0° C. The reaction mixture was stirred at the same temperature for 20 min, and 7-oxa-2,5-diazaspiro[3.4]octan-6-one tosylate (325 mg) was added thereto at 0° C. The mixture was stirred at the same temperature for 1 hr. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (160 mg).

$^1$H NMR (300 MHz, DMSO-$d_6$) δ 1.82-1.94 (1H, m), 2.01-2.19 (2H, m), 2.19-2.38 (2H, m), 3.94-4.01 (4H, m), 4.05-4.13 (2H, m), 4.42-4.56 (2H, m), 4.73 (1H, quint, J=6.5 Hz), 7.18-7.32 (2H, m), 8.39 (1H, d, J=2.6 Hz).

D) (cis-3-(2,4,6-trifluorophenoxy)cyclobutyl)methyl 6-oxo-7-oxa-2,5-diazaspiro[3.4]octane-2-carboxylate (3-(2,4,6-Trifluorophenoxy)cyclobutyl)methyl 6-oxo-7-oxa-2,5-diazaspiro[3.4]octane-2-carboxylate (150 mg) was resolved by HPLC (column: CHIRALCEL OJ (trade name), 50 mmID×500 mmL, manufactured by Daicel Corporation, mobile phase: hexane/ethanol=45/55), and the fraction having a shorter retention time was concentrated. The residue was solidified from ethyl acetate/hexane to give the title compound (26.8 mg).

$^1$H NMR (300 MHz, DMSO-$d_6$) δ 1.80-1.95 (2H, m), 1.98-2.16 (1H, m), 2.27-2.39 (2H, m), 3.92-4.03 (4H, m), 4.03-4.13 (2H, m), 4.45-4.56 (3H, m), 7.18-7.33 (2H, m), 8.40 (1H, s).

Example 24

(cis-3-(2-fluoro-4-(trifluoromethyl) phenoxy)cyclobutyl)methyl 6-oxo-7-oxa-2,5-diazaspiro[3.4]octane-2-carboxylate A) ethyl cis-3-(2-fluoro-4-(trifluoromethyl)phenoxy)cyclobutanecarboxylate To a mixture of ethyl cis-3-hydroxycyclobutanecarboxylate (1 g) and DMF (10 mL) was added sodium hydride (60%, 305 mg) at 0° C. The reaction mixture was stirred under argon atmosphere at room temperature for 30 min, and a mixture of 1,2-difluoro-4-(trifluoromethyl)benzene (1.26 g) and DMF (10 mL) was added dropwise thereto at 0° C. The mixture was stirred under argon atmosphere at room temperature for 4 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (386 mg).

$^1$H NMR (300 MHz, DMSO-$d_6$) δ 1.19 (3H, t, J=7.2 Hz), 2.18-2.33 (2H, m), 2.72-2.95 (3H, m), 4.09 (2H, q, J=7.1

Hz), 4.77-4.89 (1H, m), 7.21 (1H, t, J=8.5 Hz), 7.51 (1H, d, J=8.7 Hz), 7.69 (1H, dd, J=11.5, 2.1 Hz).

B) (cis-3-(2-fluoro-4-(trifluoromethyl)phenoxy)cyclobutyl)methanol

To a mixture of lithium aluminium hydride (52.6 mg) and THF (4 mL) was added dropwise a mixture of ethyl cis-3-(2-fluoro-4-(trifluoromethyl)phenoxy)cyclobutanecarboxylate (386 mg) and THF (4 mL) at 0° C. The mixture was stirred under argon atmosphere at room temperature for 2 hr. To the mixture were added 10% aqueous potassium sodium tartrate solution and ethyl acetate at room temperature, and the insoluble substance was removed by filtration. The organic layer of the filtrate was separated, and the aqueous layer was extracted with ethyl acetate. The organic layers were combined, washed with water and saturated brine, dried over anhydrous magnesium sulfate, and concentrated under reduced pressure. The residue was purified by silica gel column chromatography (ethyl acetate/hexane) to give the title compound (367 mg) as a crude product.

$^1$H NMR (300 MHz, DMSO-$d_6$) δ 1.80-1.94 (2H, m), 2.01-2.16 (1H, m), 2.43-2.56 (2H, m), 3.40 (2H, t, J=5.5 Hz), 4.58 (1H, t, J=5.4 Hz), 4.75 (1H, quint, J=7.2 Hz), 7.20 (1H, t, J=8.5 Hz), 7.50 (1H, dd, J=8.6, 0.8 Hz), 7.66 (1H, dd, J=11.4, 2.0 Hz).

C) (cis-3-(2-fluoro-4-(trifluoromethyl)phenoxy)cyclobutyl)methyl 6-oxo-7-oxa-2,5-diazaspiro[3.4]octane-2-carboxylate To a mixture of (cis-3-(2-fluoro-4-(trifluoromethyl)phenoxy)cyclobutyl)methanol (215 mg), TEA (0.374 mL) and acetonitrile (5 mL) was added triphosgene (85 mg) at 0° C. The reaction mixture was stirred at the same temperature for 30 min, and 7-oxa-2,5-diazaspiro[3.4]octan-6-one tosylate (244 mg) was added thereto. The mixture was stirred at room temperature for 3 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (45.4 mg).

$^1$H NMR (300 MHz, DMSO-$d_6$) δ 1.80-1.95 (2H, m), 2.19-2.35 (1H, m), 2.53-2.68 (2H, m), 3.93-4.14 (6H, m), 4.47 (2H, s), 4.77 (1H, quint, J=7.1 Hz), 7.20 (1H, t, J=8.5 Hz), 7.50 (1H, d, J=8.7 Hz), 7.67 (1H, dd, J=11.4, 2.0 Hz), 8.39 (1H, s).

Example 25

(trans-3-(2,4,6-trifluorophenoxy)cyclobutyl)methyl 6-oxo-7-oxa-2,5-diazaspiro[3.4]octane-2-carboxylate (3-(2,4,6-Trifluorophenoxy)cyclobutyl)methyl 6-oxo-7-oxa-2,5-diazaspiro[3.4]octane-2-carboxylate (150 mg) was resolved by HPLC (column: CHIRALCEL OJ (trade name), 50 mmID×500 mmL, manufactured by Daicel Corporation, mobile phase: hexane/ethanol=45/55), and the fraction having a longer retention time was concentrated under reduced pressure. The residue was solidified from ethyl acetate/hexane to give the title compound (66.2 mg).

$^1$H NMR (300 MHz, DMSO-$d_6$) δ 2.07-2.19 (2H, m), 2.19-2.32 (2H, m), 3.35-3.39 (1H, m), 3.92-4.02 (4H, m), 4.05-4.12 (2H, m), 4.47 (2H, s), 4.73 (1H, quint, J=6.5 Hz), 7.18-7.34 (2H, m), 8.39 (1H, s).

Example 26

(cis-3-(2-chloro-4-(trifluoromethyl)phenoxy)cyclobutyl)methyl 6-oxo-7-oxa-2,5-diazaspiro[3.4]octane-2-carboxylate A) ethyl cis-3-(2-chloro-4-(trifluoromethyl)phenoxy)cyclobutanecarboxylate To a mixture of ethyl cis-3-hydroxycyclobutanecarboxylate (1 g) and THF (20 mL) was added sodium hydride (60%, 305 mg) at 0° C. The reaction mixture was stirred at room temperature for 30 min, and 2-chloro-1-fluoro-4-(trifluoromethyl)benzene (0.950 mL) was added thereto at 0° C. The mixture was stirred under argon atmosphere at room temperature for 2 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (352 mg).

$^1$H NMR (300 MHz, DMSO-$d_6$) δ 1.19 (3H, t, J=7.1 Hz), 2.19-2.30 (2H, m), 2.74-2.95 (3H, m), 4.09 (2H, q, J=7.1 Hz), 4.81-4.91 (1H, m), 7.17 (1H, d, J=8.7 Hz), 7.66 (1H, dd, J=8.7, 1.5 Hz), 7.84 (1H, d, J=1.7 Hz).

B) (cis-3-(2-chloro-4-(trifluoromethyl)phenoxy)cyclobutyl)methanol

To a mixture of ethyl cis-3-(2-chloro-4-(trifluoromethyl)phenoxy)cyclobutanecarboxylate (352 mg) and THF (4 mL) was added a mixture of lithium aluminium hydride (62.1 mg) and THF (4 mL) at 0° C. The mixture was stirred under argon atmosphere at room temperature for 4 hr. To the mixture were added 10% aqueous potassium sodium tartrate solution and ethyl acetate at 0° C., and the insoluble substance was removed by filtration. The organic layer of the filtrate was separated, and the aqueous layer was extracted with ethyl acetate. The organic layers were combined, washed with water and saturated brine, dried over anhydrous magnesium sulfate, and concentrated under reduced pressure. The residue was purified by silica gel column chromatography (ethyl acetate/hexane) to give the title compound (195 mg).

$^1$H NMR (300 MHz, DMSO-$d_6$) δ 1.80-1.93 (2H, m), 2.01-2.17 (1H, m), 2.44-2.56 (2H, m), 3.41 (2H, t, J=5.4 Hz), 4.59 (1H, t, J=5.5 Hz), 4.76 (1H, quint, J=7.2 Hz), 7.17 (1H, d, J=8.5 Hz), 7.64 (1H, dd, J=8.7, 1.7 Hz), 7.82 (1H, d, J=2.1 Hz).

C) (cis-3-(2-chloro-4-(trifluoromethyl)phenoxy)cyclobutyl)methyl 6-oxo-7-oxa-2,5-diazaspiro[3.4]octane-2-carboxylate To a mixture of (cis-3-(2-chloro-4-(trifluoromethyl)phenoxy)cyclobutyl)methanol (195 mg), 7-oxa-2,5-diazaspiro[3.4]octan-6-one tosylate (230 mg), TEA (0.320 mL) and THF (12 mL) was added triphosgene (72.2 mg) at 0° C. The mixture was stirred at 0° C. for 2 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and then purified by HPLC (C18, mobile phase: water/acetonitrile (containing 0.1% TFA)). To the obtained fraction was added saturated aqueous sodium hydrogencarbonate solution, and the mixture was extracted with ethyl acetate. The extract was dried over anhydrous magnesium sulfate, and concentrated under reduced pressure. The residue was solidified from ethyl acetate/hexane to give the title compound (13.2 mg).

$^1$H NMR (300 MHz, CDCl$_3$) δ 2.05-2.12 (2H, m), 2.28-2.44 (1H, m), 2.58-2.71 (2H, m), 4.09-4.13 (4H, m), 4.20-4.26 (2H, m), 4.54 (2H, s), 4.61-4.73 (1H, m), 6.73 (1H, s), 6.81 (1H, d, J=8.5 Hz), 7.44 (1H, dd, J=8.6, 1.6 Hz), 7.63 (1H, d, J=2.1 Hz).

Example 27

(trans-3-(2-chloro-4-(trifluoromethyl)phenoxy)cyclobutyl)methyl 6-oxo-7-oxa-2,5-diazaspiro[3.4]octane-2-carboxylate A) ethyl trans-3-(2-chloro-4-(trifluoromethyl)phenoxy)cyclobutanecarboxylate To a mixture of ethyl cis-3-(((4-methylphenyl)sulfonyl)oxy)cyclobutanecarboxylate (1 g), 2-chloro-4-(trifluoromethyl)phenol (725 mg) and DMF (20 mL) was added potassium carbonate (695 mg) at room temperature. The mixture was stirred at 80° C. for 16 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (473 mg).

$^1$H NMR (300 MHz, DMSO-d$_6$) δ 1.22 (3H, t, J=7.1 Hz), 2.36-2.48 (2H, m), 2.68-2.79 (2H, m), 3.14-3.26 (1H, m), 4.13 (2H, q, J=7.1 Hz), 5.02 (1H, quint, J=6.6 Hz), 7.11 (1H, d, J=8.7 Hz), 7.61-7.68 (1H, m), 7.85 (1H, d, J=1.7 Hz).

B) (trans-3-(2-chloro-4-(trifluoromethyl)phenoxy)cyclobutyl)methanol

To a mixture of ethyl trans-3-(2-chloro-4-(trifluoromethyl)phenoxy)cyclobutanecarboxylate (473 mg) and THF (5 mL) was added a mixture of lithium aluminium hydride (61.2 mg) and THF (5 mL) at 0° C. The mixture was stirred under argon atmosphere at room temperature for 1 hr. To the mixture were added 10% aqueous potassium sodium tartrate solution and ethyl acetate at 0° C. The insoluble substance was removed by filtration, the organic layer of the filtrate was separated, and the aqueous layer was extracted with ethyl acetate. The organic layers were combined, washed with water and saturated brine, dried over anhydrous magnesium sulfate, and concentrated under reduced pressure. The residue was purified by silica gel column chromatography (ethyl acetate/hexane) to give the title compound (277 mg).

$^1$H NMR (300 MHz, DMSO-d$_6$) δ 2.10-2.24 (2H, m), 2.28-2.45 (3H, m), 3.48 (2H, t, J=5.8 Hz), 4.69 (1H, t, J=5.3 Hz), 4.94 (1H, quint, J=6.5 Hz), 7.08 (1H, d, J=8.5 Hz), 7.61-7.68 (1H, m), 7.83 (1H, d, J=1.7 Hz).

C) (trans-3-(2-chloro-4-(trifluoromethyl)phenoxy)cyclobutyl)methyl 6-oxo-7-oxa-2,5-diazaspiro[3.4]octane-2-carboxylate To a mixture of 7-oxa-2,5-diazaspiro[3.4]octan-6-one tosylate (296 mg), (trans-3-(2-chloro-4-(trifluoromethyl)phenoxy)cyclobutyl)methanol (277 mg), TEA (0.454 mL) and THF (6 mL) was added triphosgene (103 mg) at 0° C. The mixture was stirred at room temperature for 2 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/diisopropyl ether/hexane to give the title compound (29.7 mg).

$^1$H NMR (300 MHz, DMSO-d$_6$) δ 2.19-2.29 (2H, m), 2.31-2.40 (2H, m), 2.54-2.66 (1H, m), 3.97-4.17 (6H, m), 4.49 (2H, s), 5.00 (1H, quint, J=6.6 Hz), 7.10 (1H, d, J=8.7 Hz), 7.66 (1H, dd, J=8.7, 1.7 Hz), 7.84 (1H, d, J=1.9 Hz), 8.42 (1H, s).

Example 28 cis-3-(((3-chloro-4-methylbenzyl)oxy)methyl)cyclobutyl 6-oxo-7-oxa-2,5-diazaspiro[3.4]octane-2-carboxylate A) cis-3-(((3-chloro-4-methylbenzyl)oxy)methyl)cyclobutanol To a mixture of (cis-3-((tert-butyl(diphenyl)silyl)oxy)cyclobutyl)methanol (395 mg) and DMF (5 mL) was added sodium hydride (60%, 60.3 mg) at 0° C. The reaction mixture was stirred at the same temperature for 15 min, and a mixture of 4-(bromomethyl)-2-chloro-1-methylbenzene (280 mg) and DMF (2 mL) was added thereto. The mixture was stirred at room temperature for 2 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give an intermediate (317 mg) as a crude product. To a mixture of the obtained intermediate (crude product, 316 mg) and THF (6.6 mL) was added TBAF (1 M THF solution, 0.79 mL) at 0° C. The reaction mixture was stirred overnight at room temperature, and TBAF (1 M THF solution, 0.33 mL) was added thereto at 0° C. The mixture was stirred at room temperature for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (83.9 mg).

$^1$H NMR (300 MHz, DMSO-d$_6$) δ 1.42-1.58 (2H, m), 1.80-1.99 (1H, m), 2.10-2.28 (2H, m), 2.31 (3H, s), 3.34 (2H, d, J=6.2 Hz), 3.85-3.99 (1H, m), 4.41 (2H, s), 4.92 (1H, d, J=6.6 Hz), 7.17 (1H, dd, J=7.6, 1.4 Hz), 7.28-7.41 (2H, m).

B) cis-3-(((3-chloro-4-methylbenzyl)oxy)methyl)cyclobutyl 6-oxo-7-oxa-2,5-diazaspiro[3.4]octane-2-carboxylate To a mixture of cis-3-(((3-chloro-4-methylbenzyl)oxy)methyl)cyclobutanol (83 mg), TEA (0.192 mL) and acetonitrile (3.5 mL) was added triphosgene (43.0 mg) at 0° C. The reaction mixture was stirred at the same temperature for 30 min, and 7-oxa-2,5-diazaspiro[3.4]octan-6-one tosylate (104 mg) was added thereto at 0° C. The mixture was stirred overnight at room temperature. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (69.9 mg).

$^1$H NMR (300 MHz, DMSO-$d_6$) δ 1.65-1.82 (2H, m), 2.11 (1H, d, J=6.8 Hz), 2.25-2.40 (5H, m), 3.38 (2H, d, J=5.9 Hz), 3.87-4.15 (4H, m), 4.44 (4H, d, J=10.0 Hz), 4.72 (1H, t, J=7.5 Hz), 7.13-7.22 (1H, m), 7.28-7.38 (2H, m), 8.37 (1H, s).

Example 29 cis-3-(((4-chloro-3-methylbenzyl)oxy)methyl)cyclobutyl 6-oxo-7-oxa-2,5-diazaspiro [3.4]octane-2-carboxylate A) cis-3-(((4-chloro-3-methylbenzyl)oxy)methyl) cyclobutanol To a mixture of (cis-3-((tert-butyl(diphenyl)silyl)oxy)cyclobutyl)methanol (0.8 g) and DMF (20 mL) was added sodium hydride (60%, 122 mg) at 0° C. The reaction mixture was stirred at the same temperature for 15 min, and a mixture of 4-(bromomethyl)-1-chloro-2-methylbenzene (567 mg) and DMF (2 mL) was added thereto. The mixture was stirred at room temperature for 2 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give an intermediate (770 mg) as a crude product. To a mixture of the obtained intermediate (crude product, 769 mg) and THF (16 mL) was added TBAF (1 M THF solution, 2.4 mL) at 0° C. The reaction mixture was stirred overnight at room temperature, and TBAF (1 M THF solution, 0.80 mL) was added thereto. The mixture was stirred at room temperature for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (241 mg).

$^1$H NMR (300 MHz, DMSO-$d_6$) δ1.41-1.61 (2H, m), 1.81-2.02 (1H, m), 2.10-2.27 (2H, m), 2.32 (3H, s), 3.35 (2H, d, J=6.2 Hz), 3.81-4.02 (1H, m), 4.40 (2H, s), 4.92 (1H, d, J=6.6 Hz), 7.15 (1H, dd, J=8.1, 1.7 Hz), 7.28 (1H, d, J=1.1 Hz), 7.37 (1H, d, J=8.1 Hz).

B) cis-3-(((4-chloro-3-methylbenzyl)oxy)methyl) cyclobutyl 6-oxo-7-oxa-2,5-diazaspiro[3.4]octane-2-carboxylate To a mixture of cis-3-(((4-chloro-3-methylbenzyl)oxy) methyl)cyclobutanol (241 mg), TEA (0.558 mL) and acetonitrile (10 mL) was added triphosgene (125 mg) at 0° C. The reaction mixture was stirred at the same temperature for 30 min, and 7-oxa-2,5-diazaspiro[3.4]octan-6-one tosylate (301 mg) was added thereto at 0° C. The mixture was stirred overnight at room temperature. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (291 mg).

$^1$H NMR (300 MHz, DMSO-$d_6$) δ 1.65-1.84 (2H, m), 2.03-2.20 (1H, m), 2.24-2.40 (5H, m), 3.38 (2H, d, J=5.9 Hz), 3.87-4.15 (4H, m), 4.42 (2H, s), 4.46 (2H, s), 4.72 (1H, t, J=7.6 Hz), 7.15 (1H, dd, J=8.2, 1.6 Hz), 7.28 (1H, s), 7.38 (1H, d, J=8.1 Hz), 8.37 (1H, s).

Example 30 cis-3-(((2-chloro-4-fluorobenzyl)oxy)methyl)cyclobutyl 6-oxo-7-oxa-2,5-diazaspiro[3.4]octane-2-carboxylate A) tert-butyl((cis-3-(((2-chloro-4-fluorobenzyl)oxy) methyl)cyclobutyl)oxy)dimethylsilane To a mixture of (cis-3-((tert-butyl(dimethyl)silyl)oxy)cyclobutyl)methanol (400 mg) and DMF (4.0 mL) was added sodium hydride (60%, 89.0 mg) at 0° C. The reaction mixture was stirred at the same temperature for 10 min, and 1-(bromomethyl)-2-chloro-4-fluorobenzene (496 mg) was added thereto at 0° C. The mixture was stirred at room temperature for 3 hr. To the mixture was added water, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (602 mg).

$^1$H NMR (300 MHz, DMSO-$d_6$) δ 0.01 (6H, s), 0.84 (9H, s), 1.49-1.73 (2H, m), 1.86-2.13 (1H, m), 2.19-2.38 (2H, m), 3.43 (2H, d, J=6.0 Hz), 4.12 (1H, quint, J=7.3 Hz), 4.49 (2H, s), 7.16-7.33 (1H, m), 7.39-7.55 (2H, m).

B) cis-3-(((2-chloro-4-fluorobenzyl)oxy)methyl) cyclobutanol

To a mixture of tert-butyl((cis-3-(((2-chloro-4-fluorobenzyl)oxy)methyl)cyclobutyl)oxy)dimethylsilane (600 mg) and THF (5.0 mL) was added TBAF (1 M THF solution, 2.0 mL). The mixture was stirred overnight at room temperature. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (364 mg).

$^1$H NMR (300 MHz, DMSO-$d_6$) δ 1.46-1.63 (2H, m), 1.85-2.03 (1H, m), 2.16-2.31 (2H, m), 3.42 (2H, d, J=6.4 Hz), 3.78-3.99 (1H, m), 4.49 (2H, s), 4.94 (1H, d, J=6.4 Hz), 7.24 (1H, td, J=8.5, 2.6 Hz), 7.44 (1H, dd, J=8.7, 2.6 Hz), 7.52 (1H, dd, J=8.7, 6.4 Hz).

C) cis-3-(((2-chloro-4-fluorobenzyl)oxy)methyl) cyclobutyl 6-oxo-7-oxa-2,5-diazaspiro[3.4]octane-2-carboxylate To a mixture of cis-3-(((2-chloro-4-fluorobenzyl)oxy) methyl)cyclobutanol (240 mg), TEA (0.818 mL) and acetonitrile (4.0 mL) was added triphosgene (102 mg) at 0°

C. The reaction mixture was stirred at the same temperature for 20 min, and 7-oxa-2,5-diazaspiro[3.4]octan-6-one tosylate (309 mg) was added thereto. The mixture was stirred overnight at room temperature. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), and solidified from ethyl acetate/hexane to give the title compound (301 mg).

$^1$H NMR (300 MHz, DMSO-$d_6$) δ 1.68-1.85 (2H, m), 2.06-2.23 (1H, m), 2.26-2.42 (2H, m), 3.46 (2H, d, J=6.0 Hz), 3.89-4.18 (4H, m), 4.49 (4H, d, J=12.1 Hz), 4.73 (1H, quint, J=7.5 Hz), 7.24 (1H, td, J=8.5, 2.6 Hz), 7.40-7.61 (2H, m), 8.38 (1H, s).

Example 31 cis-3-(((2,3,4-trifluorobenzyl)oxy)methyl)cyclobutyl 6-oxo-7-oxa-2,5-diazaspiro[3.4]octane-2-carboxylate A) cis-3-(((2,3,4-trifluorobenzyl)oxy)methyl)cyclobutanol To a mixture of (cis-3-((tert-butyl(diphenyl)silyl)oxy)cyclobutyl)methanol (1.01 g) and DMF (15 mL) was added sodium hydride (60%, 154 mg) at 0° C. The reaction mixture was stirred at the same temperature for 15 min, and 1-(bromomethyl)-2,3,4-trifluorobenzene (734 mg) was added thereto. The mixture was stirred at room temperature for 2 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give an intermediate (1.08 g) as a crude product. To a mixture of the obtained intermediate (crude product, 1.08 g) and THF (22 mL) was added TBAF (1 M THF solution, 3.3 mL) at 0° C. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (291 mg).

$^1$H NMR (300 MHz, DMSO-$d_6$) δ 1.39-1.60 (2H, m), 1.77-2.00 (1H, m), 2.14-2.33 (2H, m), 3.38 (2H, d, J=6.2 Hz), 3.79-3.98 (1H, m), 4.50 (2H, s), 4.92 (1H, d, J=6.6 Hz), 7.13-7.45 (2H, m).

B) cis-3-(((2,3,4-trifluorobenzyl)oxy)methyl)cyclobutyl 6-oxo-7-oxa-2,5-diazaspiro[3.4]octane-2-carboxylate To a mixture of cis-3-(((2,3,4-trifluorobenzyl)oxy)methyl)cyclobutanol (290 mg), TEA (0.657 mL) and acetonitrile (12 mL) was added triphosgene (147 mg) at 0° C. The reaction mixture was stirred at room temperature for 30 min, and 7-oxa-2,5-diazaspiro[3.4]octan-6-one tosylate (354 mg) was added thereto at 0° C. The mixture was stirred overnight at room temperature. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (351 mg).

$^1$H NMR (300 MHz, DMSO-$d_6$) δ 1.64-1.83 (2H, m), 1.99-2.19 (1H, m), 2.21-2.43 (2H, m), 3.37-3.52 (2H, m), 3.83-4.19 (4H, m), 4.36-4.58 (4H, m), 4.72 (1H, quint, J=7.5 Hz), 7.17-7.42 (2H, m), 8.38 (1H, s).

Example 32 cis-3-(((2,4,5-trifluorobenzyl)oxy)methyl)cyclobutyl 6-oxo-7-oxa-2,5-diazaspiro [3.4]octane-2-carboxylate A) tert-butyl(diphenyl) ((cis-3-(((2,4,5-trifluorobenzyl)oxy)methyl)cyclobutyl)oxy)silane To a mixture of (cis-3-((tert-butyl(diphenyl)silyl)oxy)cyclobutyl)methanol (1.00 g) and DMF (15 mL) was added sodium hydride (60%, 129 mg) at 0° C. The reaction mixture was stirred at the same temperature for 15 min, and 1-(bromomethyl)-2,4,5-trifluorobenzene (793 mg) was added thereto. The mixture was stirred at room temperature for 3 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (981 mg).

$^1$H NMR (300 MHz, DMSO-$d_6$) δ 0.97 (9H, s), 1.61-1.80 (2H, m), 1.81-1.97 (1H, m), 2.07-2.25 (2H, m), 3.40 (2H, d, J=6.0 Hz), 4.06-4.19 (1H, m), 4.45 (2H, s), 7.36-7.67 (12H, m).

B) cis-3-(((2,4,5-trifluorobenzyl)oxy)methyl)cyclobutanol

To a mixture of tert-butyl(diphenyl) ((cis-3-(((2,4,5-trifluorobenzyl)oxy)methyl)cyclobutyl)oxy)silane (981 mg) and THF (4 mL) was added TBAF (1 M THF solution, 3.0 mL) at room temperature. The mixture was stirred at room temperature for 4 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (296 mg).

$^1$H NMR (300 MHz, DMSO-$d_6$) δ 1.40-1.59 (2H, m), 1.85-1.98 (1H, m), 2.13-2.31 (2H, m), 3.39 (2H, d, J=6.2 Hz), 3.82-3.98 (1H, m), 4.45 (2H, s), 4.92 (1H, d, J=6.6 Hz), 7.38-7.64 (2H, m).

C) cis-3-(((2,4,5-trifluorobenzyl)oxy)methyl)cyclobutyl 6-oxo-7-oxa-2,5-diazaspiro[3.4]octane-2-carboxylate To a mixture of cis-3-(((2,4,5-trifluorobenzyl)oxy)methyl)cyclobutanol (301 mg), TEA (0.68 mL) and acetonitrile (5 mL) was added triphosgene (127 mg) at 0° C. The reaction mixture was stirred at the same temperature for 30 min, and 7-oxa-2,5-diazaspiro[3.4]octan-6-one tosylate (385 mg) was added thereto. The mixture was stirred overnight at room temperature. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and solidified from ethyl acetate/hexane to give the title compound (105 mg).

$^1$H NMR (300 MHz, DMSO-$d_6$) δ 1.65-1.81 (2H, m), 2.02-2.20 (1H, m), 2.26-2.37 (2H, m), 3.42 (2H, d, J=5.9 Hz), 3.90-4.00 (2H, m), 4.02-4.12 (2H, m), 4.46 (2H, s), 4.47 (2H, s), 4.72 (1H, quint, J=7.4 Hz), 7.35-7.71 (2H, m), 8.37 (1H, s).

Example 33 cis-3-(((2,4,6-trifluorobenzyl)oxy)methyl)cyclobutyl 6-oxo-7-oxa-2,5-diazaspiro[3.4]octane-2-carboxylate

A) cis-3-(((2,4,6-trifluorobenzyl)oxy)methyl)cyclobutanol

To a mixture of (cis-3-((tert-butyl(diphenyl)silyl)oxy)cyclobutyl)methanol (804 mg) and DMF (10 mL) was added sodium hydride (60%, 123 mg) at 0° C. The reaction mixture was stirred at the same temperature for 15 min, and a mixture of 2-(bromomethyl)-1,3,5-trifluorobenzene (584 mg) and DMF (2 mL) was added thereto. The mixture was stirred at room temperature for 2 hr. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give an intermediate (1.11 g) as a crude product. To a mixture of the obtained intermediate (crude product, 1.1 g) and THF (11 mL) was added TBAF (1 M THF solution, 4.5 mL) at 0° C. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (82 mg).

$^1$H NMR (300 MHz, DMSO-$d_6$) δ 1.29-1.56 (2H, m), 1.77-1.95 (1H, m), 2.12-2.30 (2H, m), 3.35 (2H, d, J=6.2 Hz), 3.79-4.05 (1H, m), 4.44 (2H, s), 4.90 (1H, d, J=6.6 Hz), 7.21 (2H, dd, J=9.3, 8.0 Hz).

B) cis-3-(((2,4,6-trifluorobenzyl)oxy)methyl)cyclobutyl 6-oxo-7-oxa-2,5-diazaspiro[3.4]octane-2-carboxylate To a mixture of cis-3-(((2,4,6-trifluorobenzyl)oxy)methyl)cyclobutanol (352 mg), TEA (0.797 mL) and acetonitrile (14 mL) was added triphosgene (178 mg) at 0° C. The reaction mixture was stirred at the same temperature for 30 min, and 7-oxa-2,5-diazaspiro[3.4]octan-6-one tosylate (429 mg) was added thereto at 0° C. The mixture was stirred overnight at room temperature. To the mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and solidified from ethyl acetate/hexane to give the title compound (409 mg).

$^1$H NMR (300 MHz, DMSO-$d_6$) δ 1.59-1.78 (2H, m), 2.01-2.17 (1H, m), 2.22-2.36 (2H, m), 3.39 (2H, d, J=6.0 Hz), 3.90-3.98 (2H, m), 4.01-4.13 (2H, m), 4.42-4.50 (4H, m), 4.70 (1H, quint, J=7.6 Hz), 7.11-7.34 (2H, m), 8.37 (1H, s).

Example 39 trans-3-(2,3,4-trifluorophenoxy)cyclobutyl 6-oxo-7-oxa-2,5-diazaspiro[3.4]octane-2-carboxylate

A) 1-((trans-3-(benzyloxy)cyclobutyl)oxy)-2,3,4-trifluorobenzene

To a mixture of cis-3-(benzyloxy)cyclobutanol (250 mg), 2,3,4-trifluorophenol (249 mg), triphenylphosphine (552 mg) and THF (5.0 mL) was added DIAD (40% toluene solution, 1.14 mL) at room temperature. The mixture was stirred at 60° C. for 3 hr. The reaction mixture was concentrated under reduced pressure, and the residue was purified by silica gel column chromatography (ethyl acetate/hexane) to give the title compound (426 mg).

$^1$H NMR (300 MHz, DMSO-$d_6$) δ 2.28-2.41 (2H, m), 2.46 (2H, dd, J=6.8, 4.5 Hz), 4.28 (1H, tt, J=7.0, 4.7 Hz), 4.40 (2H, s), 4.94 (1H, tt, J=6.9, 4.2 Hz), 6.84 (1H, tdd, J=9.2, 4.5, 2.6 Hz), 7.12-7.48 (6H, m).

B) trans-3-(2,3,4-trifluorophenoxy)cyclobutanol

A mixture of 1-((trans-3-(benzyloxy)cyclobutyl)oxy)-2,3,4-trifluorobenzene (417 mg), palladium hydroxide/carbon (Pd 20%, 50% hydrous, 40.0 mg) and ethyl acetate (6.0 mL) was stirred overnight under normal pressure of hydrogen atmosphere at room temperature. The catalyst was removed by filtration, and the filtrate was concentrated under reduced pressure. The residue was purified by silica gel column chromatography (ethyl acetate/hexane) to give the title compound (287 mg).

$^1$H NMR (300 MHz, DMSO-$d_6$) δ 2.19-2.41 (4H, m), 4.28-4.44 (1H, m), 4.85-4.97 (1H, m), 5.20 (1H, d, J=5.3 Hz), 6.80 (1H, tdd, J=9.2, 4.8, 2.6 Hz), 7.12-7.31 (1H, m).

C) trans-3-(2,3,4-trifluorophenoxy)cyclobutyl 6-oxo-7-oxa-2,5-diazaspiro[3.4]octane-2-carboxylate To a mixture of trans-3-(2,3,4-trifluorophenoxy)cyclobutanol (280 mg), TEA (0.892 mL) and THF (6.0 mL) was added triphosgene (133 mg) at 0° C. The reaction mixture was stirred at the same temperature for 30 min, and 7-oxa-2,5-diazaspiro[3.4]octan-6-one tosylate (385 mg) was added thereto at 0° C. The mixture was stirred at room temperature for 2 days. The mixture was passed through NH silica gel, eluted with ethyl acetate/methanol (10/1), and crystallized from ethyl acetate/diisopropyl ether to give the title compound (405 mg).

$^1$H NMR (300 MHz, CDCl$_3$) δ 2.44-2.77 (4H, m), 4.05-4.28 (4H, m), 4.56 (2H, s), 4.78-4.93 (1H, m), 5.19 (1H, tt, J=7.2, 4.5 Hz), 6.02 (1H, s), 6.33-6.58 (1H, m), 6.71-6.96 (1H, m).

Example 44 cis-3-(2-chloro-4-fluorophenoxy)cyclobutyl 6-oxo-7-oxa-2,5-diazaspiro[3.4]octane-2-carboxylate

A) trans-3-(benzyloxy)cyclobutyl 6-oxo-7-oxa-2,5-diazaspiro[3.4]octane-2-carboxylate A mixture of trans-3-(benzyloxy)cyclobutanol (9.65 g), TEA (37.6 mL) and THF (120 mL) was cooled to −10° C.

in an ice salt bath. While keeping the internal temperature of the reaction mixture 5° C. or below, a mixture of triphosgene (5.62 g) and THF (40 mL) was added dropwise thereto over 30 min. To the reaction mixture was added THF (50 mL), the mixture was stirred at −10° C. for 30 min, and 7-oxa-2,5-diazaspiro[3.4]octan-6-one tosylate (16.3 g) was added thereto by small and small. The reaction mixture was stirred at 0° C. for 1 hr, and then at room temperature for 3 days. The reaction mixture was diluted with water, and extracted with ethyl acetate. The organic layer was separated, washed with saturated brine, dried over anhydrous sodium sulfate, and concentrated under reduced pressure. The residue was purified by silica gel column chromatography (ethyl acetate/hexane), and solidified from ethyl acetate/diisopropyl ether to give the title compound (15.6 g).

$^1$H NMR (300 MHz, DMSO-$d_6$) δ 2.15-2.41 (4H, m), 3.91-4.13 (4H, m), 4.15-4.27 (1H, m), 4.37 (2H, s), 4.47 (2H, s), 4.87-5.02 (1H, m), 7.21-7.46 (5H, m), 8.39 (1H, s).

B) trans-3-hydroxycyclobutyl 6-oxo-7-oxa-2,5-diazaspiro[3.4]octane-2-carboxylate To a mixture of trans-3-(benzyloxy)cyclobutyl 6-oxo-7-oxa-2,5-diazaspiro[3.4]octane-2-carboxylate (7.50 g), ethyl acetate (50 mL) and methanol (50 mL) was added palladium hydroxide/carbon (Pd 20%, 50% hydrous, 750 mg) under nitrogen atmosphere at room temperature. The reaction mixture was stirred under normal pressure of hydrogen atmosphere at room temperature for 4 hr. The catalyst was removed by filtration, and the filtrate was concentrated under reduced pressure to give the title compound (5.47 g).

$^1$H NMR (300 MHz, DMSO-$d_6$) δ 2.07-2.27 (4H, m), 3.91-4.15 (4H, m), 4.22-4.36 (1H, m), 4.47 (2H, s), 4.85-4.99 (1H, m), 5.11 (1H, d, J=5.3 Hz), 8.40 (1H, s).

C) cis-3-(2-chloro-4-fluorophenoxy)cyclobutyl 6-oxo-7-oxa-2,5-diazaspiro[3.4]octane-2-carboxylate To a mixture of trans-3-hydroxycyclobutyl 6-oxo-7-oxa-2,5-diazaspiro[3.4]octane-2-carboxylate (250 mg), 2-chloro-4-fluorophenol (0.165 mL), triphenylphosphine (polymer-supported, 3 mmol/g, 1.03 g) and THF (5.0 mL) was added DIAD (0.305 mL) at room temperature. The mixture was stirred at 60° C. for 3 hr. The reaction mixture was passed through NH silica gel, and eluted with ethyl acetate/methanol (10/1), and the filtrate was concentrated under reduced pressure. The residue was purified by silica gel column chromatography (ethyl acetate/hexane), solidified from ethyl acetate/diisopropyl ether, washed with ethyl acetate/diisopropyl ether (1/10), and dried under reduced pressure at 80° C. for 2 hr to give the title compound (245 mg).

$^1$H NMR (300 MHz, DMSO-$d_6$) δ 1.99-2.20 (2H, m), 2.90-3.06 (2H, m), 3.88-4.22 (4H, m), 4.40-4.53 (3H, m), 4.63 (1H, quint, J=7.1 Hz), 6.94-7.07 (1H, m), 7.15 (1H, td, J=8.6, 3.0 Hz), 7.44 (1H, dd, J=8.3, 3.0 Hz), 8.39 (1H, s).

Example 46 cis-3-(2,4,6-trifluorophenoxy)cyclobutyl 6-oxo-7-oxa-2,5-diazaspiro[3.4]octane-2-carboxylate To a mixture of trans-3-hydroxycyclobutyl 6-oxo-7-oxa-2,5-diazaspiro[3.4]octane-2-carboxylate (250 mg), 2,4,6-trifluorophenol (229 mg), triphenylphosphine (polymer-supported, 3 mmol/g, 1.03 g) and THF (5.0 mL) was added DIAD (0.305 mL) at room temperature. The mixture was stirred at the same temperature for 1 hr, and then at 60° C. for 1 hr. The reaction mixture was passed through NH silica gel, and eluted with ethyl acetate/methanol (9/1), and the filtrate was concentrated under reduced pressure. The residue was purified by silica gel column chromatography (ethyl acetate/hexane), and crystallized from ethyl acetate/diisopropyl ether to give the title compound (327 mg).

$^1$H NMR (300 MHz, DMSO-$d_6$) δ 2.05-2.25 (2H, m), 2.67-2.86 (2H, m), 3.90-4.19 (4H, m), 4.34 (1H, quint, J=6.9 Hz), 4.43-4.56 (3H, m), 7.20-7.40 (2H, m), 8.40 (1H, s). mp 160° C.

powder X-RAY crystal diffraction pattern (diffraction angle 2θ): 4.10, 8.2°, 12.3°, 16.4°, 18.6°, 21.5°, 23.4° and 24.7°

Example 50 cis-3-(4-fluoro-3-methylphenoxy)cyclobutyl 6-oxo-7-oxa-2,5-diazaspiro[3.4]octane-2-carboxylate To a mixture of trans-3-hydroxycyclobutyl 6-oxo-7-oxa-2,5-diazaspiro[3.4]octane-2-carboxylate (250 mg), 4-fluoro-3-methylphenol (0.172 mL), triphenylphosphine (polymer-supported, 3 mmol/g, 1.03 g) and THF (5.0 mL) was added DIAD (0.305 mL) at room temperature. The mixture was stirred at the same temperature for 1 hr, and then at 60° C. for 1 hr. The reaction mixture was passed through NH silica gel, and eluted with ethyl acetate/methanol (9/1), and the filtrate was concentrated under reduced pressure. The residue was purified by silica gel column chromatography (ethyl acetate/hexane), and solidified from ethyl acetate/diisopropyl ether to give a crude product (257 mg). The obtained crude product (243 mg) was recrystallized from ethanol/water to give the title compound (216 mg).

$^1$H NMR (300 MHz, DMSO-$d_6$) δ1.92-2.11 (2H, m), 2.19 (3H, d, J=1.9 Hz), 2.83-3.05 (2H, m), 3.92-4.21 (4H, m), 4.36 (1H, quint, J=6.7 Hz), 4.47 (2H, s), 4.61 (1H, quint, J=7.2 Hz), 6.66 (1H, dt, J=8.7, 3.6 Hz), 6.76 (1H, dd, J=6.5, 2.9 Hz), 7.02 (1H, t, J=9.2 Hz), 8.40 (1H, s).

Example 63 cis-3-(2-chloro-4-fluorophenoxy)-3-methylcyclobutyl 6-oxo-7-oxa-2,5-diazaspiro[3.4]octane-2-carboxylate A) 1-((3-(benzyloxy)-1-methylcyclobutyl)oxy)-4-fluoro-2-nitrobenzene To a mixture of 3-(benzyloxy)-1-methylcyclobutanol (0.89 g) and DMF (10 mL) was added sodium hydride (60%, 204 mg) under argon atmosphere at 0° C. The reaction mixture was stirred at the same temperature for 30 min, and 1,4-difluoro-2-nitrobenzene (0.552 mL) was added thereto at 0° C. The mixture was stirred under argon atmosphere at room temperature for 1 hr, 60° C. for 3 hr, and then overnight at room temperature. To the reaction mixture was added 0.1 M hydrochloric acid, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) and then purified by NH silica gel column chromatography (ethyl acetate/hexane) to give the title compound (629 mg).

$^1$H NMR (300 MHz, DMSO-$d_6$) δ 1.45 (3H, s), 2.17-2.27 (2H, m), 2.61-2.70 (2H, m), 3.89 (1H, quint, J=6.9 Hz), 4.39

(2H, s), 7.17 (1H, dd, J=9.4, 4.5 Hz), 7.24-7.39 (5H, m), 7.43-7.52 (1H, m), 7.86 (1H, dd, J=7.9, 3.2 Hz).

B) 2-((3-(benzyloxy)-1-methylcyclobutyl)oxy)-5-fluoroaniline

A mixture of 1-((3-(benzyloxy)-1-methylcyclobutyl)oxy)-4-fluoro-2-nitrobenzene (629 mg), palladium/carbon (ethylene diamine complex, Pd 3.5-6.5%, 202 mg) and methanol (12 mL) was stirred overnight under normal pressure of hydrogen atmosphere at room temperature. The catalyst was removed by filtration, and the filtrate was concentrated under reduced pressure to give the title compound (483 mg).

$^1$H NMR (300 MHz, DMSO-$d_6$) δ 1.33-1.41 (3H, m), 2.14-2.24 (2H, m), 2.42-2.48 (2H, m), 3.81 (1H, quint, J=6.9 Hz), 4.36 (2H, s), 4.97 (2H, s), 6.19 (1H, td, J=8.6, 3.1 Hz), 6.43 (1H, dd, J=10.9, 3.1 Hz), 6.61 (1H, dd, J=8.7, 5.7 Hz), 7.24-7.37 (5H, m).

C) 1-((3-(benzyloxy)-1-methylcyclobutyl)oxy)-2-chloro-4-fluorobenzene

To a mixture of 2-((3-(benzyloxy)-1-methylcyclobutyl)oxy)-5-fluoroaniline (483 mg) and hydrochloric acid (6 M, 10 mL) was added a mixture of sodium nitrite (133 mg) and water (1 mL) at 0° C. The reaction mixture was stirred at the same temperature for 30 min, and copper chloride (I) (190 mg) was added thereto at 0° C. The mixture was stirred at the same temperature for 3 hr. To the reaction mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (209 mg).

$^1$H NMR (300 MHz, DMSO-$d_6$) δ 1.42 (3H, s), 2.15-2.27 (2H, m), 2.55-2.65 (2H, m), 3.87 (1H, quint, J=6.9 Hz), 4.38 (2H, s), 6.98-7.05 (1H, m), 7.09-7.17 (1H, m), 7.25-7.38 (5H, m), 7.44 (1H, dd, J=8.5, 3.0 Hz).

D) cis-3-(2-chloro-4-fluorophenoxy)-3-methylcyclobutyl 6-oxo-7-oxa-2,5-diazaspiro[3.4]octane-2-carboxylate To a mixture of sodium iodide (187 mg) and acetonitrile (2 mL) was added chlorotrimethylsilane (0.159 mL) at 0° C. The mixture was stirred at the same temperature for 30 min, and a mixture of 1-((3-(benzyloxy)-1-methylcyclobutyl)oxy)-2-chloro-4-fluorobenzene (200 mg) and acetonitrile (2 mL) was added thereto at 0° C. The mixture was stirred at 0° C. for 1 hr, and then overnight at room temperature. To the reaction mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give an intermediate (93 mg). To a mixture of the obtained intermediate (93 mg), TEA (0.287 mL) and acetonitrile (2 mL) was added triphosgene (64.8 mg) at 0° C. The reaction mixture was stirred at the same temperature for 30 min, and 7-oxa-2,5-diazaspiro[3.4]octan-6-one tosylate (187 mg) was added thereto at 0° C. The mixture was stirred at room temperature for 3 hr. To the reaction mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane). The residue was purified by HPLC (C18, mobile phase: water/acetonitrile (containing 0.1% TFA)). To the obtained fraction was added saturated aqueous sodium hydrogencarbonate solution, and the mixture was extracted with ethyl acetate. The extract was dried over anhydrous magnesium sulfate, and concentrated under reduced pressure. The residue was solidified from ethyl acetate/hexane to give the title compound (74.7 mg).

$^1$H NMR (300 MHz, DMSO-$d_6$) δ 1.45 (3H, s), 2.24-2.37 (2H, m), 2.65-2.76 (2H, m), 3.91-4.01 (2H, m), 4.01-4.13 (2H, m), 4.46 (2H, s), 4.68 (1H, quint, J=7.1 Hz), 6.97-7.05 (1H, m), 7.08-7.17 (1H, m), 7.45 (1H, dd, J=8.4, 3.1 Hz), 8.37 (1H, s).

The compounds of Examples are shown in the following Table 1. MS in the tables means actual measured value. The compounds of Examples 34 to 38, 40 to 43, 45, 47 to 49, 51 to 62 and 64 in the following tables were produced according to the methods described in the above-mentioned Examples, or methods analogous thereto.

TABLE 1

| Ex.No. | IUPAC name | structure formula | MS |
|---|---|---|---|
| 1 | cis-3-(2-fluoro-4-(trifluoromethyl)phenoxy)cyclobutyl 6-oxo-7-oxa-2,5-diazaspiro[3.4]octane-2-carboxylate | | 402.9 |

TABLE 1-continued

| Ex.No. | IUPAC name | structure formula | MS |
|---|---|---|---|
| 2 | cis-3-(benzyloxy)cyclobutyl 6-oxo-7-oxa-2,5-diazaspiro[3.4]octane-2-carboxylate | | 331.1 |
| 3 | cis-3-((3-chloro-4-methylbenzyl)oxy)cyclobutyl 6-oxo-7-oxa-2,5-diazaspiro[3.4]octane-2-carboxylate | | 379.0 |
| 4 | cis-3-((4-chloro-3-methylbenzyl)oxy)cyclobutyl 6-oxo-7-oxa-2,5-diazaspiro[3.4]octane-2-carboxylate | | 378.9 |
| 5 | cis-3-((2,3-difluoro-4-methylbenzyl)oxy)cyclobutyl 6-oxo-7-oxa-2,5-diazaspiro[3.4]octane-2-carboxylate | | 380.9 |
| 6 | cis-3-((2,3,4-trifluorobenzyl)oxy)cyclobutyl 6-oxo-7-oxa-2,5-diazaspiro[3.4]octane-2-carboxylate | | 384.9 |

TABLE 1-continued

| Ex.No. | IUPAC name | structure formula | MS |
|---|---|---|---|
| 7 | cis-3-((2,4,5-trifluorobenzyl)oxy)cyclobutyl 6-oxo-7-oxa-2,5-diazaspiro[3.4]octane-2-carboxylate | | 385.0 |
| 8 | cis-3-((2,4,6-trifluorobenzyl)oxy)cyclobutyl 6-oxo-7-oxa-2,5-diazaspiro[3.4]octane-2-carboxylate | | 384.9 |
| 9 | cis-3-((3,4-dichlorobenzyl)oxy)cyclobutyl 6-oxo-7-oxa-2,5-diazaspiro[3.4]octane-2-carboxylate | | 398.8 |
| 10 | cis-3-((2-fluoro-4-(trifluoromethyl)benzyl)oxy)cyclobutyl 6-oxo-7-oxa-2,5-diazaspiro[3.4]octane-2-carboxylate | | 416.9 |
| 11 | cis-3-((3-chloro-4-(trifluoromethyl)benzyl)oxy)cyclobutyl 6-oxo-7-oxa-2,5-diazaspiro[3.4]octane-2-carboxylate | | 432.8 |
| 12 | cis-3-((2-fluoro-4-methylphenoxy)methyl)cyclobutyl 6-oxo-7-oxa-2,5-diazaspiro[3.4]octane-2-carboxylate | | 363.0 |

TABLE 1-continued

| Ex.No. | IUPAC name | MS |
|---|---|---|
| 13 | cis-3-((4-fluoro-2-methylphenoxy)methyl)cyclobutyl 6-oxo-7-oxa-2,5-diazaspiro[3.4]octane-2-carboxylate | 363.0 |
| 14 | cis-3-((2-chloro-4-fluorophenoxy)methyl)cyclobutyl 6-oxo-7-oxa-2,5-diazaspiro[3.4]octane-2-carboxylate | 382.9 |
| 15 | cis-3-((4-chloro-2-fluorophenoxy)methyl)cyclobutyl 6-oxo-7-oxa-2,5-diazaspiro[3.4]octane-2-carboxylate | 382.9 |
| 16 | cis-3-((2,3,4-trifluorophenoxy)methyl)cyclobutyl 6-oxo-7-oxa-2,5-diazaspiro[3.4]octane-2-carboxylate | 385.0 |
| 17 | cis-3-((2,4,5-trifluorophenoxy)methyl)cyclobutyl 6-oxo-7-oxa-2,5-diazaspiro[3.4]octane-2-carboxylate | 384.9 |
| 18 | cis-3-((2,4,6-trifluorophenoxy)methyl)cyclobutyl 6-oxo-7-oxa-2,5-diazaspiro[3.4]octane-2-carboxylate | 384.9 |

TABLE 1-continued

| Ex.No. | IUPAC name | structure formula | MS |
|---|---|---|---|
| 19 | cis-3-((2-fluoro-4-(trifluoromethyl)phenoxy)methyl)cyclobutyl 6-oxo-7-oxa-2,5-diazaspiro[3.4]octane-2-carboxylate | | 417.0 |
| 20 | cis-3-((2-chloro-4-(trifluoromethyl)phenoxy)methyl)cyclobutyl 6-oxo-7-oxa-2,5-diazaspiro[3.4]octane-2-carboxylate | | 432.9 |
| 21 | trans-3-((2,3,4-trifluorophenoxy)methyl)cyclobutyl 6-oxo-7-oxa-2,5-diazaspiro[3.4]octane-2-carboxylate | | 385.0 |
| 22 | trans-3-((2-fluoro-4-(trifluoromethyl)phenoxy)methyl)cyclobutyl 6-oxo-7-oxa-2,5-diazaspiro[3.4]octane-2-carboxylate | | 416.9 |
| 23 | (cis-3-(2,4,6-trifluorophenoxy)cyclobutyl)methyl 6-oxo-7-oxa-2,5-diazaspiro[3.4]octane-2-carboxylate | | 384.9 |
| 24 | (cis-3-(2-fluoro-4-(trifluoramethyl)phenoxy)cyclobutyl)methyl 6-oxo-7-oxa-2,5-diazaspiro[3.4]octane-2-carboxylate | | 416.9 |

TABLE 1-continued

| Ex.No. | IUPAC name | structure formula | MS |
|---|---|---|---|
| 25 | (trans-3-(2,4,6-trifluorophenoxy)cyclobutyl)methyl 6-oxo-7-oxa-2,5-diazaspiro[3.4]octane-2-carboxylate | 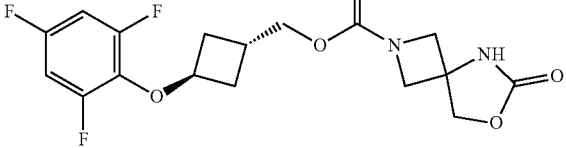 | 384.9 |
| 26 | (cis-3-(2-chloro-4-(trifluoromethyl)phenoxy)cyclobutyl)methyl 6-oxo-7-oxa-2,5-diazaspiro[3.4]octane-2-carboxylate | 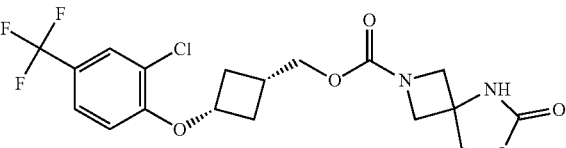 | 432.8 |
| 27 | (trans-3-(2-chloro-4-(trifluoromethyl)phenoxy)cyclobutyl)methyl 6-oxo-7-oxa-2,5-diazaspiro[3.4]octane-2-carboxylate | 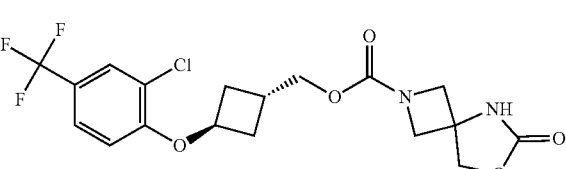 | 432.9 |
| 28 | cis-3-(((3-chloro-4-methylbenzyl)oxy)methyl)cyclobutyl 6-oxo-7-oxa-2,5-diazaspiro[3.4]octane-2-carboxylate | 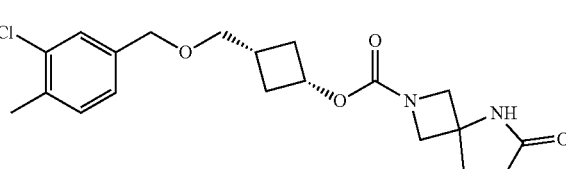 | 392.9 |
| 29 | cis-3-(((4-chloro-3-methylbenzyl)oxy)methyl)cyclobutyl 6-oxo-7-oxa-2,5-diazaspiro[3.4]octane-2-carboxylate | 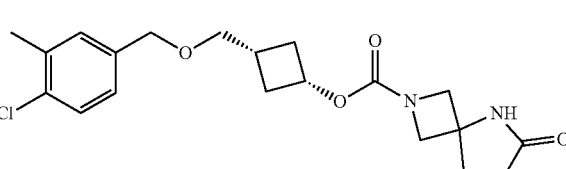 | 392.9 |
| 30 | cis-3-(((2-chloro-4-fluorobenzyl)oxy)methyl)cyclobutyl 6-oxo-7-oxa-2,5-diazaspiro[3.4]octane-2-carboxylate | 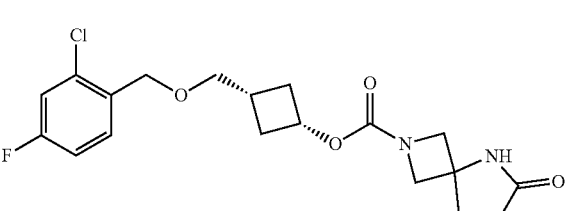 | 397.0 |
| 31 | cis-3-(((2,3,4-trifluorobenzyl)oxy)methyl)cyclobutyl 6-oxo-7-oxa-2,5-diazaspiro[3.4]octane-2-carboxylate | 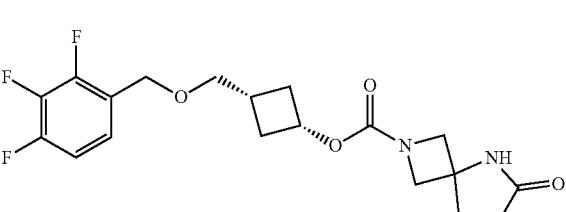 | 398.9 |
| 32 | cis-3-(((2,4,5-trifluorobenzyl)oxy)methyl)cyclobutyl 6-oxo-7-oxa-2,5-diazaspiro[3.4]octane-2-carboxylate | 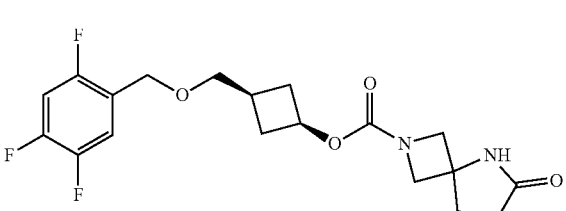 | 398.9 |

TABLE 1-continued

| Ex.No. | IUPAC name | MS |
|---|---|---|
| 33 | cis-3-(((2,4,6-trifluorobenzyl)oxy)methyl)cyclobutyl 6-oxo-7-oxa-2,5-diazaspiro[3.4]octane-2-carboxylate | 398.9 |
| 34 | trans-3-(2-fluoro-4-(trifluoromethyl)phenoxy)cyclobutyl 6-oxo-7-oxa-2,5-diazaspiro[3.4]octane-2-carboxylate | 403.1 |
| 35 | cis-3-((2,3,4-trifluorophenoxy)methyl)cyclobutyl 2-oxo-3-oxa-1,7-diazaspiro[4.4]nonane-7-carboxylate (optical isomer) | 399.0 |
| 36 | cis-3-(((2-fluoro-4-(trifluoromethyl)benzyl)oxy)methyl)cyclobutyl 6-oxo-7-oxa-2,5-diazaspiro[3.4]octane-2-carboxylate | 431.0 |
| 37 | trans-4-(2-fluoro-4-(trifluoromethyl)phenoxy)cyclohexyl 6-oxo-7-oxa-2,5-diazaspiro[3.4]octane-2-carboxylate | 431.0 |
| 38 | cis-4-(2-fluoro-4-(trifluoromethyl)phenoxy)cyclohexyl 6-oxo-7-oxa-2,5-diazaspiro[3.4]octane-2-carboxylate | 430.9 |
| 39 | trans-3-(2,3,4-trifluorophenoxy)cyclobutyl 6-oxo-7-oxa-2,5-diazaspiro[3.4]octane-2-carboxylate | 371.0 |

TABLE 1-continued

| Ex.No. | IUPAC name | structure formula | MS |
|---|---|---|---|
| 40 | cis-3-((2,4-difluorobenzyl)oxy)cyclobutyl 6-oxo-7-oxa-2,5-diazaspiro[3.4]octane-2-carboxylate | | 367.1 |
| 41 | cis-3-((3,4-difluorobenzyl)oxy)cyclobutyl 6-oxo-7-oxa-2,5-diazaspiro[3.4]octane-2-carboxylate | | 367.0 |
| 42 | trans-3-(benzyloxy)cyclobutyl 6-oxo-7-oxa-2,5-diazaspiro[3.4]octane-2-carboxylate | | 331.0 |
| 43 | trans-3-(2,4,6-fluorophenoxy)cyclobutyl 6-oxo-7-oxa-2,5-diazaspiro[3.4]octane-2-carboxylate | | 370.9 |
| 44 | cis-3-(2-chloro-4-fluorophenoxy)cyclobutyl 6-oxo-7-oxa-2,5-diazaspiro[3.4]octane-2-carboxylate | | 368.9 |
| 45 | cis-3-(3-fluoro-4-methylphenoxy)cyclobutyl 6-oxo-7-oxa-2,5-diazaspiro[3.4]octane-2-carboxylate | | 348.9 |
| 46 | cis-3-(2,4,6-trifluorophenoxy)cyclobutyl 6-oxo-7-oxa-2,5-diazaspiro[3.4]octane-2-carboxylate | | 370.9 |

TABLE 1-continued

| Ex.No. | IUPAC name | structure formula | MS |
|---|---|---|---|
| 47 | cis-3-(4-chlorophenoxy)cyclobutyl 6-oxo-7-oxa-2,5-diazaspiro[3.4]octane-2-carboxylate | | 351.0 |
| 48 | cis-3-(4-(trifluoromethyl)phenoxy)cyclobutyl 6-oxo-7-oxa-2,5-diazaspiro[3.4]octane-2-carboxylate | | 385.1 |
| 49 | cis-3-(3-chlorophenoxy)cyclobutyl 6-oxo-7-oxa-2,5-diazaspiro[3.4]octane-2-carboxylate | | 351.1 |
| 50 | cis-3-(4-fluoro-3-methylphenoxy)cyclobutyl 6-oxo-7-oxa-2,5-diazaspiro[3.4]octane-2-carboxylate | | 349.1 |
| 51 | cis-3-(2,3,4-trifluorophenoxy)cyclobutyl 6-oxo-7-oxa-2,5-diazaspiro[3.4]octane-2-carboxylate | | 371.0 |
| 52 | cis-3-(2-chlorophenoxy)cyclobutyl 6-oxo-7-oxa-2,5-diazaspiro[3.4]octane-2-carboxylate | | 351.0 |
| 53 | cis-3-(4-methylphenoxy)cyclobutyl 6-oxo-7-oxa-2,5-diazaspiro[3.4]octane-2-carboxylate | | 331.1 |

TABLE 1-continued

| Ex.No. | IUPAC name | structure formula | MS |
|---|---|---|---|
| 54 | cis-3-(4-chloro-2-fluorophenoxy)cyclobutyl 6-oxo-7-oxa-2,5-diazaspiro[3.4]octane-2-carboxylate | | 369.0 |
| 55 | cis-3-(4-fluoro-2-methylphenoxy)cyclobutyl 6-oxo-7-oxa-2,5-diazaspiro[3.4]octane-2-carboxylate | | 349.1 |
| 56 | cis-3-(2-fluoro-4-methylphenoxy)cyclobutyl 6-oxo-7-oxa-2,5-diazaspiro[3.4]octane-2-carboxylate | | 349.0 |
| 57 | cis-3-(2,4,5-trifluorophenoxy)cyclobutyl 6-oxo-7-oxa-2,5-diazaspiro[3.4]octane-2-carboxylate | | 371.0 |
| 58 | cis-3-(benzyloxy)-1-methylcyclobutyl 6-oxo-7-oxa-2,5-diazaspiro[3.4]octane-2-carboxylate | | 345.1 |
| 59 | trans-3-(benzyloxy)-1-methylcyclobutyl 6-oxo-7-oxa-2,5-diazaspiro[3.4]octane-2-carboxylate | | 345.1 |

TABLE 1-continued

| Ex.No. | IUPAC name | structure formula | MS |
|---|---|---|---|
| 60 | cis-1-methyl-3-(2,4,6-trifluorophenoxy)cyclobutyl 6-oxo-7-oxa-2,5-diazaspiro[3.4]octane-2-carboxylate | | 385.0 |
| 61 | trans-1-methyl-3-(2,4,6-trifluorophenoxy)cyclobutyl 6-oxo-7-oxa-2,5-diazaspiro[3.4]octane-2-carboxylate | | 385.0 |
| 62 | trans-3-((2-fluoro-4-(trifluoromethyl)benzyl)oxy)cyclobutyl 6-oxo-7-oxa-2,5-diazaspiro[3.4]octane-2-carboxylate | | 417.0 |
| 63 | cis-3-(2-chloro-4-fluorophenoxy)-3-methylcyclobutyl 6-oxo-7-oxa-2,5-diazaspiro[3.4]octane-2-carboxylate | | 383.0 |
| 64 | cis-3-((2,3,4-trifluorophenoxy)methyl)cyclobutyl 6-oxo-2,5-diazaspiro[3.4]octane-2-carboxylate | | 385.0 |

Reference Example 1

(1r,3r)-3-(benzyloxy)cyclobutan-1-ol (identical to trans-3-(benzyloxy)cyclobutanol)

A) (1r,3r)-3-(benzyloxy)cyclobutyl 4-nitrobenzoate

To a mixture of 3-(benzyloxy)cyclobutanone (24.7 g) and methanol (300 mL) was added sodium borohydride (5.30 g) at 0° C. small by small, and the mixture was stirred at 23° C. for 2 hr. The methanol was evaporated under reduced pressure, and the residue was diluted with 0.5M hydrochloric acid (200 mL). The mixture was extracted with ethyl acetate. The extract was washed with saturated brine, dried over anhydrous sodium sulfate, and concentrated under reduced pressure. The residue was purified by silica gel column chromatography (ethyl acetate/hexane) to give a crude product (21.8 g). This crude product was resolved by HPLC (column: CHIRALPAK AD (trade name), 50 mmID× 500 mmL, manufactured by Daicel Corporation, mobile phase: hexane/ethanol (900/100 (v/v))) to give (1s,3s)-3-(benzyloxy)cyclobutan-1-ol (17.7 g). To a mixture of the obtained (1s,3s)-3-(benzyloxy)cyclobutan-1-ol (10.0 g), 4-nitrobenzoic acid (14.07 g), triphenylphosphine (22.07 g) and THF (125 mL) was added dropwise DIAD (18.91 g) at 0° C., and the mixture was warmed to room temperature. The mixture was stirred overnight at room temperature, diluted with toluene, and concentrated under reduced pressure to about 100 mL. The residue was purified by silica gel column chromatography (ethyl acetate/hexane) to give the title compound (18.45 g).

$^1$H NMR (300 MHz, DMSO-d$_6$) 52.42-2.49 (4H, m), 4.34 (1H, quin, J=5.8 Hz), 4.42 (2H, s), 5.21-5.40 (1H, m), 7.18-7.42 (5H, m), 8.15-8.27 (2H, m), 8.30-8.46 (2H, m).

B) (1r,3r)-3-(benzyloxy)cyclobutan-1-ol

To a mixture of (1r,3r)-3-(benzyloxy)cyclobutyl 4-nitrobenzoate (18.37 g) and THF (100 mL)/methanol (20.0 mL) was added dropwise 2M aqueous sodium hydroxide solution (84 mL) at 0° C., and the mixture was stirred overnight at room temperature. The organic solvent was evaporated under reduced pressure, and the residue was partitioned between water and ethyl acetate. The extract was washed with saturated brine, dried over anhydrous sodium sulfate, and concentrated under reduced pressure. The residue was purified by silica gel column chromatography (ethyl acetate/hexane) to give the title compound (9.65 g).

$^1$H NMR (300 MHz, DMSO-d$_6$) 51.95-2.08 (2H, m), 2.12-2.25 (2H, m), 4.09-4.20 (1H, m), 4.27 (1H, tq, J=7.1, 4.9 Hz), 4.33 (2H, s), 4.98 (1H, d, J=5.3 Hz), 7.21-7.42 (5H, m).

Experimental Example 1: Cloning of Human MGLL Encoding MAGL Protein and Construction of Expression Plasmid Human MGLL cDNA was obtained by PCR using human ORF Clone (DNA Form; Clone ID: 100004585) as a template. For PCR, two kinds of primers:

[SEQ ID NO: 1]
5'-CCACCATCATCACGGATCCATGCCAGAGGAAAGTTCCCCCA-3'
and

[SEQ ID NO: 2]
5'-TGGTGCTCGAGTGCGGCCGCTCAGGGTGGGGACGCAGTTC-3' and PrimeSTAR MAX DNA Polymerase (Takara Bio Inc.) were used, and (1) reaction at 98° C. for 1 min, (2) 25 cycles of reaction at 98° C. for 10 sec and 68° C. for 10 sec as one cycle, and (3) reaction at 72° C. for 1 min were performed. The obtained PCR product was digested with Bam HI and Not I (Takara Bio Inc.), inserted into the Bam HI/Not I site of pET21HH(V) (pET21a (Novagen) inserted with His x6 and TEV Protease recognition sequence) by using Ligation High (Toyobo Co., Ltd.), and introduced into ECOS™ JM109 (Nippon Gene Co., Ltd.), whereby expression plasmid pET21HH(V)/His-hMGLLv2 for *Escherichia coli* was constructed.

Experimental Example 2: Preparation of Recombinant Polyhistidine Tagged Human MAGL Protein Recombinant His-hMAGL protein was prepared by transforming ECOS™ Competent *E. coli* BL21(DE3) (Nippon Gene Co., Ltd.) with the pET21HH(V)/His-hMGLLv2 plasmid prepared above. *Escherichia coli* obtained by transformation was inoculated to 10 mL of LB medium (1% peptone, 0.5% yeast extract, 0.5% sodium chloride, 0.01% ampicillin), and cultured at 30° C. for 16 hr. The obtained culture medium (5 mL) was transplanted into a 2 L Sakaguchi flask containing 1 L of main fermentation medium (1.05% M9 MEDIUM BROTH (AMRESCO LLC), 0.5% yeast extract, 1.5% sorbitol, 1.5% casamino acid, 0.024% magnesium sulfate, 0.01% antifoaming agent PE-L (Wako Pure Chemical Industries, Ltd.), 0.01% ampicillin), and shaking culture at 37° C. and 150 rpm was started. When the turbidity of the culture medium reached about 500 Klett unit, the culture temperature was lowered to 16° C., isopropyl-β-D-thiogalactopyranoside (IPTG) was added to a final concentration of 1 mM, and the mixture was further cultured for 19 hr. After the completion of culture, the culture medium was centrifuged (4° C., 6,000 rpm, 10 min) to give His-hMAGL-expressed *Escherichia coli*. Then, His-hMAGL-expressed *Escherichia coli* was suspended in 50 mM Tris-HCl (pH 8.0, 100 ml) containing 1% Triton X-100, 20 mM imidazole, 3 mM DTT, 5 U/mL Benzonase (Merck) and 150 mM NaCl, and the suspension was sufficiently cooled, and subjected to sonication at AMPLITUDE=60%, 15 sec/ON, 30 sec/OFF for 3 min using ¾" solid type crushed horn of BRANSON Digital Sonifier 450 (Central Scientific Commerce, Inc.). Furthermore, the homogenate was centrifuged (4° C., 6,000 rpm, 20 min) and the supernatant was obtained. As the purification apparatus, AKTA explorer 10s (GE Healthcare Japan Corporation) was used at 4° C. To the obtained supernatant was added 5M NaCl to the final salt concentration of 0.3 M, and the mixture was flown through and adsorbed to 5 mL of Ni-NTA Superflow Cartridges (QIAGEN) equilibrated in advance with buffer A (50 mM Tris-HCl (pH 8.0) containing 0.05% TritonX-100, 1 mM DTT, 300 mM NaCl). The column was sufficiently washed with buffer A containing 20 mM imidazole and His-hMAGL was eluted with buffer A containing imidazole at a final concentration of 250 mM. The eluate was further subjected to gel filtration using HiLoad 16/600 Superdex 200 pg (GE Healthcare Japan Corporation) equilibrated with 50 mM Tris-HCl pH 8.0 containing 10% glycerol, 0.05% TritonX-100, 1 mM DTT and 150 mM NaCl. The eluted fraction was concentrated by Amicon Ultra-15 10K (Merck Millipore) to give purified His-hMAGL protein. The protein concentration was measured by BCA Protein Assay Kit (Thermo Fisher Scientific) using BSA as the standard.

Experimental Example 3: Measurement of MAGL inhibitory activity

The His-hMAGL obtained above was diluted with enzyme reaction buffer (10 mM Tris-HCl, pH 7.5, 1 mM EDTA, 0.025 (w/v) % Triton X-100, 0.01% Bovine serum albumin) to a concentration of 7.5 ng/mL. To each well of a 384 well assay plate (Greiner 781280) was added a solution (5 µL) of a test compound dissolved in dimethyl sulfoxide (DMSO), which was diluted with the above-mentioned enzyme reaction buffer, then His-hMAGL solution (5 µL) diluted to a concentration of 7.5 ng/mL was added, and the mixture was incubated at room temperature for 60 min. Thereafter, to each well was added 5 µL of 150 µM 2-arachidonylglycerol (Tocris Bioscience), and the mixture was incubated at room temperature for 10 min. Then, 10 µL of 2% formic acid (Wako Pure Chemical Industries, Ltd.) was added to stop the reaction. Furthermore, acetonitrile (50 µL) containing 3 µM arachidonic acid-d8 (Cayman Chemical Company) was added and the mixture was stirred.

The amount of arachidonic acid in the obtained enzyme reaction mixture was calculated by measuring by RapidFire-mass spectrometry and correcting by the amount of arachidonic acid-d8. High Throughput online solid phase extraction was performed using RapidFire 300™ system (Agilent Technologies, Inc.). Samples were loaded on SPE C4 cartridge (Agilent Technologies, Inc.) and desalted with 0.2

(v/v) % acetic acid (Wako Pure Chemical Industries, Ltd.) in ultrapure water/acetonitrile (70/30, v/v) at a flow rate of 1.5 mL/min, eluted at a flow rate of 0.5 mL/min with 0.2 (v/v) % acetic acid dissolved in acetonitrile/ultrapure water (90/10, v/v), and injected into the mass spectrometry part. The injection needle was washed with ultrapure water (500 millisecond) and acetonitrile (500 millisecond) to minimize carry-over. The suction time (injection loop 5 µL), load/cleansing time, elution time and re-equilibration time were adjusted to 300, 3000, 4250 and 1000 milliseconds, respectively, and the total cycle time was adjusted to about 10.0 seconds. The RapidFire300 system was controlled by RapidFire UI software version 3.6 (Agilent Technologies, Inc.).

The mass spectrometry of the resultant product was performed using API4000™ triple quadrupole mass spectrometer (AB SCIEX) equipped with an electrospray ion sauce (TurboIon Spray™) in a negative selected reaction monitoring (SRM) mode. The conditions of SRM are shown below. The parameters of the instrument were optimized as follows: capillary temperature 600° C., ion spray voltage −4.5 kV, collision gas 8, curtain gas 15 psi, ion source gas 1 60 psi, ion source gas 2 60 psi. The mass spectrometer was controlled by Analyst™ software version 1.5.1 (AB SCIEX). The peak area integration was analyzed using RapidFire integrator software version 3.6 (Agilent Technologies, Inc.).

MAGL inhibitory rate (%) was calculated according to the following calculation formula.

(1−(arachidonic acid production amount of test compound addition group−arachidonic acid production amount of enzyme-free group)÷(arachidonic acid production amount of test compound-free group−arachidonic acid production amount of enzyme-free group))×100

The results are shown in the following Table 2.

TABLE 2

| Example | % inhibition (10 µM) |
|---|---|
| 1 | 100 |
| 2 | 101 |
| 3 | 101 |
| 4 | 100 |
| 5 | 99 |
| 6 | 101 |
| 7 | 100 |
| 8 | 100 |
| 9 | 99 |
| 10 | 99 |
| 11 | 100 |
| 12 | 101 |
| 13 | 102 |
| 14 | 98 |
| 15 | 103 |
| 16 | 100 |
| 17 | 101 |
| 18 | 102 |
| 19 | 98 |
| 20 | 100 |
| 21 | 100 |
| 22 | 103 |
| 23 | 100 |
| 24 | 103 |
| 25 | 100 |
| 26 | 100 |
| 27 | 100 |
| 28 | 100 |
| 29 | 100 |
| 30 | 100 |
| 31 | 100 |
| 32 | 100 |
| 33 | 101 |

TABLE 2-continued

| Example | % inhibition (10 µM) |
|---|---|
| 34 | 99 |
| 35 | 100 |
| 36 | 100 |
| 37 | 101 |
| 38 | 102 |
| 39 | 100 |
| 40 | 100 |
| 41 | 99 |
| 42 | 99 |
| 43 | 102 |
| 44 | 103 |
| 45 | 98 |
| 46 | 102 |
| 47 | 100 |
| 48 | 100 |
| 49 | 100 |
| 50 | 99 |
| 51 | 99 |
| 52 | 100 |
| 53 | 101 |
| 54 | 100 |
| 55 | 100 |
| 56 | 101 |
| 57 | 100 |
| 58 | 93 |
| 59 | 99 |
| 60 | 98 |
| 61 | 100 |
| 62 | 99 |
| 63 | 100 |
| 64 | 101 |

As is clear from Table 2, the compound of the present invention has a MAGL inhibitory activity.

Experimental Example 4: Measurement of Intracerebral 2-AG and Arachidonic Acid Concentrations As the mouse, 8-week-old male C57BL/6J mice (CLEA Japan, Inc.) were used (6 mice/group). Administration solutions were prepared by suspending the test compounds (compound 1 (compound of Example 16), compound 2 (compound of Example 18) and compound 3 (compound of Example 46)) in 0.5% methylcellulose solution (Wako Pure Chemical Industries, Ltd.). The dose of the test compound was prepared to be 1 mg/kg body weight/10 mL. The test compounds were administered by gavage at 1 mg/kg body weight. The cerebrum was isolated after the administration of the test compound (isolation time after the administration of the test compound is shown in Table 3), and the cerebrum hemisphere was extracted. The obtained cerebrum hemisphere was frozen on dry ice, and the frozen tissue weight was measured.

The cerebral tissue was homogenized with 4-fold (v/w) of isopropanol (IPA), and double diluted with IPA. To the diluted sample (200 µL) was added internal standard solution (5 µL) ([5,6,8,9,11,12,14,15-D8]-(5Z,8Z,11Z,14Z)-5,8,11,14-eicosatetraenoic acid (AA-$d_8$, 0.5 nmol/mL IPA) and [5,6,8,9,11,12,14,15-D8]-(5Z,8Z,11Z,14Z)-5,8,11,14-eicosatetraenoyl-2-glycerol ester (2-AG-$d_8$, 0.5 nmol/mL IPA)), and the mixture was centrifuged at 15000 rpm for 5 min. The supernatant was injected to liquid chromatography mass spectrometer for quantitative analysis.

For liquid chromatography, Shimadzu LC20A system (Shimadzu Corporation) was used. The separation was performed by gradient elution method with mobile phase A (10 mmol/L $HCOONH_4$/HCOOH (100:0.2, v/v)) and mobile phase B (ethanol/IPA (3:2, v/v)) using Shim-pack XR-ODS (2.2 μm, 2.0×30 mm, Shimadzu Corporation) at column temperature of 50° C., at flow rate of 0.5 mL/min. The gradient conditions are as follows: 0-1 min, 1% B; 1-1.2 min, 1-55% B; 1.2-2.7 min, 55-75% B; 2.7-3.5 min, 75-99% B; 3.5-6 min, 99% B; 6-8 min, 1% B.

For mass spectrometer, API5000 (AB SCIEX) was used. The eluate from the liquid chromatography was directly ionized by turbospray ionization method, where (5Z,8Z,11Z,14Z)5,8,11,14-eicosatetraenoic acid (AA) and AA-ds were measured by negative ionization mode, and (5Z,8Z,11Z,14Z)5,8,11,14-eicosatetraenoyl-2-glycerol ester (2-AG) and 2-AG-$d_8$ were measured by positive ionization mode. Detection conditions of the mass spectrometer are shown in Table 4.

A solution for calibration curve was prepared to the concentration of 2, 5, 10, 20, 50, 100, 200, 500, 1000 nmol/mL of acetonitrile. These solutions (10 μL) was mixed with 200 μL of IPA and 5 μL of internal standard solution, and the mixture was centrifuged at 15000 rpm for 5 min, and the supernatant was injected to liquid chromatography mass spectrometer. Liner regression with $1/x^2$ weighting was used for the calibration curve fitting, and the quantitativity was confirmed by accuracy of 100±20% and $R^2$>0.99.

The results are shown in Table 5.

As is clear from Table 5, the compounds 1, 2 and 3 were migrated into brain by oral administration to C57BL/6J mice, and these compounds increased intracerebral 2-AG concentration, and simultaneously decreased intracerebral arachidonic acid concentration, compared to control.

TABLE 3

| test compound | isolation time after the administration of test compound (hour) |
|---|---|
| compound 1 | 1 |
| compound 2 | 1 |
| compound 3 | 1 |

TABLE 4 mass spectrometer parameter

| target molecule | polarity | Q1 | Q3 | retention time (msec) | DP (V) | EP (V) | CE (V) | CXP (V) |
|---|---|---|---|---|---|---|---|---|
| arachidonic acid | − | 303.2 | 205.2 | 25 | −90 | −11 | −17 | −15 |
| arachidonic acid-d8 | − | 311.4 | 267.4 | 25 | −175 | −10 | −22 | −17 |
| 2-arachidonyl glycerol | + | 379.3 | 95 | 25 | 181 | 10 | 91 | 14 |
| 2-arachidonyl glycerol-d8 | + | 387.4 | 294.2 | 25 | 161 | 10 | 23 | 18 |

DP: declustering potential
EP: entrance potential
CE: cleavage energy
CXP: collision cell exit potential

TABLE 5

| | 2-AG concentration (nmol/g) | arachidonic acid concentration (nmol/g) |
|---|---|---|
| control | 13.5 | 203.1 |
| compound 1 | 82.3 | 119.8 |
| compound 2 | 128.7 | 84.3 |
| compound 3 | 79.0 | 138.0 |

Formulation Examples

Medicaments containing the compound of the present invention as an active ingredient can be produced, for example, by the following formulations.

| 1. capsule | | |
|---|---|---|
| (1) | compound obtained in Example 1 | 10 mg |
| (2) | lactose | 90 mg |
| (3) | microcrystalline cellulose | 70 mg |
| (4) | magnesium stearate | 10 mg |
| | 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

| 2. tablet | | |
|---|---|---|
| (1) | compound obtained in Example 1 | 10 mg |
| (2) | lactose | 35 mg |
| (3) | cornstarch | 150 mg |
| (4) | microcrystalline cellulose | 30 mg |
| (5) | magnesium stearate | 5 mg |
| | 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having an MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like can be provided.

This application is based on patent application No. 2017-190838 filed on Sep. 29, 2017 in Japan, the contents of which are encompassed in full herein.

The invention claimed is:

1. A compound represented by the formula (I):

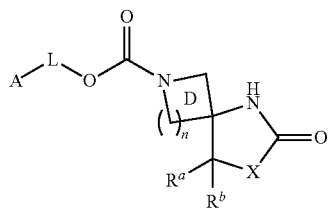

wherein

A is an optionally substituted saturated cyclic group,

L is a bond or a $C_{1-3}$ alkylene group optionally substituted by halogen atom(s), Ring D is a ring optionally further substituted by $C_{1-6}$ alkyl group(s) optionally substituted by halogen atom(s), n is 1 or 2, X is —O—, —$CR^1R^2$— or —$NR^3$—, $R^a$ and $R^b$ are each independently a hydrogen atom or a $C_{1-6}$ alkyl group optionally substituted by halogen atom(s), and $R^1$, $R^2$ and $R^3$ are each independently a hydrogen atom or a substituent, or a salt thereof.

2. The compound or salt according to claim 1, wherein A is a $C_{3-10}$ cycloalkyl group substituted by 1 to 3 substituents selected from (a) a $C_{6-14}$ aryloxy group optionally substituted by 1 to 4 substituents selected from
  (i) a halogen atom, and
  (ii) an optionally halogenated $C_{1-6}$ alkyl group, (b) a $C_{6-14}$ aryloxy-$C_{1-6}$ alkyl group optionally substituted by 1 to 4 substituents selected from
  (i) a halogen atom, and
  (ii) an optionally halogenated $C_{1-6}$ alkyl group, (c) a $C_{7-16}$ aralkyloxy group optionally substituted by 1 to 4 substituents selected from
  (i) a halogen atom, and
  (ii) an optionally halogenated $C_{1-6}$ alkyl group, and (d) a $C_{7-16}$ aralkyloxy-$C_{1-6}$ alkyl group optionally substituted by 1 to 4 substituents selected from
  (i) a halogen atom, and
  (ii) an optionally halogenated $C_{1-6}$ alkyl group, and optionally further substituted by 1 to 3 $C_{1-6}$ alkyl groups;

L is bond or a $C_{1-3}$ alkylene group;

Ring D is a 4- or 5-membered nitrogen-containing heterocycle;

n is 1 or 2;

X is —O— or —$CH_2$—; and $R^a$ and $R^b$ are both hydrogen atoms.

3. The compound or salt according to claim 1, wherein A is a cyclobutyl group substituted by one substituent selected from
(a) a phenoxy group substituted by 3 halogen atoms, and
(b) a phenoxymethyl group substituted by 3 halogen atoms;

L is bond;

Ring D is an azetidine ring;

n is 1;

X is —O—; and $R^a$ and $R^b$ are both hydrogen atoms.

4. cis-3-((2,3,4-Trifluorophenoxy)methyl)cyclobutyl 6-oxo-7-oxa-2,5-diazaspiro[3.4]octane-2-carboxylate or a salt thereof.

5. cis-3-((2,4,6-Trifluorophenoxy)methyl)cyclobutyl 6-oxo-7-oxa-2,5-diazaspiro[3.4]octane-2-carboxylate or a salt thereof.

6. cis-3-(2,4,6-Trifluorophenoxy)cyclobutyl 6-oxo-7-oxa-2,5-diazaspiro[3.4]octane-2-carboxylate or a salt thereof.

7. A medicament comprising the compound or salt according to claim 1.

8. The medicament according to claim 7, which is a monoacylglycerol lipase inhibitor.

9. The medicament according to claim 7, which is an agent for the prophylaxis or treatment of Alzheimer's disease, Parkinson's disease, Huntington's disease, amyotrophic lateral sclerosis, multiple sclerosis, anxiety disorder, pain, epilepsy or depression.

10. A method of inhibiting monoacylglycerol lipase in a mammal, which comprises administering an effective amount of the compound or salt according to claim 1 to the mammal.

11. A method for the prophylaxis or treatment of Alzheimer's disease, Parkinson's disease, Huntington's disease, amyotrophic lateral sclerosis, multiple sclerosis, anxiety disorder, pain, epilepsy or depression in a mammal, which comprises administering an effective amount of the compound or salt according to claim 1 to the mammal.

12. The compound or salt according to claim 1 for use in the prophylaxis or treatment of Alzheimer's disease, Parkinson's disease, Huntington's disease, amyotrophic lateral sclerosis, multiple sclerosis, anxiety disorder, pain, epilepsy or depression.

* * * * *

UNITED STATES PATENT AND TRADEMARK OFFICE
CERTIFICATE OF CORRECTION

| | | |
|---|---|---|
| PATENT NO. | : 11,274,101 B2 | Page 1 of 1 |
| APPLICATION NO. | : 16/651840 | |
| DATED | : March 15, 2022 | |
| INVENTOR(S) | : Kamata et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 109 days.

Signed and Sealed this
Fourteenth Day of January, 2025

Derrick Brent
*Acting Director of the United States Patent and Trademark Office*